US012807579B2

(12) United States Patent
Huang et al.

(10) Patent No.: US 12,807,579 B2
(45) Date of Patent: Nov. 24, 2026

(54) PHARMACEUTICAL USE AND PREPARATION METHOD FOR SUBSTITUTED HETEROARYL PHTHALAZINE DERIVATIVE

(71) Applicant: ORIGIANT PHARMACEUTICAL CO., LTD., Chengdu (CN)

(72) Inventors: Qi Huang, Chengdu (CN); Songlin Wan, Chengdu (CN); Guoliang Liu, Chengdu (CN); Yifeng Xiong, Chengdu (CN); Xiaoquan Wu, Chengdu (CN)

(73) Assignee: ORIGIANT PHARMACEUTICALS CO., LTD., Chengdu (CN)

(*) Notice: Subject to any disclaimer, the term of this patent is extended or adjusted under 35 U.S.C. 154(b) by 309 days.

(21) Appl. No.: 18/697,406

(22) PCT Filed: Sep. 30, 2022

(86) PCT No.: PCT/CN2022/123126

§ 371 (c)(1),
(2) Date: Mar. 29, 2024

(87) PCT Pub. No.: WO2023/051761

PCT Pub. Date: Apr. 6, 2023

(65) Prior Publication Data

US 2024/0391881 A1 Nov. 28, 2024

(30) Foreign Application Priority Data

Sep. 30, 2021 (CN) .......................... 202111166090.8

(51) Int. Cl.

| | |
|---|---|
| ***C07D 237/34*** | (2006.01) |
| ***A61K 31/502*** | (2006.01) |
| ***A61K 31/5025*** | (2006.01) |
| ***A61K 31/5377*** | (2006.01) |
| ***A61K 31/675*** | (2006.01) |
| ***C07D 401/12*** | (2006.01) |
| ***C07D 403/12*** | (2006.01) |
| ***C07D 471/04*** | (2006.01) |
| ***C07D 487/04*** | (2006.01) |
| ***C07D 495/04*** | (2006.01) |
| ***C07F 9/6509*** | (2006.01) |

(52) U.S. Cl.

CPC .......... *C07D 237/34* (2013.01); *A61K 31/502* (2013.01); *A61K 31/5025* (2013.01); *A61K 31/5377* (2013.01); *A61K 31/675* (2013.01); *C07D 401/12* (2013.01); *C07D 403/12* (2013.01); *C07D 471/04* (2013.01); *C07D 487/04* (2013.01); *C07D 495/04* (2013.01); *C07F 9/650947* (2013.01)

(58) Field of Classification Search

CPC .. C07D 237/34; C07D 401/12; C07D 403/12; C07D 471/04; A61K 31/502; A61K 31/5025; A61K 31/5377

USPC ........................................................... 514/80

See application file for complete search history.

(56) References Cited

U.S. PATENT DOCUMENTS

| | | | | |
|---|---|---|---|---|
| 3,753,988 | A | 8/1973 | Rodway et al. | |
| 5,324,727 | A | 6/1994 | Iwase et al. | |
| 6,365,589 | B1 * | 4/2002 | Gilligan | C07D 471/04 544/236 |
| 11,319,319 | B1 | 5/2022 | Dorich et al. | |
| 2009/0124624 | A1 | 5/2009 | Augereau et al. | |
| 2011/0160187 | A1 | 6/2011 | Yoon et al. | |
| 2024/0262806 | A1 * | 8/2024 | Zhang | C07D 405/14 |

FOREIGN PATENT DOCUMENTS

| | | |
|---|---|---|
| CN | 115433163 | 12/2022 |
| CN | 116390914 | 7/2023 |
| CN | 117580826 | 2/2024 |
| CN | 118234730 | 6/2024 |
| CN | 118302417 | 7/2024 |
| JP | S4839944 | 11/1973 |
| JP | H06135938 | 5/1994 |
| JP | 2007536276 | 12/2007 |
| JP | 2009120486 | 6/2009 |
| WO | WO-2006/004589 | 1/2006 |
| WO | WO-2007/066615 | 6/2007 |
| WO | 2008124083 | 10/2008 |
| WO | WO-2018/080216 | 5/2018 |
| WO | WO-2018/221433 | 12/2018 |
| WO | 2020037116 | 2/2020 |

(Continued)

OTHER PUBLICATIONS

Stimac et al. Journal of Heterocyclic Chemistry (1991), 28(2), 417-23. (Year: 1991).*

(Continued)

*Primary Examiner* — Kahsay Habte

(74) *Attorney, Agent, or Firm* — JCIPRNET

(57) ABSTRACT

Provided are a substituted heteroaryl phthalazine derivative as shown in formula (I-0), a use thereof as an NLRP3 inhibitor, and a preparation method therefor; the derivative has relatively good NLRP3 inhibitory activity.

(I-0)

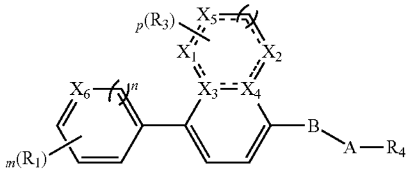

20 Claims, No Drawings

(56) References Cited

FOREIGN PATENT DOCUMENTS

| | | | |
|---|---|---|---|
| WO | 2020051207 | 3/2020 | |
| WO | WO-2020/234715 | 11/2020 | |
| WO | WO-2022/135567 | 6/2022 | |
| WO | WO-2022/216971 | 10/2022 | |
| WO | 2022253326 | 12/2022 | |
| WO | 2023003002 | 1/2023 | |
| WO | 2023275366 | 1/2023 | |
| WO | 2023278438 | 1/2023 | |
| WO | 2023028534 | 3/2023 | |
| WO | WO-2023028534 A1 * | 3/2023 | ........... C07D 519/00 |

OTHER PUBLICATIONS

Bollenbach et al., “Design and synthesis of 3-aminophthalazine derivatives and structural analogues as PDE5 inhibitors: anti-allodynic effect against neuropathic pain in a mouse model,” European Journal of Medicinal Chemistry (2019) 177:269-290.

First Office Action (including translation) for CN 202211210361.X, issued Jan. 27, 2024, pp. 1-17.

International Search Report (including translation) for PCT/CN2022/123126, issued Nov. 30, 2022, pp. 1-10.

Kassab, “Synthesis and behaviour of 4-(4'-chloro-3'-methylphenyl)-1(2H)-phthalazinone towards certain electrophiles and nucleophiles,” Egypt J. Chem. (2005) 48(2):183-199.

“The Second Office Action of China Counterpart Application”, with English translation thereof, issued on Sep. 27, 2024, pp. 1-18.

“Office Action of Canada Counterpart Application”, issued on Aug. 28, 2025, pp. 1-7.

“Office Action of Japan Counterpart Application”, with English translation thereof, issued on Apr. 1, 2025, pp. 1-12.

“Search Report of Europe Counterpart Application”, issued on Sep. 16, 2025, p. 1-p. 15.

“Office Action of Australia Counterpart Application”, issued on Mar. 5, 2025, pp. 1-4.

“Office Action of Australia Counterpart Application”, issued on Jul. 23, 2025, pp. 1-2.

* cited by examiner

PHARMACEUTICAL USE AND PREPARATION METHOD FOR SUBSTITUTED HETEROARYL PHTHALAZINE DERIVATIVE

CROSS REFERENCE TO RELATED APPLICATIONS

This application is a U.S. national stage application under 35 U.S.C. § 371 of International Application No. PCT/CN2022/123126, filed internationally on Sep. 30, 2022, which claims the benefit and priority of Chinese Application No. 202111166090.8 filed Sep. 30, 2021, the disclosure of which are hereby incorporated by reference in their entireties.

TECHNICAL FIELD

The present disclosure relates to the field of medicine, in particular to an NLRP3 inhibitor containing a compound represented by chemical formula (I) or a pharmaceutically acceptable salt thereof, a use thereof, and a preparation method therefor.

BACKGROUND

Inflammation is body's defense response to stimuli, and includes infectious inflammation and aseptic inflammation. Inflammation is mainly manifested as redness, swelling, heat, pain, and functional impairment, which are caused by increased permeability of endothelial cells and exudation of immune cells in plasma. Inflammatory responses will quickly end after tissue repair, but excessive production of cytokines leads to an inflammatory storm to damage the body. Inflammatory disorder is an important pathogenesis of many human diseases.

Natural immunity plays a crucial role in inflammation. Cells such as macrophages, dendritic cells, epithelial cells, endothelial cells, and fibroblasts are all involved in natural immune responses. Natural immunity recognizes pathogen-associated molecular patterns (PAMPs) and danger-associated molecular patterns (DAMPs) through pattern recognition receptors. At present, five types of pattern recognition receptors have been identified, including Toll-like receptors (TLRs), C-type lectin receptors (CLRs), RIG-like receptors (retinoic acid-inducible gene-1-like receptors, RLRs), intracellular DNA sensors (cytoplasmic DNA sensors), and NOD-like receptors (nucleotide-binding and oligomerization domain-like receptors, NLRs). These pattern recognition receptors are expressed on both immune and non-immune cells. After the pattern recognition receptors recognize corresponding ligands, multiple natural immune signaling pathways are activated to produce a series of cytokines that promote inflammation and type I interferon.

NLRs are a type of intracellular pattern recognition receptors. NLRs are widely expressed in various immune cells and epithelial cells, and can initiate natural immune responses by recognizing intracellular PAMPs and DAMPs such as cell pressure. The high evolutionary conservatism of NLRs also proves their crucial role in maintaining body's immune homeostasis. NLRs regulate the inflammatory responses by promoting the production of cytokines and chemokines and the expression of antibacterial related genes. Therefore. NLRs are closely related to human diseases such as infections, tumors, autoimmune diseases, and inflammatory disorders.

NLRs consist of a C-terminal LRR domain, a middle NOD domain, and an N-terminal effector domain. The C-terminal LRR domain is responsible for recognizing and binding ligands, the middle NOD domain has dNTPase (deoxynucleoside triphosphate) enzyme activity and is responsible for oligomerization of NLRs proteins, and the N-terminal effector domain exerts its effector function by interacting with other proteins. Currently, four N-terminal effector domains have been discovered, respectively an AD domain (acidic transactivation domain), a BIR domain (baculoviral inhibitory repeat-like domain), a CARD domain (caspase activation and recruitment domain), and a PYD domain (pyrin domain). According to the different N-terminal effector domains, the NOD-like receptors may be divided into four subfamilies, respectively an NLRA subfamily (Acidic domain containing), an NLRB subfamily (BIR domain containing), an NLRC subfamily (CARD domain containing), and an NLRP subfamily (pyrin domain containing). The NLRP subfamily includes 14 members, namely. NLRP1-14.

Inflammasomes are a type of polyprotein complexes that can mediate the activation of caspase-1. The activated caspase-1 promotes the processing and maturation of inflammatory cytokines IL-10p and IL-18, and can also lead to the occurrence of pyroptosis. The pyroptosis leads to the release of more DAMPs, which further enhances the immune responses. At present, it has been found that 8 types of activated NLRs form inflammasomes, respectively NLRP1, NLRP2, NLRP3, NLRP6, NLRP7, NLRP12, NLRC4, and NAIP.

An NLRP3 inflammasome consists of a pattern recognition receptor NLRP3, an adaptor protein ASC, and an effector protein pro-caspase-1. The NLRP3 consists of an N-terminal PYD domain, a middle NACHT domain, and a C-terminal LRR domain. The activation of the NLRP3 inflammasomes leads to the production of active caspase-1, which further promotes the pyroptosis. The NLRP3 inflammasomes can recognize various stimuli, including protozoa (malaria parasites, amoeba, etc.), viruses (adenoviruses, influenza viruses, Sendai viruses, etc.), fungi (*Saccharomyces cerevisiae, Candida albicans*, etc.), bacteria (*Listeria, Escherichia coli, Staphylococcus aureus*, etc.). The NLRP3 can also recognize many endogenous DAMPs, including uric acid crystals. ATP, pancreatic amyloid peptides, 0 starch-like protein spots, etc.

In addition, the abnormal activation of the NLRP3 inflammasomes is an important promoting factor for many major human diseases, such as rheumatoid arthritis, gouty arthritis, atherosclerosis, myocardial infarction, Parkinson's syndrome, Alzheimer's disease, infectious lung injury, pulmonary fibrosis, sepsis, ulcerative colitis, type 2 diabetes, sepsis, bacterial inflammation, familial Mediterranean fever, nephrotic syndrome, myocarditis, etc. Therefore, NLRP3 inhibitors have some therapeutic potential in these diseases with inflammatory pathological features.

SUMMARY

The present disclosure aims to provide a substituted heteroaryl phthalazine derivative having an NLRP3 inhibitory effect.

The present disclosure provides a compound of formula (1-0) or a pharmaceutically acceptable salt thereof:

(I-0)

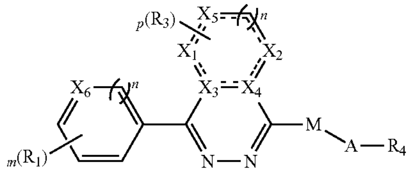

wherein:

n is 0 or 1;

m is an integer selected from 1 to 5;

p is selected from 1 or 2;

$X_1$, $X_2$, and $X_5$ are independently selected from $CH_2$, NH, CH, O, S, or N;

$X_3$ and $X_4$ are independently selected from $CH_2$, CH, or N;

$R_1$ is selected from hydrogen, deuterium, $C_{1-6}$ alkyl, $C_{1-6}$ alkoxy, $C_{3-6}$ cycloalkyl, halogen, phosphine oxide group, hydroxyl, or cyano, and the $C_{1-6}$ alkyl, $C_{3-6}$ cycloalkyl, $C_{1-6}$ alkoxy, or phosphine oxide group is optionally substituted by one or more halogens or $C_{1-3}$ alkyls, wherein m $R_1$ is the same or different from each other;

$R_3$ is selected from hydrogen, deuterium, $C_{1-6}$ alkyl, $C_{1-6}$ alkoxy, $C_{3-6}$ cycloalkyl, halogen, phosphine oxide group, carboxyl, or cyano, and the $C_{1-6}$ alkyl, $C_{3-6}$ alkoxy, $C_{3-6}$ cycloalkyl, or phosphine oxide group is optionally substituted by one or more halogens or $C_{1-3}$ alkyls, wherein p $R_3$ is the same or different from each other;

A is a single bond or $C_{1-3}$ alkylene chain, and optionally, one or more hydrogens on the methylene group in the $C_{1-3}$ alkylene chain are substituted by $C_{1-3}$ alkyls;

M is —$NR_{10}$—, —O—, or —S—;

$R_4$ is selected from $C_{1-6}$ alkyl, $C_{3-9}$ cycloalkyl, $C_{3-9}$ aryl, 3- to 9-membered heterocycloalkyl, 5- to 9-membered heteroaryl, or 9- to 12-membered partially unsaturated heterobicyclic group, and the $C_{1-6}$ alkyl, $C_{3-9}$ cycloalkyl, $C_{5-9}$ aryl, 3- to 9-membered heterocycloalkyl, 5- to 9-membered heteroaryl, or 9- to 12-membered partially unsaturated heterobicyclic group is optionally substituted by one or more halogens, hydroxyls. $C_{1-3}$ alkyls, $C_{1-6}$ acyls, =O, or —$NR_8R_9$; $R_8$, $R_9$, and $R_{10}$ are independently selected from hydrogen or $C_{1-3}$ alkyl.

Specifically, the present disclosure relates to a compound having a structure shown in formula (I) or a pharmaceutically acceptable salt thereof:

(I)

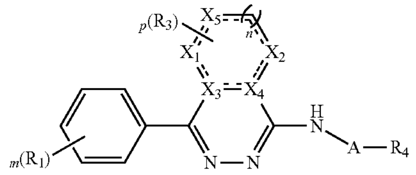

wherein:

n is 0 or 1;

m is an integer selected from 1 to 5;

p is selected from 1 or 2;

$X_1$, $X_2$, and $X_5$ are independently selected from $CH_2$, NH, CH, O, S, or N;

$X_3$ and $X_4$ are independently selected from $CH_2$, CH, or N;

$R_1$ is selected from hydrogen, deuterium, $C_{1-6}$ alkyl, $C_{1-6}$ alkoxy, $C_{3-6}$ cycloalkyl, halogen, phosphine oxide group, hydroxyl, or cyano, and the $C_{1-6}$ alkyl, $C_{3-6}$ cycloalkyl, $C_{1-6}$ alkoxy, or phosphine oxide group is optionally substituted by one or more halogens or $C_{1-3}$ alkyls, wherein m $R_1$ is the same or different from each other;

$R_3$ is selected from hydrogen, deuterium, $C_{1-6}$ alkyl, $C_{1-4}$ alkoxy, $C_{3-6}$ cycloalkyl, halogen, phosphine oxide group, carboxyl, or cyano, and the $C_{1-6}$ alkyl, $C_{1-6}$ alkoxy, $C_{3-6}$ cycloalkyl, or phosphine oxide group is optionally substituted by one or more halogens or $C_{1-3}$ alkyls, wherein p $R_3$ is the same or different from each other;

A is a single bond or $C_{1-3}$ alkylene chain, and optionally, one or more hydrogens on the methylene group in the $C_{1-3}$ alkylene chain are substituted by $C_{1-3}$ alkyls;

$R_4$ is selected from $C_{1-6}$ alkyl, $C_{3-9}$ cycloalkyl, $C_{5-9}$ aryl, 3- to 9-membered heterocycloalkyl, 5- to 9-membered heteroaryl, or 9- to 12-membered partially unsaturated heterobicyclic group, and the $C_{1-6}$ alkyl, $C_{3-9}$ cycloalkyl, $C_{5-9}$ aryl, 3- to 9-membered heterocycloalkyl, 5- to 9-membered heteroaryl, or 9- to 12-membered partially unsaturated heterobicyclic group is optionally substituted by one or more halogens, hydroxyls, $C_{1-3}$ alkyls, $C_{1-6}$ acyls, =O, or —$NR_8R_9$;

$R_8$ and $R_9$ are independently selected from hydrogen or $C_{1-3}$ alkyl.

Preferably, $R_4$ is selected from $C_{1-6}$ alkyl, $C_{3-9}$ cycloalkyl, $C_{5-9}$ aryl, 3- to 9-membered heterocycloalkyl, 5- to 9-membered heteroaryl, or 9- to 12-membered partially unsaturated heterobicyclic group, and the $C_{1-6}$ alkyl, $C_{3-9}$ cycloalkyl, $C_{5-9}$ aryl, 3- to 9-membered heterocycloalkyl, 5- to 9-membered heteroaryl, or 9- to 12-membered partially unsaturated heterobicyclic group is optionally substituted by one or more halogens, hydroxyls. $C_{1-3}$ alkyls, $C_{1-6}$ acyls, or —$NR_8R_9$.

Preferably, $R_1$ is selected from $C_{1-3}$ alkyl, $C_{1-3}$ alkoxy, $C_{3-6}$ cycloalkyl, phosphine oxide group, hydroxyl, cyano, or halogen, and the $C_{1-3}$ alkyl, $C_{1-3}$ alkoxy, $C_{3-6}$ cycloalkyl, or phosphine oxide group is optionally substituted by one to three halogens or $C_{1-3}$ alkyls.

Preferably, $R_1$ is selected from $C_{1-3}$ alkyl, $C_{1-3}$ alkoxy, hydroxyl, cyano, halogen, or phosphine oxide group, and the $C_{1-3}$ alkyl, $C_{1-3}$ alkoxy, or phosphine oxide group is optionally substituted by one to three fluorines or methyls.

Preferably, $R_1$ is selected from trifluoromethyl, difluoromethyl, methyl, fluorine, hydroxyl, dimethylphosphine oxide group, or trifluoromethoxy.

Preferably, $R_1$ is selected from trifluoromethyl, methyl, fluorine, hydroxyl, dimethylphosphine oxide group, or trifluoromethoxy.

Preferably, $R_1$ is selected from trifluoromethyl, methyl, or hydroxyl.

Preferably, $R_3$ is selected from hydrogen, $C_{1-3}$ alkyl, $C_{3-6}$ cycloalkyl, $C_{1-3}$ alkoxy, halogen, or phosphine oxide group, and the $C_{1-3}$ alkyl, $C_{1-3}$ alkoxy, $C_{3-6}$ cycloalkyl, or phosphine oxide group is optionally substituted by one to three halogens or $C_{1-3}$ alkyls.

Preferably, $R_3$ is selected from $C_{1-3}$ alkyl, $C_{1-3}$ alkoxy, $C_{3-6}$ cycloalkyl, or phosphine oxide group, and the $C_{1-3}$ alkyl, $C_{1-3}$ alkoxy, $C_{3-6}$ cycloalkyl, or phosphine oxide group is optionally substituted by one to three fluorines or methyls.

Preferably, $R_3$ is selected from hydrogen, methyl, methoxy, cyclopropyl, ethyl, fluorine, trifluoromethyl, or dimethylphosphine oxide group.

Preferably, $R_3$ is selected from hydrogen, methyl, or methoxy.

Preferably, A is a single bond or $C_{1-3}$ alkylene chain, and optionally, one or more hydrogens on the methylene group in the $C_{1-3}$ alkylene chain are substituted by methyls.

Preferably, A is a single bond, —$CH_2$—, —$(CH_3)CH$—, or —$CH_2CH_2$—.

Preferably, A is a single bond.

Preferably, $R_4$ is selected from $C_{1-6}$ alkyl, $C_{5-8}$ cycloalkyl, phenyl, 5- to 7-membered heterocycloalkyl containing 1-2 atoms independently selected from N, O, or S, 5- to 7-membered heteroaryl containing 1-2 atoms independently selected N, O, or S, or 9- to 12-membered partially unsaturated heterobicyclic group containing 1-2 atoms independently selected N, O, or S. and the $C_{1-6}$ alkyl, $C_{5-8}$ cycloalkyl, phenyl, 5- to 7-membered heterocycloalkyl containing 1-2 atoms independently selected from N, O, or S, 5- to 7-membered heteroaryl containing 1-2 atoms independently selected N, O, or S, or 9- to 12-membered partially unsaturated heterobicyclic group containing 1-2 atoms independently selected N, O, or S is optionally substituted by one or more halogens, hydroxyls, $C_{1-3}$ alkyls, $C_{1-6}$ acyls, halogenated $C_{1-3}$ alkyls, =O, or —$NR_8R_9$.

Preferably, $R_4$ is selected from $C_{1-6}$ alkyl, $C_{5-8}$ cycloalkyl, phenyl, 5- to 7-membered heterocycloalkyl containing 1-2 atoms independently selected from N, O, or S, 5- to 7-membered heteroaryl containing 1-2 atoms independently selected N, O, or S, or 9- to 12-membered partially unsaturated heterobicyclic group containing 1-2 atoms independently selected N, O, or S, and the $C_{1-6}$ alkyl, $C_{5-8}$ cycloalkyl, phenyl, 5- to 7-membered heterocycloalkyl containing 1-2 atoms independently selected from N, O, or S, 5- to 7-membered heteroaryl containing 1-2 atoms independently selected N, O, or S, or 9- to 12-membered partially unsaturated heterobicyclic group containing 1-2 atoms independently selected N, O, or S is optionally substituted by one or more halogens, hydroxyls, $C_{1-3}$ alkyls, $C_{1-6}$ acyls, or —$NR_8R_9$.

Preferably, $R_4$ is selected from $C_{1-6}$ alkyl, $C_{5-8}$ cycloalkyl, phenyl, 5- to 7-membered heterocycloalkyl containing 1-2 atoms independently selected from N or O, 5- to 7-membered heteroaryl containing 1 N atom, or 9- to 12-membered partially unsaturated heterobicyclic group containing 1 N atom, and the $C_{1-6}$ alkyl, $C_{5-8}$ cycloalkyl, phenyl, 5- to 7-membered heterocycloalkyl containing 1-2 atoms independently selected from N or O, 5- to 7-membered heteroaryl containing 1 N atom, or 9- to 12-membered partially unsaturated heterobicyclic group containing 1 N atom is optionally substituted by one or more halogens, hydroxyls, $C_{1-3}$ alkyls, $C_{1-6}$ acyls, halogenated $C_{1-3}$ alkyls, =O, or —$NR_8R_9$.

Preferably, $R_4$ is selected from $C_{1-6}$ alkyl, $C_{5-8}$ cycloalkyl, phenyl, 5- to 7-membered heterocycloalkyl containing 1-2 atoms independently selected from N or O, 5- to 7-membered heteroaryl containing 1 N atom, or 9- to 12-membered partially unsaturated heterobicyclic group containing 1 N atom, and the $C_{1-6}$ alkyl, $C_{5-8}$ cycloalkyl, phenyl, 5- to 7-membered heterocycloalkyl containing 1-2 atoms independently selected from N or O, 5- to 7-membered heteroaryl containing 1 N atom, or 9- to 12-membered partially unsaturated heterobicyclic group containing 1 N atom is optionally substituted by one or more halogens, hydroxyls, $C_{1-3}$ alkyls, $C_{1-6}$ acyls, or —$NR_8R_9$.

Preferably, $R_4$ is selected from n-butyl, cyclohexyl, phenyl, piperidyl, pyridyl, pyrrolyl, pyrrolidinyl, morpholinyl, tetrahydropyranyl,

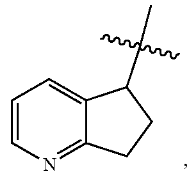
, or
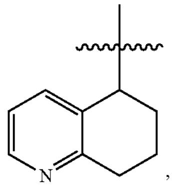
, and the cyclohexyl, phenyl, piperidyl, pyridyl, pyrrolyl, or pyrrolidinyl is optionally substituted by one or more halogens, hydroxyls, $C_{1-3}$ alkyls, $C_{1-6}$ acyls, halogenated $C_{1-3}$ alkyls, =O, or —$NR_8R_9$.

Preferably, $R_4$ is selected from n-butyl, cyclohexyl, phenyl, piperidyl, pyridyl, pyrrolyl, pyrrolidinyl, morpholinyl, or

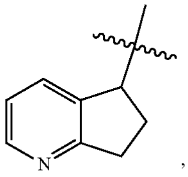 [SMILES: *C1CCc2ncccc21]
, and the cyclohexyl, phenyl, piperidyl, pyridyl, pyrrolyl, or pyrrolidinyl is optionally substituted by one or more halogens, hydroxyls, $C_{1-3}$ alkyls. $C_{1-6}$ acyls, or —$NR_8R_9$.

Preferably, $R_4$ is selected from n-butyl, cyclohexyl, phenyl, piperidyl, pyridyl, pyrrolidinyl, morpholinyl, tetrahydropyranyl,

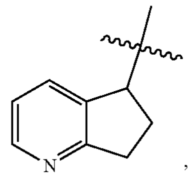
, or
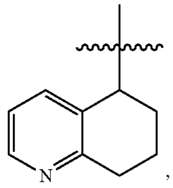
, and the cyclohexyl, phenyl, piperidyl, pyridyl, or pyrrolidinyl is optionally substituted by one to two fluorines, hydroxyls, methyls, ethyls, acetyls, halogenated $C_{1-3}$ alkyls, =O, or —$N(CH_3)_2$.

Preferably, $R_4$ is selected from n-butyl, cyclohexyl, phenyl, piperidyl, pyridyl, pyrrolidinyl, morpholinyl, or

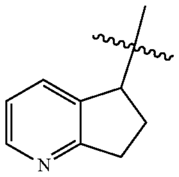
, and the cyclohexyl, phenyl, piperidyl, pyridyl, or pyrrolidinyl is optionally substituted by one to two fluorines, hydroxyls, methyls, ethyls, acetyls, or —$N(CH_3)_2$.

Preferably, $R_4$ is selected from n-butyl, —$C(CH_3)_2OH$, phenyl,

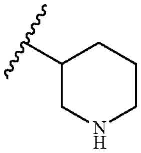, 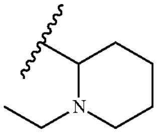, 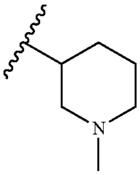, 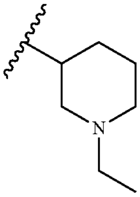, 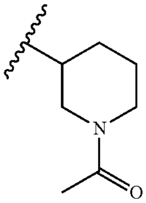, 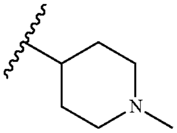, 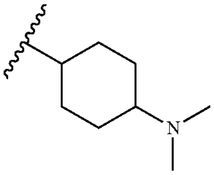, 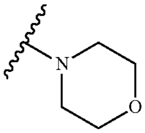, 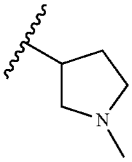, 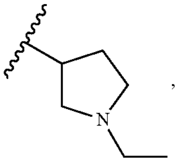, 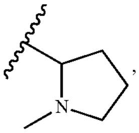, 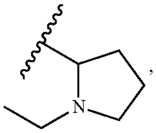, 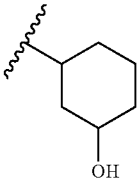, 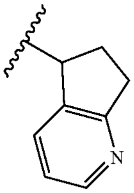, 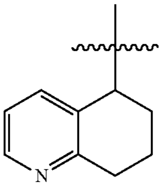, 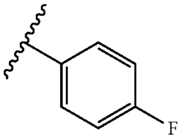, 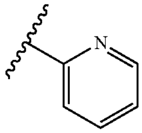, 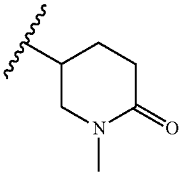, 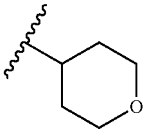, or 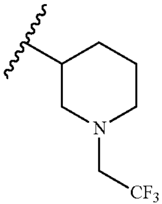.
Preferably, $R_4$ is selected from n-butyl, —$C(CH_3)_2OH$, phenyl.
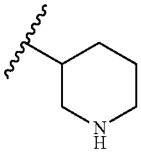, 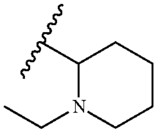, 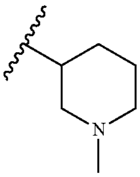,
-continued
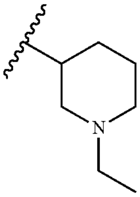, 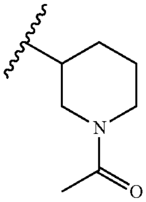, 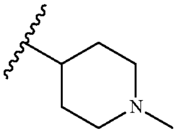, 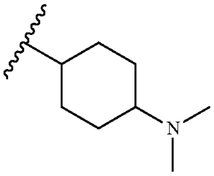, 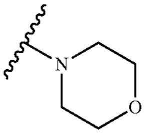, 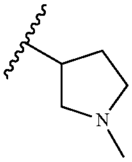, 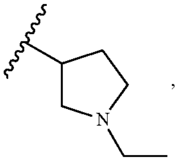, 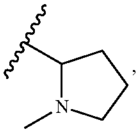, 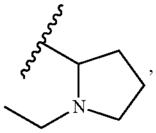, 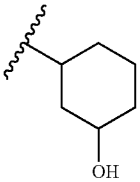, 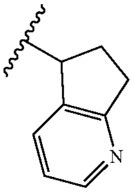, 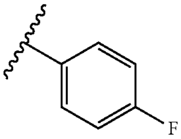, or 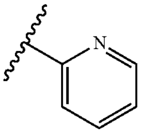.
Preferably, $R_4$ is selected from
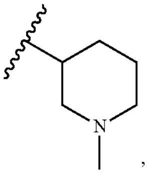, 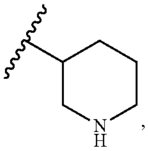, 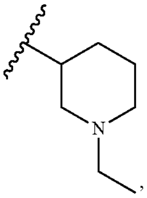, 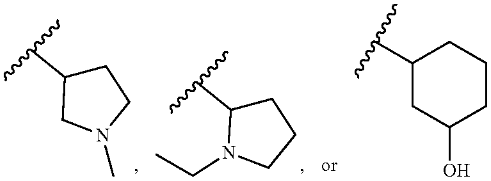.
Preferably, $R_8$ and $R_9$ are methyls.
The present disclosure relates to a compound having a structure shown in formula (II) or a pharmaceutically acceptable salt thereof:

(II)

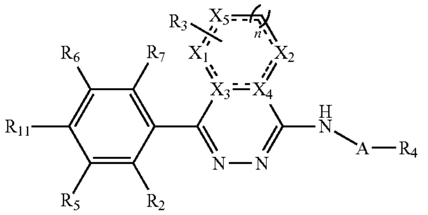

wherein:

n, $X_1$, $X_2$, $X_3$, $X_4$, $X_5$, $R_3$, $R_4$, and A are defined as above.

Preferably, $R_{11}$ is selected from hydrogen, deuterium, $C_{1-6}$ alkyl, $C_{1-6}$alkoxy, $C_{3-6}$ cycloalkyl, halogen, or phosphine oxide group, and the $C_{1-6}$ alkyl, $C_{3-6}$ cycloalkyl, $C_{1-6}$ alkoxy, or phosphine oxide group is optionally substituted by one or more halogens or $C_{1-3}$ alkyls.

Preferably, $R_{11}$ is selected from hydrogen. $C_{1-3}$ alkyl, $C_{1-3}$ alkoxy, phosphine oxide group, halogen, or $C_{34}$ cycloalkyl, and the $C_{1-3}$ alkyl, $C_{1-3}$ alkoxy, $C_{3-6}$ cycloalkyl, or phosphine oxide group is optionally substituted by one to three halogens or $C_{1-3}$ alkyls.

Preferably, $R_n$ is selected from hydrogen, $C_{1-3}$ alkyl, $C_{1-3}$ alkoxy, halogen, or phosphine oxide group, and the $C_{1-3}$ alkyl, $C_{1-3}$ alkoxy, or phosphine oxide group is optionally substituted by one to three fluorines or methyls.

Preferably, $R_{11}$ is selected from hydrogen, trifluoromethyl, methyl, fluorine, dimethylphosphine oxide group, or trifluoromethoxy.

Preferably, $R_{11}$ is selected from trifluoromethyl, methyl, trifluoromethoxy, or fluorine.

$R_2$ is selected from hydrogen, deuterium, $C_{1-6}$ alkyl, hydroxyl, halogen, cyano, or difluoromethyl.

Preferably, $R_2$ is selected from hydrogen, deuterium, $C_{1-6}$ alkyl, hydroxyl, halogen, or cyano.

Preferably, $R_2$ is selected from hydroxyl or difluoromethyl.

Preferably, $R_2$ is selected from hydroxyl.

$R_5$, $R_6$, and $R_7$ are independently selected from hydrogen, halogen, or $C_{1-3}$ alkyl.

Preferably, $R_5$, $R_6$, and $R_7$ are independently selected from hydrogen, fluorine, or methyl.

The present disclosure relates to a compound having a structure shown in formula (III) or a pharmaceutically acceptable salt thereof:

(III)

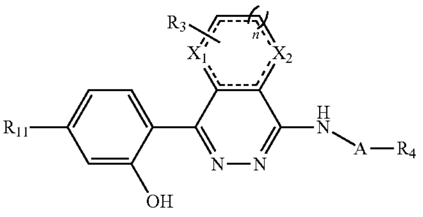

wherein:

n, $X_1$. $X_2$, $R_{11}$, $R_3$, $R_4$, and A are defined as above.

The present disclosure relates to a compound having a structure shown in formula (IV) or a pharmaceutically acceptable salt thereof:

(IV)

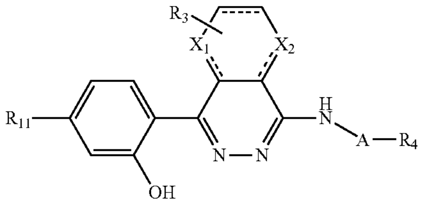

wherein:

$X_1$, $X_2$, $R_{11}$, $R_3$, $R_4$, and A are defined as above.

The present disclosure relates to a compound having a structure shown in formula (IVa), (IVb), (IVc), (IVd), or (IVe) or a pharmaceutically acceptable salt thereof:

(IVa)

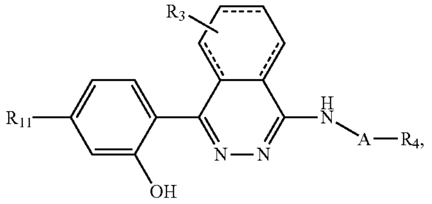

(IVb)

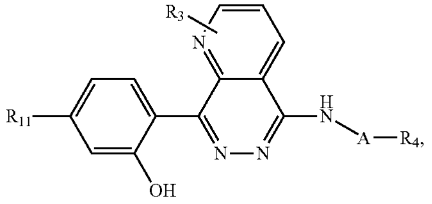

(IVc)

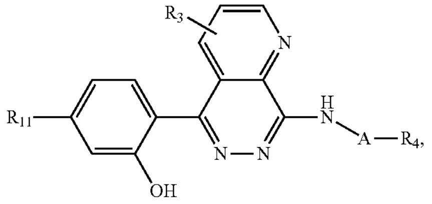

(IVd)

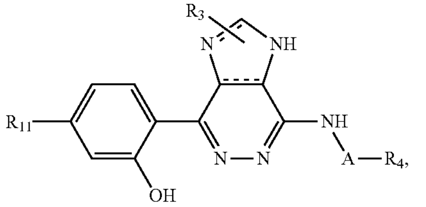

or (IVe)

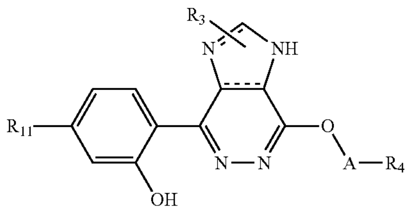

wherein:

$R_1$, $R_3$, $R_4$, and A are defined as above.

The present disclosure further relates to a compound having a structure shown in formula (V) or formula (VI) or a pharmaceutically acceptable salt thereof:

(V)

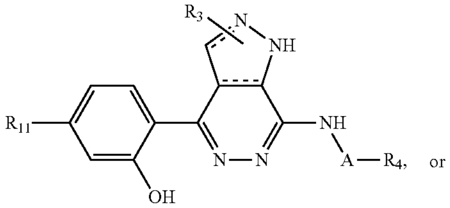

or (VI)

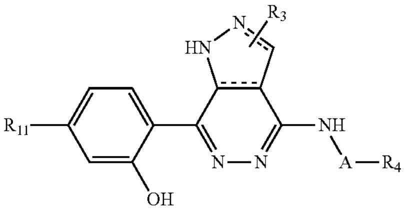

wherein:

$R_3$, $R_4$, and A are defined as above.

The present disclosure relates to a compound having a structure shown in formula (I-1) or a pharmaceutically acceptable salt thereof:

(I-1)

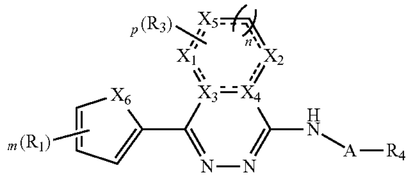

wherein:

is n is 0 or 1;

m is an integer selected from 1 to 5;

p is selected from 1 or 2;

$X_1$, $X_2$, $X_5$, and $X_6$ are independently selected from $CH_2$, NH, CH, O, S, or N;

$X_3$ and $X_4$ are independently selected from $CH_2$, CH, or N;

$R_1$ is selected from hydrogen, deuterium. $C_{1-6}$ alkyl, $C_{1-6}$ alkoxy, $C_{3-6}$ cycloalkyl, halogen, phosphine oxide group, hydroxyl, or cyano, and the $C_{1-6}$ alkyl, $C_{3-6}$ cycloalkyl, $C_{1-6}$ alkoxy, or phosphine oxide group is optionally substituted by one or more halogens or $C_{1-3}$ alkyls, wherein m $R_1$ is the same or different from each other, $R_3$ is selected from hydrogen, deuterium, $C_{1-6}$ alkyl, $C_{1-6}$ alkoxy, $C_{3-6}$ cycloalkyl, halogen, phosphine oxide group, carboxyl, or cyano, and the $C_{1-6}$ alkyl, $C_{1-6}$ alkoxy, $C_{3-6}$ cycloalkyl, or phosphine oxide group is optionally substituted by one or more halogens or $C_{1-3}$ alkyls, wherein p $R_3$ is the same or different from each other;

A is a single bond or $C_{1-3}$ alkylene chain, and optionally, one or more hydrogens on the methylene group in the $C_{1-3}$ alkylene chain are substituted by $C_{1-3}$ alkyls;

$R_4$ is selected from $C_{1-6}$ alkyl, $C_{3-9}$ cycloalkyl, $C_{5-9}$ aryl, 3- to 9-membered heterocycloalkyl, 5- to 9-membered heteroaryl, or 9- to 12-membered partially unsaturated heterobicyclic group, and the $C_{1-6}$ alkyl, $C_{3-9}$ cycloalkyl, $C_{3-9}$ aryl, 3- to 9-membered heterocycloalkyl, 5- to 9-membered heteroaryl, or 9- to 12-membered partially unsaturated heterobicyclic group is optionally substituted by one or more halogens, hydroxyls. Ct-3 alkyls, $C_{1-6}$ acyls, =O, or —$NR_8R_9$;

$R_8$ and $R_9$ are independently selected from hydrogen or $C_{1-3}$ alkyl;

preferably, $X_6$ is selected from S.

The present disclosure relates to the following compounds or pharmaceutically acceptable salts thereof:

1

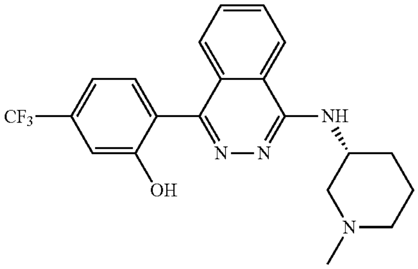

2

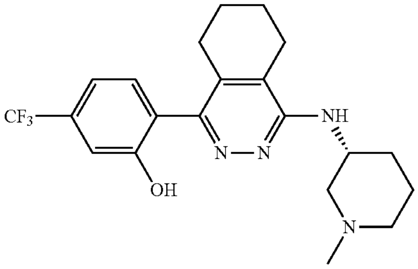

3

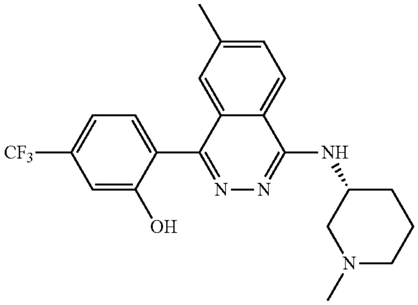

4

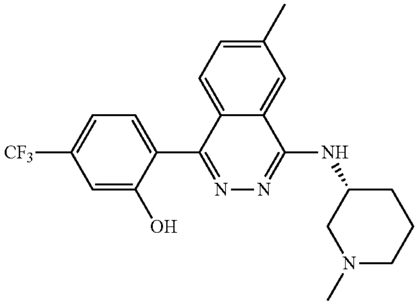

-continued
5
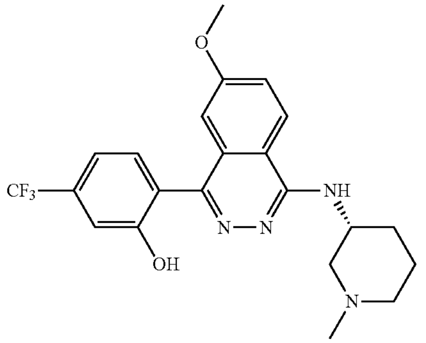
6
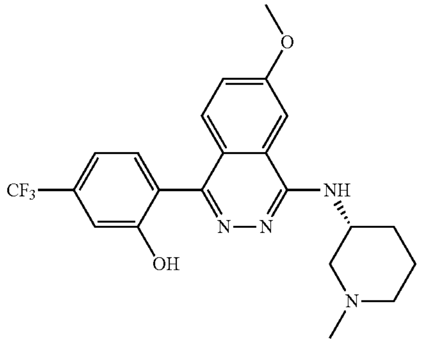
7
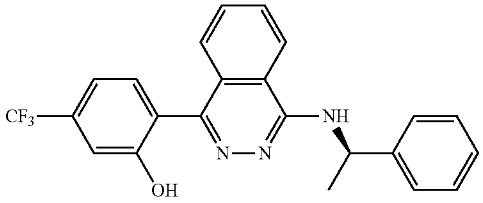
8
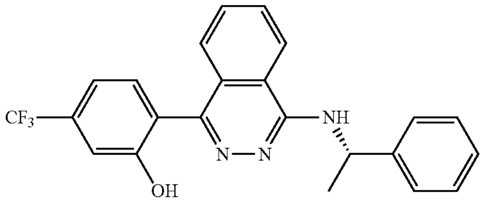
9
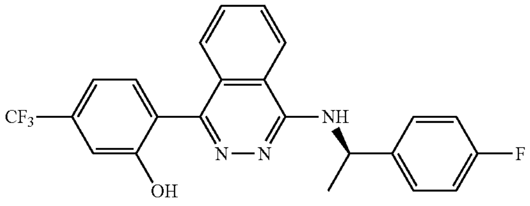
10
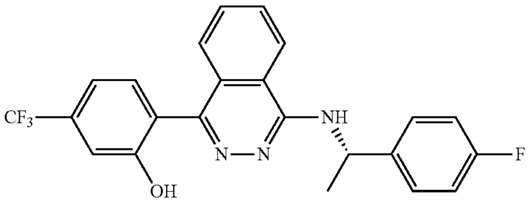
-continued
11
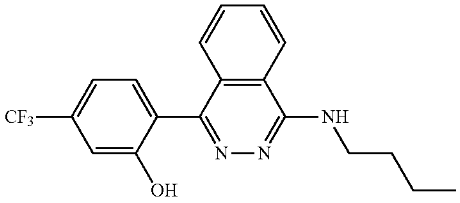
12
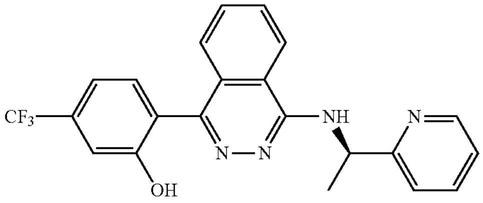
13
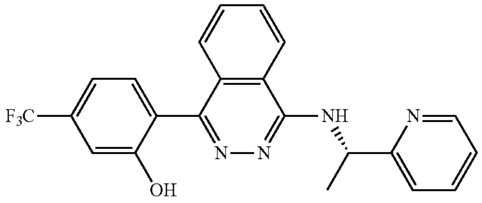
14
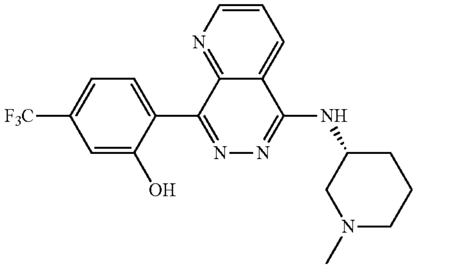
15
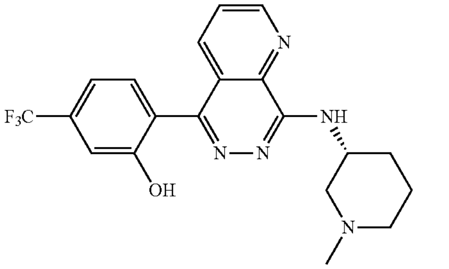
16
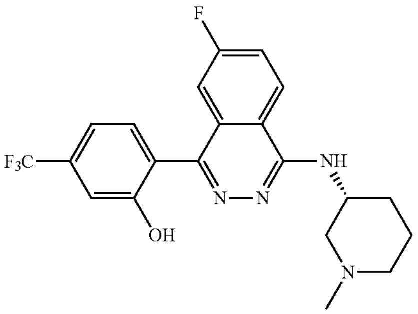

-continued
17
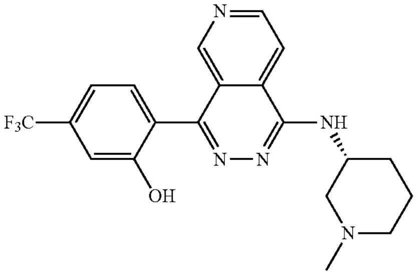
18
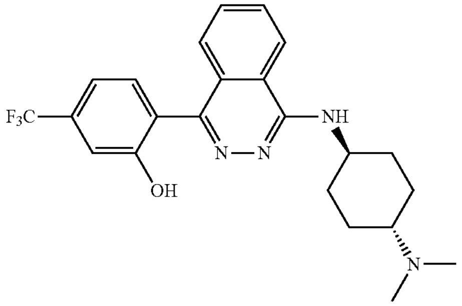
19
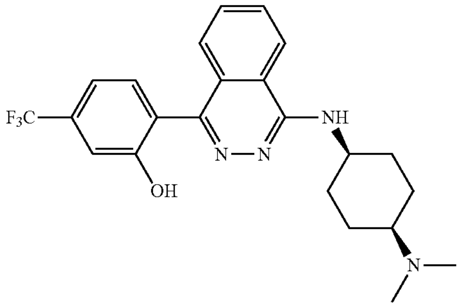
20
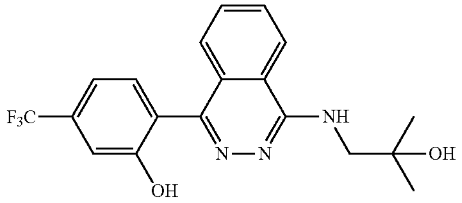
21
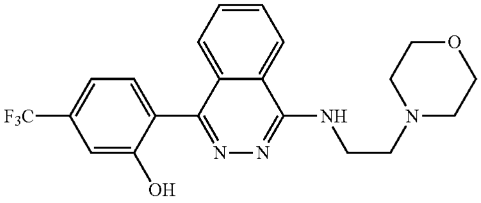
22
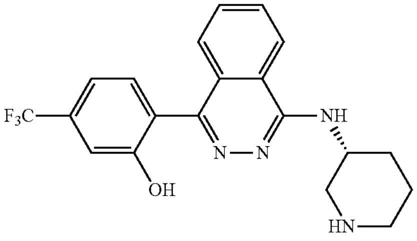
-continued
23
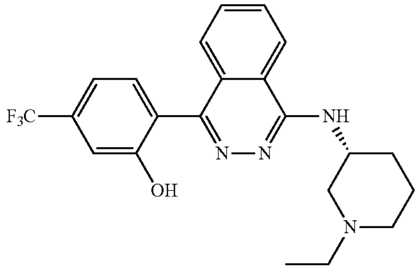
24
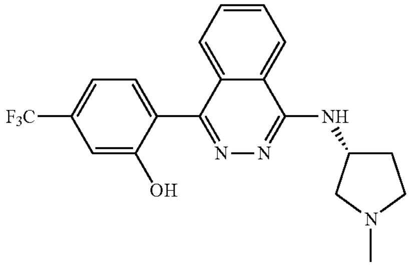
25
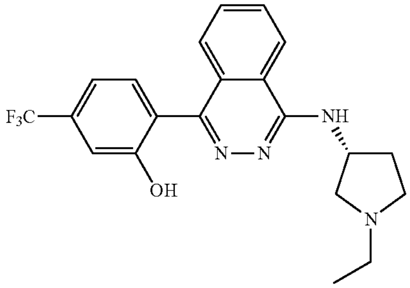
26
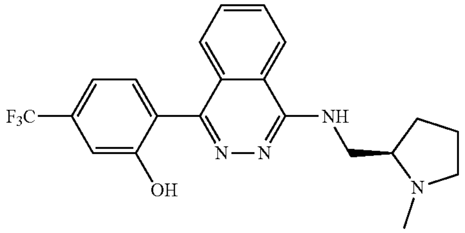
27
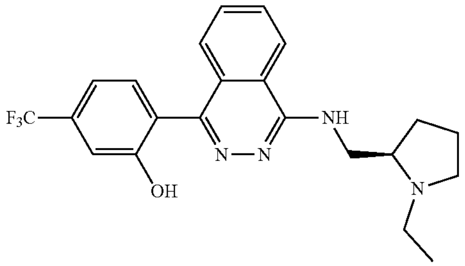
28
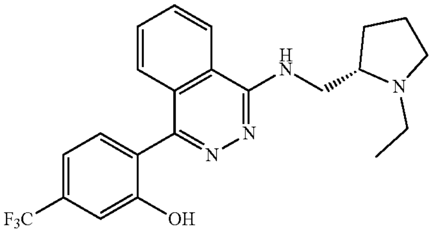

-continued
29
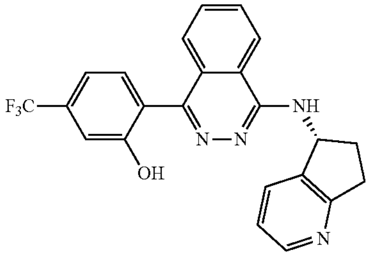
30
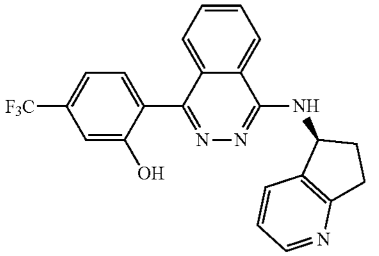
31
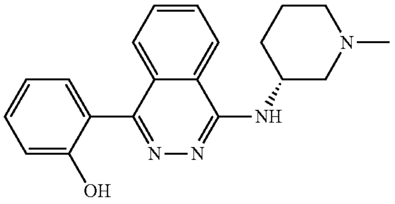
32
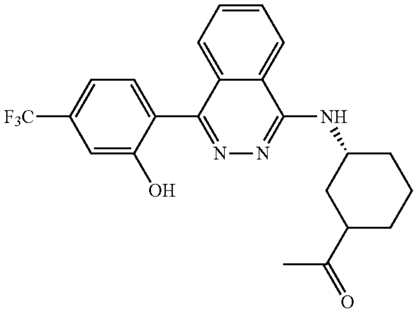
33
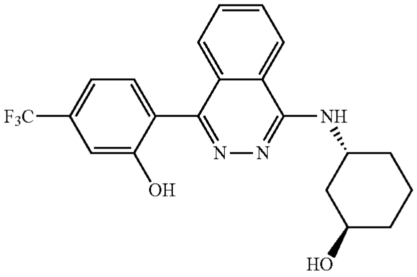
34
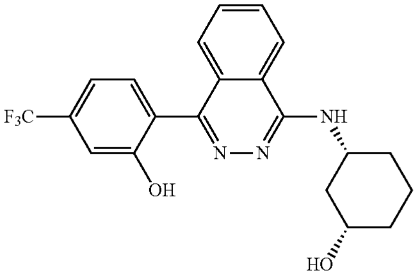
-continued
35
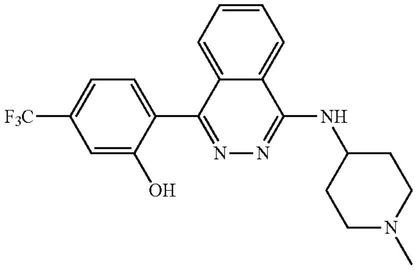
36
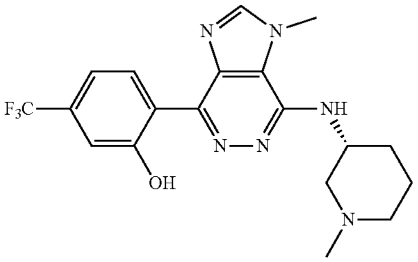
37
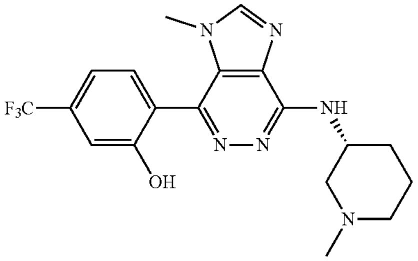
38
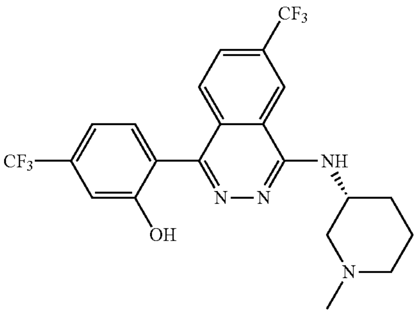
39
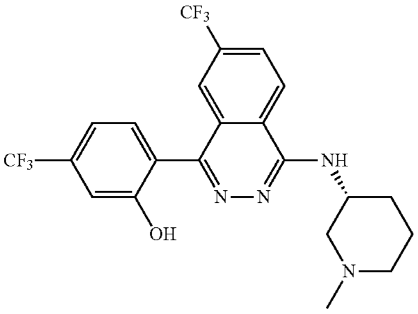

-continued
40
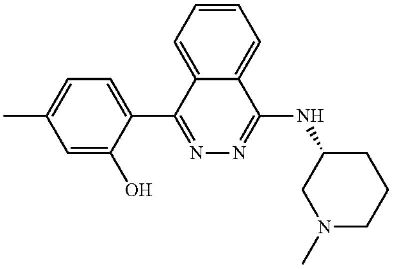
41
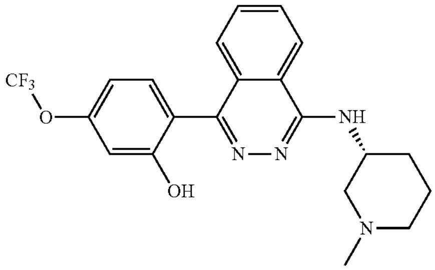
43
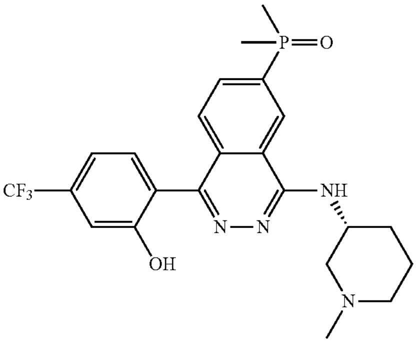
44
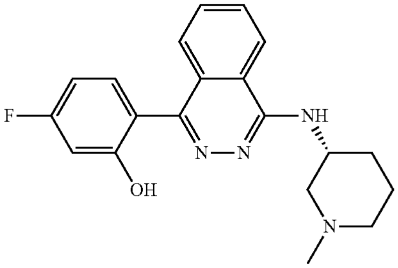
45
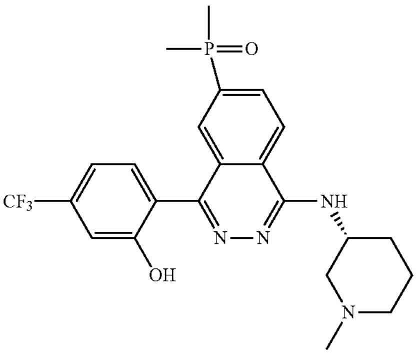
-continued
46
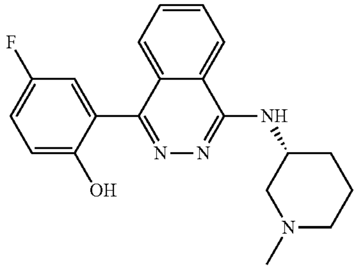
47
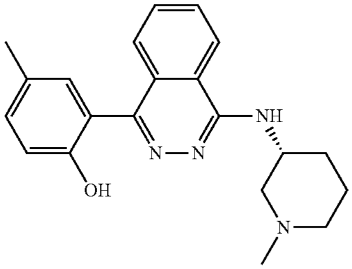
48
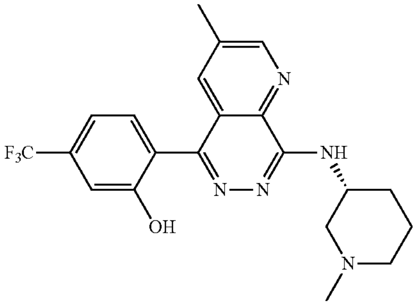
49
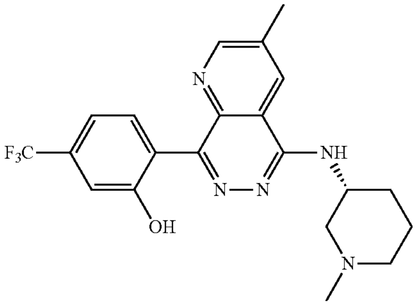
50
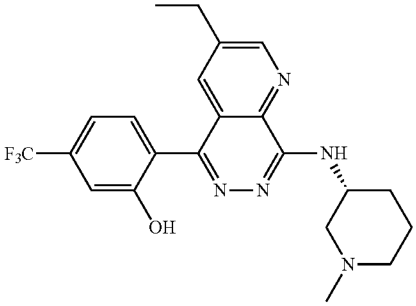

-continued
51
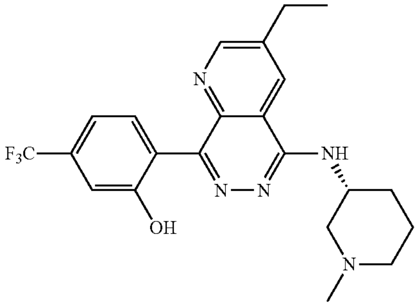
52
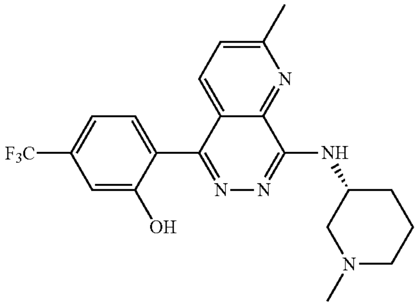
53
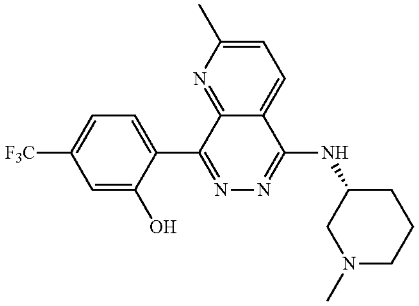
54
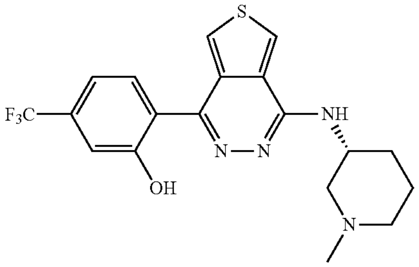
55
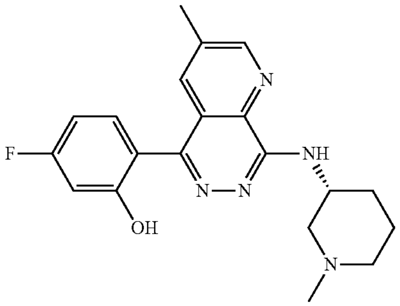
-continued
56
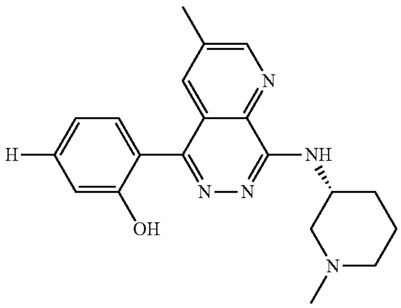
57
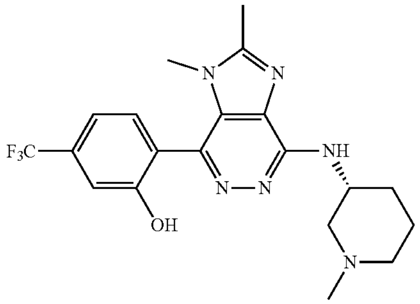
58
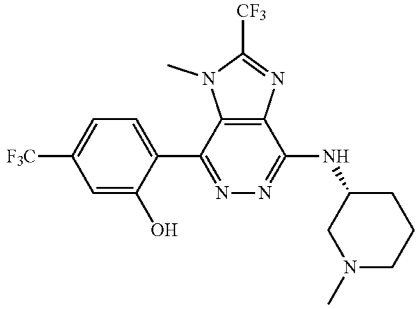
59
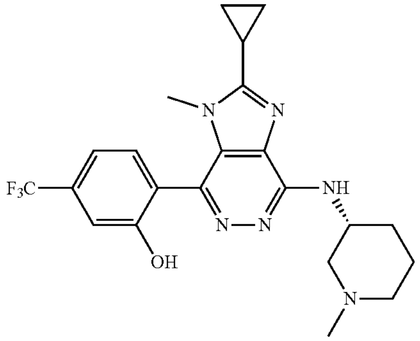
60
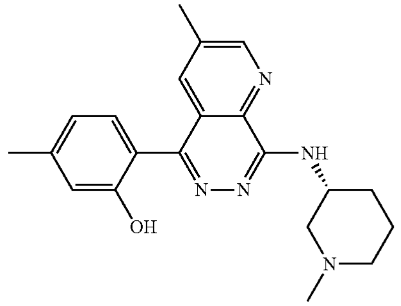

61
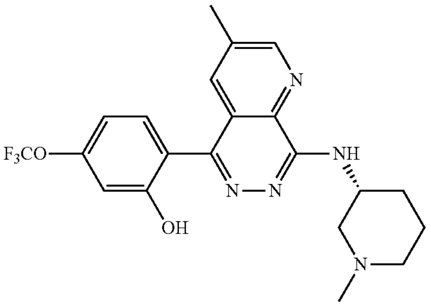
62
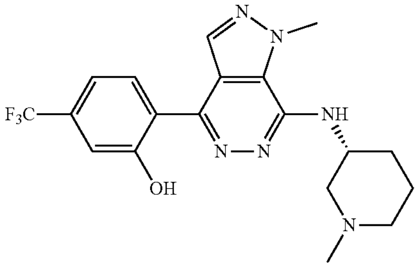
63
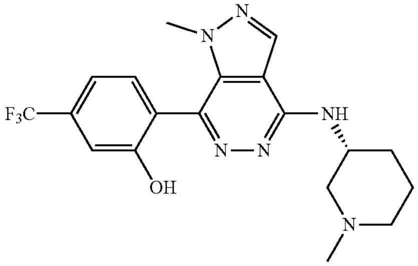
64
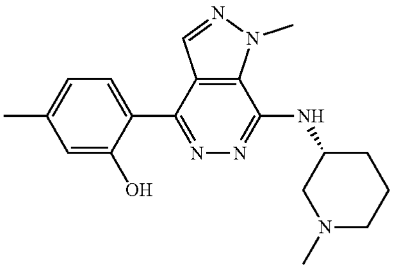
65
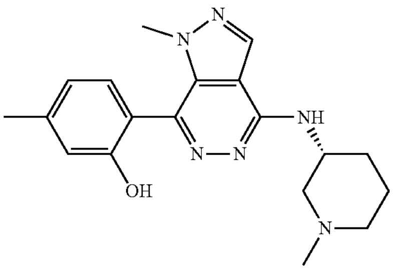
66
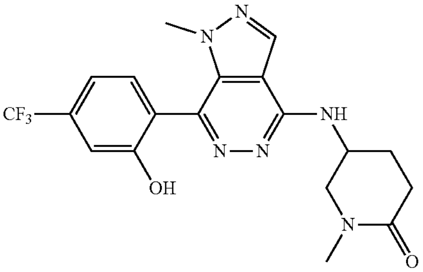
67
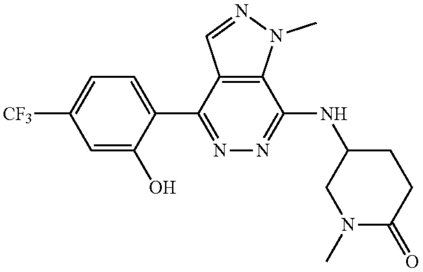
68
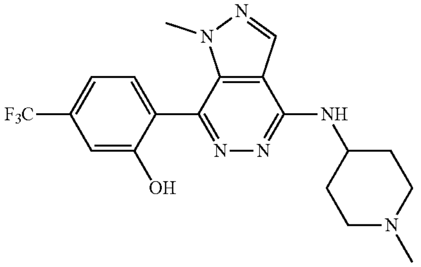
69
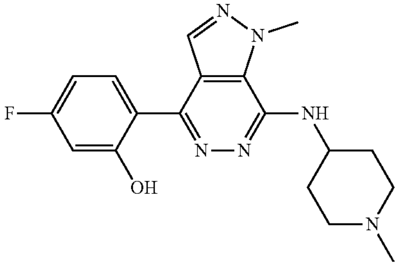
70
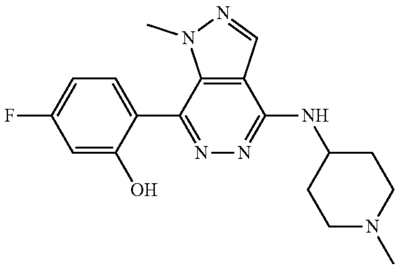
71
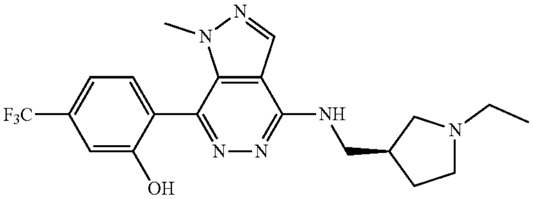

72
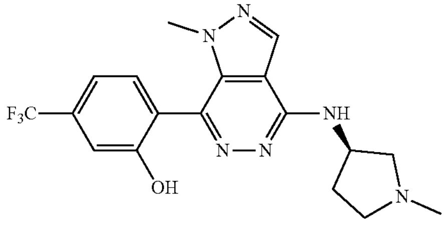
73
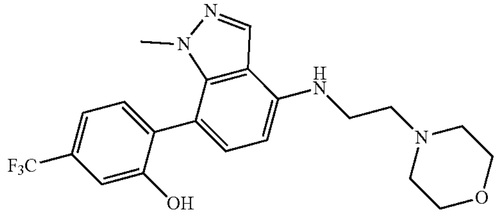
74
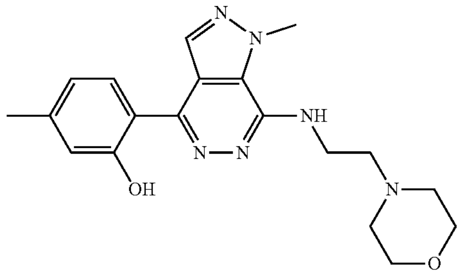
75
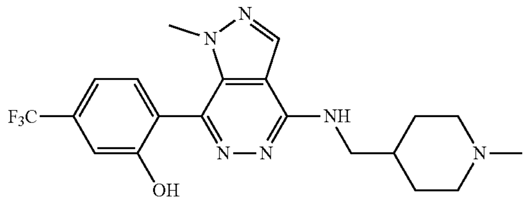
76
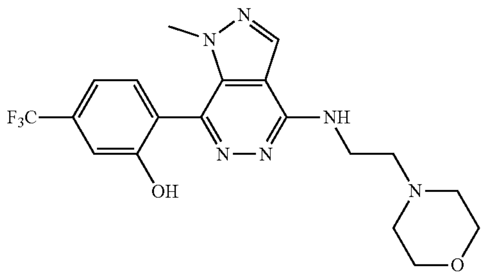
77
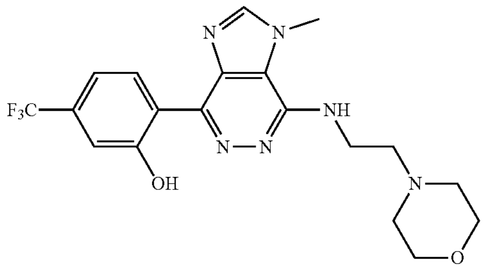
78
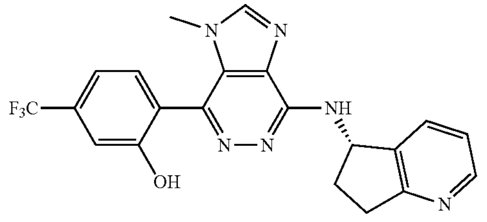
79
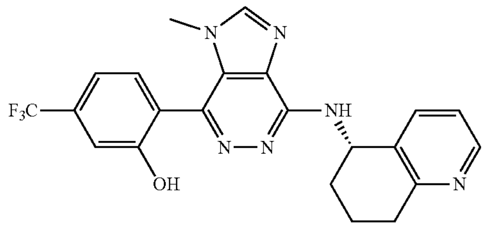
80
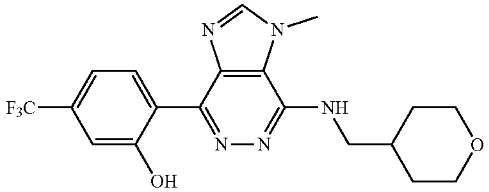
81
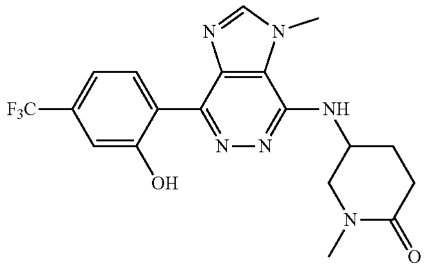
82
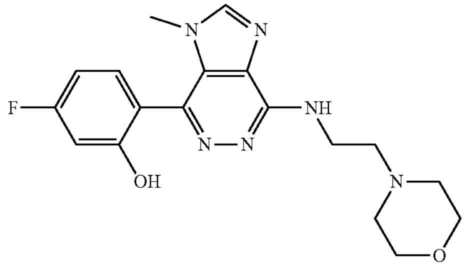
83
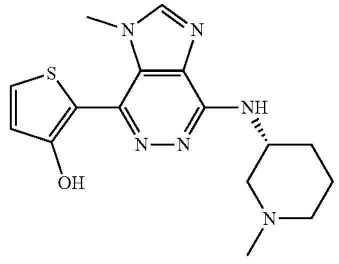

-continued

84

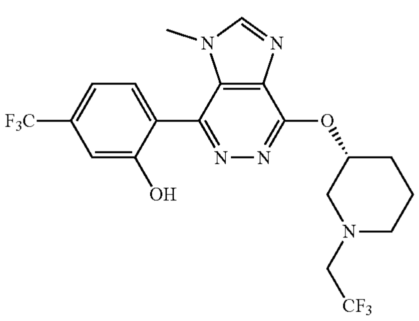

85

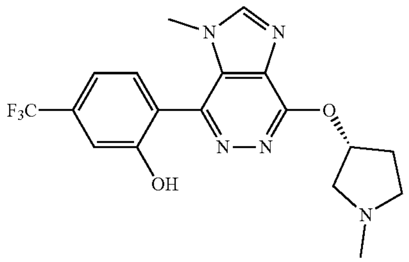

86

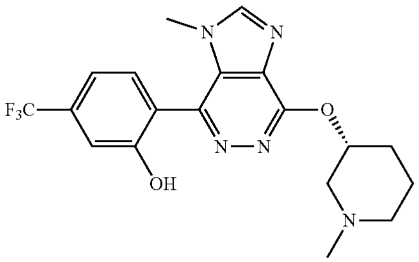

87

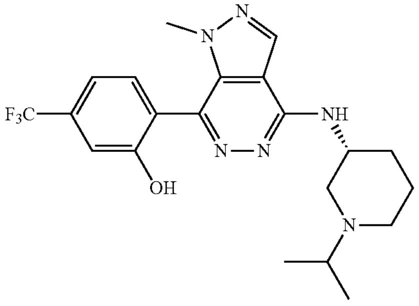

88

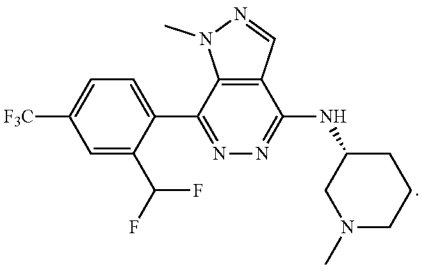

The present disclosure relates to a preparation method for the above-referenced compound or a pharmaceutically acceptable salt thereof, including the following steps:

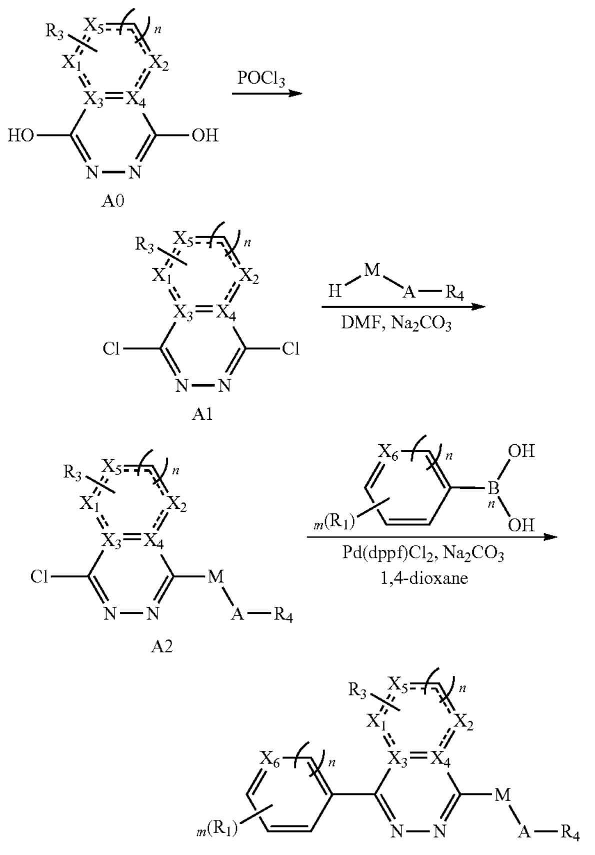

A0

A1

A2

I-0 step 1: dissolving a compound A0 in $POCl_3$, heating to 100 °C for reacting overnight, determining complete reaction by TLC, concentrating the reaction solution directly, removing the $POCl_3$, then slowly adding the oily crude product dropwise to ice water, extracting with ethyl acetate, and separating by column chromatography to obtain a target compound A1;

step 2: dissolving the compound A1, a corresponding amine, and $Na_2CO_3$ in dry DMF, heating to the mixed system in a sealed tube to 120 °C for reacting overnight, determining complete conversion of the raw materials by TLC, adding the reaction solution to water, extracting with ethyl acetate, and separating by column chromatography to obtain a target compound A2;

step 3: adding the compound A2, boric acid, sodium carbonate, and $Pd(dppf)Cl_2$ to a mixed solvent of dioxane and water, displacing with nitrogen 3 times, and heating to 110 °C for reacting for 3 hours, adding the reaction solution to water, extracting with ethyl acetate, and separating by column chromatography to obtain a target compound I-0.

In an embodiment, the method includes the following steps:

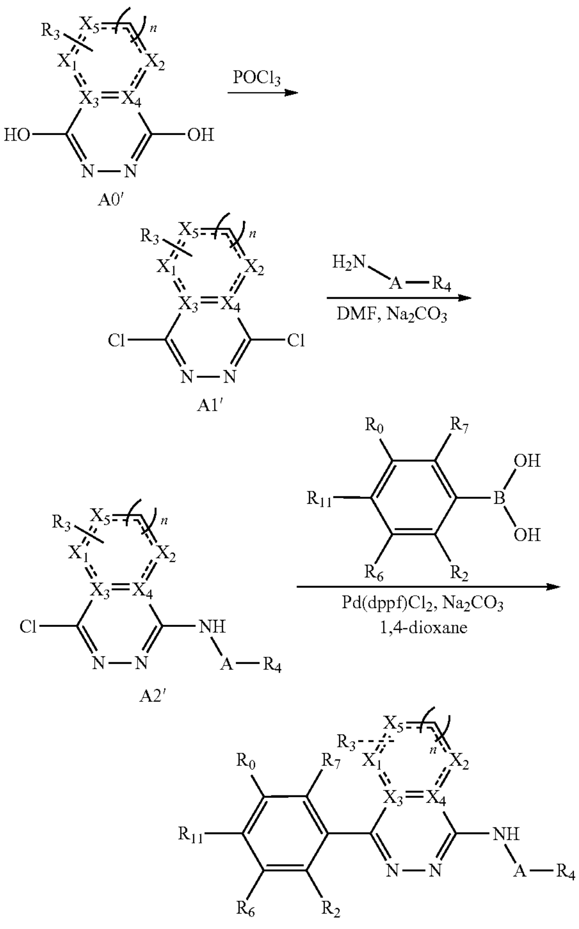

A0'

A1'

A2'

II step 1: dissolving a compound A0' in $POCl_3$, heating to 100 °C for reacting overnight, determining complete reaction by TLC, concentrating the reaction solution directly, removing the $POCl_3$, then slowly adding the oily crude product dropwise to ice water, extracting with ethyl acetate, and separating by column chromatography to obtain a target compound A1';

step 2: dissolving the compound A1', a corresponding amine, and $Na_2CO_3$ in dry DMF, heating the mixed system in a sealed tube to 120 °C for reacting overnight, determining complete conversion of the raw materials by TLC, adding the reaction solution to water, extracting with ethyl acetate, and separating by column chromatography to obtain a target compound A2';

step 3: adding the compound A2', boric acid, sodium carbonate, and $Pd(dppf)Cl_2$ to a mixed solvent of dioxane and water, displacing with nitrogen 3 times, and heating to 110 °C for reacting for 3 hours, adding the reaction solution to water, extracting with ethyl acetate, and separating by column chromatography to obtain a target compound II.

Another aspect of the present disclosure provides a stereoisomer, solvate, or prodrug of any of the above-referenced compounds.

The present disclosure relates to a pharmaceutical composition, including any of the above-referenced compounds or pharmaceutically acceptable salts thereof and pharmaceutically acceptable excipients.

The present disclosure relates to a use of any of the above-referenced compounds or pharmaceutically acceptable salts thereof or the above-referenced pharmaceutical composition in preparation of a drug for treating an NLRP3 mediated disease.

The present disclosure relates to a use of any of the above-referenced compounds or pharmaceutically acceptable salts thereof or the above-referenced pharmaceutical composition in preparation of an NLRP3 inhibitor.

The present disclosure relates to a method for inhibiting NLRP3 in a patient in need, including administering, to the patient, any of the above-referenced compounds or pharmaceutically acceptable salts thereof or the above-referenced pharmaceutical composition.

The present disclosure relates to a method for treating an NLRP3 mediated disease of a patient in need, including administering, to the patient, any of the above-referenced compounds or pharmaceutically acceptable salts thereof or the above-referenced pharmaceutical composition, and preferably, the NLRP3 mediated disease includes but is not limited to rheumatoid arthritis, gouty arthritis, atherosclerosis, myocardial infarction, Parkinson's syndrome, Alzheimer's disease, infectious lung injury, pulmonary fibrosis, sepsis, ulcerative colitis, type II diabetes, sepsis, bacterial inflammation, familial Mediterranean fever, nephrotic syndrome, and myocarditis.

Another aspect of the present disclosure provides a use of an NLRP3 inhibitor containing any of the above-referenced compounds or pharmaceutically acceptable salts thereof or the pharmaceutical composition in treatment of heart diseases.

Another aspect of the present disclosure provides a use of an NLRP3 inhibitor containing any of the above-referenced compounds or pharmaceutically acceptable salts thereof or the pharmaceutical composition in treatment of inflammatory diseases.

Another aspect of the present disclosure provides a use of an NLRP3 inhibitor containing any of the above-referenced compounds or pharmaceutically acceptable salts thereof or the pharmaceutical composition in treatment of infectious diseases.

The compounds of the present disclosure have NLRP3 inhibitory effects.

DETAILED DESCRIPTION

I. Definition

Based on the above content of the present disclosure, various other forms of modifications, replacements, or changes may be made in accordance with common technical knowledge and customary means in the art, without departing from the basic technical idea of the present disclosure.

The term "include" or its transformations such as "included" or "including" will be understood to include the stated elements or components throughout the specification and claims, and does not exclude other elements or components, unless otherwise expressly stated.

Compounds in the present disclosure may be asymmetric, for example, having one or more stereoisomers. Unless otherwise specified, all stereoisomers include enantiomers and diastereoisomers. The compounds containing asymmetric carbon atoms in the present disclosure may be isolated in an optically active pure form or racemic form. The optically active pure form may be split from racemic mixtures or synthesized using chiral raw materials or chiral reagents.

Racemes, diastereoisomers, and enantiomers are all included within the scope of the present disclosure.

In the present disclosure,

“”

refers to a substituent bonding position.

In the present disclosure, a numerical range refers to each integer within a given range. For example, “C1-6” indicates that a group may have 1 carbon atom, 2 carbon atoms, 3 carbon atoms, 4 carbon atoms, 5 carbon atoms, or 6 carbon atoms; “C1-3” indicates that a group may have 1 carbon atom, 2 carbon atoms, or 3 carbon atoms.

The term “optional” or “optionally” indicates that a subsequently described event or situation may or may not occur, including the occurrence and non-occurrence of the event or situation.

The term “substituted by” or “substitute” indicates that a specific atom or any one or more hydrogen atoms on a group are substituted by a substituent(s), as long as the valence state of the specific atom or group is normal and the substituted compound is stable. When the substituent is a ketone group (i.e., =O), it means that two hydrogen atoms are substituted. Unless otherwise specified, the type and number of substituents may be arbitrary on the basis of chemical feasibility.

The substituents may be selected from but not limited to one, two, or more of the following substituents: deuterium, halogen group, cyano, nitro, —C(=O)R, —C(=O)OR', —OC(=O)R", imido, amido, hydroxyl, substituted or unsubstituted amino, substituted or unsubstituted alkyl, substituted or unsubstituted cycloalkyl, substituted or unsubstituted haloalkyl, substituted or unsubstituted alkoxy, substituted or unsubstituted alkenyl, substituted or unsubstituted alkynyl, substituted or unsubstituted aryl, substituted or unsubstituted aryloxy, substituted or unsubstituted heteroaryl, etc.

When any variable (such as R″) appears more than once in the composition or structure of a compound, its definition in each case is independent. Therefore, for example, if a group is substituted by one to three Rs, the group may be optionally substituted by up to three Rs, and the R has an independent option in each case. In addition, combinations of substituents and/or variants thereof are allowed only if such combinations produce stable compounds.

The term “alkyl” refers to a saturated aliphatic hydrocarbon group, including linear or branched saturated hydrocarbon groups with indicated number of carbon atoms. For example, the term “$C_{1-6}$ alkyl” includes $C_1$ alkyl, $C_2$ alkyl, $C_3$ alkyl, $C_4$ alkyl, $C_5$ alkyl, and $C_6$ alkyl, and examples include, but are not limited to, methyl, ethyl, n-propyl, isopropyl, n-butyl, isobutyl, tert-butyl, n-pentyl, 2-pentyl, 3-pentyl, n-hexyl, 2-hexyl, 3-hexyl, etc. The alkyl may be divalent, such as methylene or ethylidene.

The term “alkoxy” may be linear, branched, or cyclic. The number of carbon atoms of the alkoxy is not particularly limited, but is preferably 1 to 20. Specific examples of the alkoxy include, but are not limited to, methoxy, ethoxy, n-propyloxy, isopropoxy, i-propyloxy, n-butoxy, isobutyloxy, tert-butoxy, sec-butoxy, n-pentoxy, neopentoxy, isopentoxy, n-hexoxy, 3,3-dimethylbutoxy, 2-ethylbutoxy, n-octoxy, n-nonyloxy, n-decyloxy, etc.

The term “phosphine oxide group” refers to a structure of —P(=O)($R_m$)($R_n$), wherein $R_m$ and $R_n$ are the same or different from each other and are independently hydrogen, deuterium, substituted or unsubstituted alkyl, substituted or unsubstituted aryl, or substituted or unsubstituted heteroaryl. Specific examples of the phosphine oxide group include an alkyl phosphine oxide group, an aryl phosphine oxide group, etc., and more specifically, include but are not limited to a diphenylphosphine oxide group, a diphenylphosphine oxide group, etc.

The term “alkylene” or “alkylene chain” refers to a completely saturated linear or branched divalent hydrocarbon chain group with one to twelve carbon atoms, generally expressed as C1-C12 alkylene. The alkylene is preferably C1-C6 alkylene, and more preferably C1-C4 alkylene. Non-limiting examples of C1-C12 alkylene include methylene, ethylidene, propylidene, n-butylidene, vinylidene, propenylene, n-butenylidene, propynylidene, n-butynelene, etc. The alkylene chain is connected to a remaining part of a molecule through a single bond and to the group through a single bond. Points at which the alkylene chain is connected to the remaining part of the molecule and to the group may pass through one carbon or any two carbons within the chain. Unless otherwise specified in this specification, the alkylene chain may be optionally substituted.

In the present disclosure, examples of halogen groups may include fluorine, chlorine, bromine, or iodine.

In the present disclosure, the term “cycloalkyl” refers to a monocyclic saturated hydrocarbon system without heteroatoms and double bonds. For example, examples of the term “$C_{3-9}$ cycloalkyl” include, but are not limited to, cyclopropyl, cyclobutyl, cyclopentyl, cyclohexyl, cycloheptyl, cyclooctyl, and cyclononyl.

In the present disclosure, the term “aryl” refers to an aromatic ring group having an all-carbon single ring or fused multi-ring of a conjugated a electron system, obtained by removing a hydrogen atom from a single carbon atom in a parent aromatic ring system. The aromatic ring group includes bicyclic groups containing aromatic rings fused with saturated or partially unsaturated rings or aromatic carbon rings. Specific examples of the aryl include phenyl or naphthyl, but are not limited thereto.

In the present disclosure, the term “heterocycloalkyl” refers to a 5- to 12-membered saturated non-aromatic system having cyclic carbon atoms and 1 to 2 cyclic heteroatoms. Specific examples of the heterocycloalkyl include piperidyl or tetrahydropyrrolyl, but are not limited thereto.

In the present disclosure, the term “heteroaryl” refers to a monovalent aryl containing at least one heteroatom independently selected from nitrogen, oxygen, or sulfur. The heteroaryl may be a single ring or a multi-ring system, such as a bicyclic system, wherein two or more rings exist in a form of parallel rings, bridge rings, or helical rings, wherein at least one ring contains one or more heteroatoms. Specific examples of the heteroaryl include pyridyl, thienyl, imidazolyl, pyrimidyl, pyridyl, furyl, pyrazinyl, thiazolyl, quinolyl, isoquinolyl, indolyl, benzimidazolyl, imidazopyridyl, benzofuryl, pyridazinyl, and isoindolyl, but are not limited thereto.

In the present disclosure, when the heteroaryl is substituted, the substituent may include

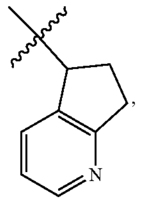 [SMILES: *C1CCc2ncccc21]

but is not limited thereto.

The term "heterocyclic" refers to a 5- to 12-membered saturated non-aromatic system having cyclic carbon atoms and 1 to 2 cyclic heteroatoms, wherein the heteroatoms are independently selected from nitrogen, sulfur, or oxygen atoms. In a heterocyclic group containing one or more nitrogen atoms, connection points may be carbon or nitrogen atoms, as long as the atomic valence allows. The heterocyclic may be a single-ring or multi-ring system, such as a bicyclic system, wherein two or more rings exist in a form of parallel rings, bridge rings, or helical rings, wherein at least one ring contains one or more heteroatoms.

As used herein, the term "partially unsaturated" refers to a cyclic portion that includes at least one double or triple bond. The term "partially unsaturated" is intended to encompass rings with a plurality of unsaturated sites, but is not intended to include aryl or heteroaryl portions as defined herein.

Drug or Pharmaceutical Composition

The term "pharmaceutically acceptable" refers to compounds, materials, compositions, and/or formulations that are suitable for use in contact with human and animal tissues within reasonable medical determination ranges, without excessive toxicity, irritation, anaphylaxis, or other problems or complications that are commensurate with reasonable benefit/risk ratios.

The term "pharmaceutically acceptable salt" refers to a salt that retains the biological efficacy of free acids and bases of a specific compound without any biological adverse effects, such as acid (including organic and inorganic acids) addition salts or base addition salts (including organic and inorganic bases).

The pharmaceutically acceptable salt of the present disclosure may be synthesized by a conventional chemical method from a parent compound containing acid or base groups. Generally, a preparation method for such salts includes reaction of these compounds in a form of free acids or bases with stoichiometric appropriate bases or acids in water, organic solvents, or a mixture of both.

The drug or pharmaceutical composition of the present disclosure may be applied orally, locally, parenterally or mucosally (for example, orally, by inhalation, or rectally) in dosage units containing conventional non-toxic pharmaceutically acceptable carriers.

For oral administration in a tablet or capsule form, active drug ingredients may be combined with non-toxic, pharmaceutically acceptable excipients such as binders (such as pre-gelatinized corn starch, polyvinyl pyrrolidone, or hydroxypropyl methylcellulose); fillers (such as lactose, sucrose, glucose, mannitol, sorbitol and other reducing and non-reducing saccharides, microcrystalline cellulose, calcium sulfate or calcium hydrogen phosphate); lubricants (such as magnesium stearate, talc powder or silica, stearic acid, sodium stearate fumarate, glyceryl dodecanoate, and calcium stearate); disintegrants (such as potato starch or sodium hydroxyacetate starch); or humectants (such as sodium lauryl sulfate), coloring and seasoning agents, gelatin, sweeteners, natural and synthetic gums (such as arabic gum, tragacanth gum or alginate), buffer salts, carboxymethyl cellulose, polyethylene glycol, wax, etc. For oral administration in a liquid form, the drug ingredients may be combined with non-toxic, pharmaceutically acceptable inert carriers (such as ethanol, glycerol, or water), anti-settling agents (such as sorbitol syrup, cellulose derivatives, or hydrogenated edible fats), emulsifiers (such as lecithin or arabic gum), non-aqueous carriers (such as almond oil, oil esters, ethanol, or fractionated vegetable oils), preservatives (such as methyl p-hydroxybenzoate or propyl p-hydroxybenzoate or sorbic acid), etc. Stabilizers such as antioxidants (BHA, BHT, propyl citrate, sodium ascorbate, and citric acid) may also be added to stabilize the dosage form.

Tablets containing active compounds may be coated by well-known methods in the art. The composition of the present disclosure, which includes the compound of formula I as an active compound, may also introduce small beads, microspheres, or microcapsules, such as those constructed from polyglycolic acid/lactic acid (PGLA). Formulations of liquids used for oral administration may be in a form of, for example, solutions, syrups, lotion or suspensions, or they may appear as dry products reconstituted with water or other suitable excipients before use.

Formulations used for oral administration may be appropriately prepared to achieve controlled or delayed release of active compounds.

The drug or pharmaceutical composition of the present disclosure may be delivered parenterally, namely, through intravenous (i.v.), intraventricular (i.c.v.), subcutaneous (s.c.), intraperitoneal (i.p.), intramuscular (i.m.), subcutaneous (s.d.), or intradermal (i.d.) administration, by direct injection, such as rapid concentrated injection or continuous infusion. A formulations used for injection may be presented in a unit dosage form, such as in an ampoule or multi-dose container with added preservative. The composition may be in a shape of an excipient, in a form of suspension, solution, or lotion in oil or aqueous carrier, and may include preparation reagents such as anti-settling agent, stabilizer, and/or dispersant. Alternatively, the active ingredient may be reconstituted in a powder form with a suitable carrier (such as sterile pyrogen-free water) before use.

The drug or pharmaceutical composition of the present disclosure may further be formulated for rectal administration, such as suppositories or retention enemas (for example, containing conventional suppository matrices such as cocoa butter or other glycerides).

The term "treating" includes inhibiting, alleviating, preventing, or eliminating one or more symptoms or side effects related to the treated disease, condition, or disorder.

The use of the term "reduce". "inhibit", "alleviate", or "decrease" is relative to controls. Those skilled in the art will easily determine appropriate controls for each experiment. For example, a reduction reaction in subjects or cells treated with a compound is compared with a reaction in subjects or cells not treated with the compound.

As used herein, the term "effective dose" or "therapeutic effective dose" refers to a dose that is sufficient to treat, inhibit, or alleviate one or more symptoms of the treated disease or provide desired pharmacological and/or physiological effects in other ways. A precise dose varies based on many factors, such as subject dependent variables (such as age and immune system health), disease or condition, and administered treatment. Effects of effective doses may be compared with those of controls. These controls are known in the art and discussed herein, and may be used for comparing combination effects with effects of only one drug in conditions of subjects before a drug or pharmaceutical composition is administrated or when the drug or pharmaceutical composition is not administrated or in a case of a pharmaceutical composition.

The term "excipient" used herein includes any other compound that may be included in or on microparticles and is not a therapeutic or bioactive compound. Therefore, the excipient should be pharmaceutically or biologically acceptable or relevant, for example, the excipient is usually non-toxic to subjects. The "excipient" includes a single compound and is also intended to include many compounds.

The term "pharmaceutical composition" refers to a composition including the compound or pharmaceutically acceptable salt thereof as disclosed in the present disclosure, as well as at least one of the following pharmaceutically acceptable ingredient selected based on properties of an application method and a dosage form, including but not limited to: carriers, diluents, adjuvants, excipients, preservatives, fillers, disintegrants, wetting agents, emulsifiers, suspensions, sweeteners, correctives, fragrances, antibacterial agents, anti-fungal agents, lubricants, dispersants, temperature-sensitive materials, temperature regulators, adhesives, stabilizers, suspension aids, and the like.

Use and Therapeutic Method

The terms "patient", "subject", "individual", etc. may be used interchangeably herein and refer to any animal that comply with the methods described herein or its cells, whether in vitro or in situ. In some non-restrictive implementations, patients, subjects, or individuals are persons.

The method, compound, or composition of the present disclosure may be used for effectively treating NRLP3 related diseases or alleviating their severity in any amount and through any administration route.

The present disclosure relates to a method for inhibiting NRLP3 in a biological sample, including a step of contact between the biological sample and the compound or the composition including the compound of the present disclosure.

The term "biological sample" includes (but is not limited to) cell cultures or extracts thereof; biopsy materials obtained from mammals or extracts thereof; blood, saliva, urine, feces, semen, tears, or other body fluids, or extracts thereof. The activation of enzymes in biological samples may be used for various purposes known to those skilled in the art. Examples of such purposes include (but are not limited to) biological analysis, gene expression research, and biological target identification.

The method for inhibiting NRLP3 in a patient in the present disclosure includes a step of administering, to the patient, the compound or the composition including the compound of the present disclosure.

The provided compound is an NRLP3 inhibitor and can therefore be used for treating one or more diseases related to NRLP3 activity. Therefore, in some embodiments, the present disclosure provides a method for treating an NRLP3 mediated disease, including a step of administering, to a patient in need, the compound of the present disclosure or a pharmaceutically acceptable composition thereof.

As used herein, the symptoms, diseases, and/or conditions "mediated by the term NRLP3" refer to any disease or other harmful condition known to be affected by NRLP3 or mutants thereof. Therefore, another embodiment of the present disclosure relates to treatment of one or more diseases known to be affected by NRLP3 or mutants thereof, or alleviation of their severity.

Combined Therapeutic Method

The present disclosure provides a combined therapeutic method using the compound of the present disclosure and other therapeutic drugs. The term "combined therapeutic method" used in the present disclosure includes administering these drugs in a sequential manner, wherein each therapeutic agent is administered at different time, and these therapeutic agents or at least two drugs are administered almost simultaneously. The order of each reagent or almost simultaneous administration may be affected by any appropriate pathway, including but not limited to oral, intravenous, intramuscular, and subcutaneous pathways, and direct absorption through mucosal tissues. Drugs may be applied by the same or different pathways. For example, a first drug may be administered orally, and a second dug may be administered intravenously. In addition, selected drugs of a composition may be administered intravenously, while other drugs of the composition may be administered orally. Alternatively, for example, two or more drugs may be administered intravenously or subcutaneously.

II. Examples

The present disclosure will be further explained below with reference to examples. Descriptions of specific exemplary embodiments of the present disclosure are for the purpose of explanation and illustration. These descriptions are not intended to limit the present disclosure to the precise form disclosed, and it is evident that many changes and variations may be made according to the teachings of the specification of the present disclosure. The purpose of selecting and describing the exemplary embodiments is to explain the specific principle of the present disclosure and its practical application, so that a person skilled in the art can implement and use various exemplary embodiments of the present disclosure and various different choices and changes.

Experimental methods used in the following examples are all conventional methods, unless otherwise specified.

Materials, reagents, etc. used in the following examples may be all obtained from commercial sources, unless otherwise specified.

Example 1: Synthesis of (R)-2-(4-((1-methylpiperidin-3-yl)amine)phthalazin-1-yl)-5-(trifluoromethyl)phenol

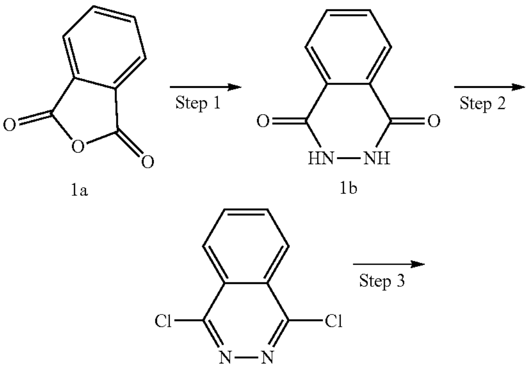

1a 1b 1c

-continued

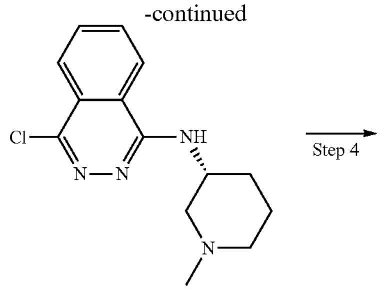

1d

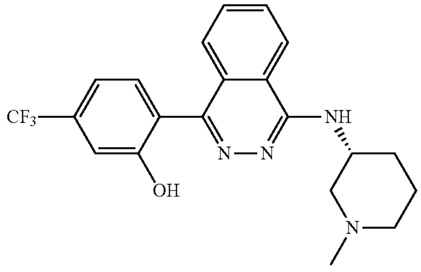 [SMILES: CN1CCC[C@@H](Nc2nnc(-c3ccc(C(F)(F)F)cc3O)c3ccccc23)C1]

1

Step 1: A compound phthalic anhydride (1a) (1.0 g, 6.75 mmol) and $N_2H_4 \cdot H_2O$ (1.01 g, 20.25 mmol) were dissolved in acetic acid (20 mL), followed by heating to 120 °C for overnight reflux. Complete reaction was determined by TLC, the reaction solution was directly concentrated, then water (20 ml) was added to disperse the solid, filtration was performed, and filter cakes were drained and dried in vacuum overnight to obtain a target compound 1b (2,3-dihydrophthalazine-1,4-dione) (0.75 g, yield: 68.51%, LCMS m/z=163.2 $[M+1]^+$).

Step 2: The compound (1b) (0.20 g, 1.23 mmol) was dissolved in $POCl_3$ (2 mL), followed by heating to 100 °C for overnight reaction. Complete reaction was determined by TLC, the reaction solution was directly concentrated to remove the $POCl_3$, then the oily crude product was slowly added dropwise to ice water (20 ml), the solution was stirred thoroughly, the pH value was adjusted to 8 with 2N sodium hydroxide aqueous solution, extraction was performed with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (PE: EA=20:1) to obtain a target compound 1c (1,4-dichlorophthalazine) (0.21 g, yield: 85.54%, LCMS m/z=199.2 $[M+1]^+$).

Step 3: The compound (1c) (0.20 g, 1.00 mmol), (R)-1-methylpiperidine-3-amine (0.126 g, 1.11 mmol), and $Na_2CO_3$ (0.21 g, 2.01 mmol) were dissolved in dry DMF (2 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10:1) to obtain a target compound (1d) ((R)-4-chloro-N-(1-methylpiperidin-3-yl)phthalazine-1-amine) (0.06 g, yield: 21.57%, LCMS m/z=277.2 $[M+1]^+$).

Step 4: The compound (1d) (0.05 g, 0.18 mmol), (2-hydroxy-4-(trifluoromethyl)phenyl)boronic acid (0.045 g, 0.217 mmol), sodium carbonate (0.04 g, 0.36 mmol), and $Pd(dppf)Cl_2$ (15.00 mg, 0.02 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a compound 1 ((R)-2-(4-((1-methylpiperidin-3-yl)amine)phthalazin-1-yl)-5-(trifluoromethyl)phenol) (0.01 g, yield: 13.76%, LCMS m/z=403.2 $[M+1]^+$).

Example 2: Synthesis of (R)-2-(4-((1-methylpiperidin-3-yl)amino)-5,6,7,8-tetrahydrophthalazin-1-yl)-5-(trifluoromethyl)phenol

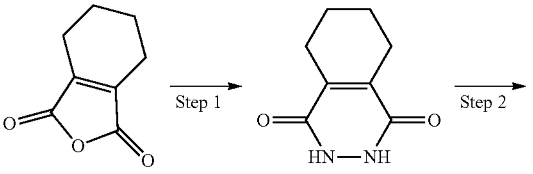

2a 2b

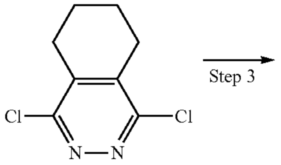

2c

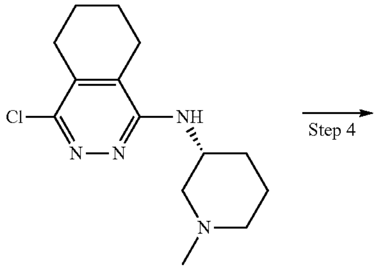

2d

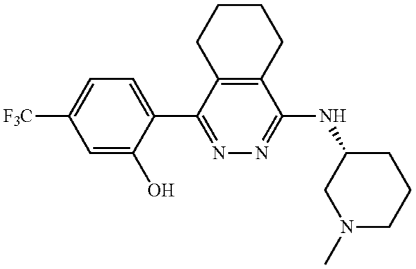

2

Step 1: A compound 4,5,6,7-tetrahydroisobenzofuran-1,3-dione (2a) (1.0 g, 6.57 mmol) and $N_2H_4 \cdot H_2O$ (0.98 g, 19.72 mmol) were dissolved in acetic acid (20 mL), followed by heating to 120 °C for overnight reflux. Complete reaction was determined by TLC, the reaction solution was directly concentrated, then water (20 ml) was added to disperse the solid, filtration was performed, and filter cakes were drained and dried in vacuum overnight to obtain a target compound 2b (2,3,5,6,7,8-hexahydrophthalazine-1,4-dione) (0.60 g, yield: 54.93%, LCMS m/z=167.2 [M+]$^+$).

Step 2: The compound (2b) (0.20 g, 1.20 mmol) was dissolved in $POCl_3$ (2 mL), followed by heating to 100 °C for overnight reaction. Complete reaction was determined by TLC, the reaction solution was directly concentrated to remove the $POCl_3$, then the oily crude product was slowly added dropwise to ice water (20 ml), the solution was stirred thoroughly, the pH value was adjusted to 8 with 2N sodium hydroxide aqueous solution, extraction was performed with ethyl acetate (10 mL×3), organic phases were combined, washed with saturated salt water (10 mL/3), dried with anhydrous sodium sulfate, and filtered, the solvent was removed from the filtrate under reduced pressure, and the residue was separated by column chromatography (PE: EA=20:1) to obtain a target compound (2c) (1,4-dichloro-5,6,7,8-tetrahydrophthalazine) (0.15 g, yield: 61.38%, LCMS m/z=204.2 [M+1]$^+$).

Step 3: The compound (2c) (0.15 g, 0.738 mmol), (R)-1-methylpiperidine-3-amine (0.093 g, 0.81 mmol), and $Na_2CO_3$ (0.16 g, 1.48 mmol) were dissolved in dry DMF (2 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10:1) to obtain a target compound (2d) ((R)-4-chloro-N-(1-methylpiperidin-3-yl)-5,6,7,8-tetrahydrophenylene-1-amine) (0.05 g, yield: 24.11%, LCMS m/z=281.2 [M+1]$^+$).

Step 4: The compound (2d) (0.05 g, 0.18 mmol), (2-hydroxy-4-(trifluoromethyl)phenyl)boronic acid (0.044 g, 0.214 mmol), sodium carbonate (0.037 g, 0.36 mmol), and Pd(dppf)$Cl_2$ (15.00 mg, 0.02 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound 2 ((R)-2-(4-((1-methylpiperidin-3-yl)amino)-5,6,7,8-tetrahydrophthalazin-1-yl)-5-(trifluoromethyl)phenol) (0.011 g, yield: 15.20%, LCMS m/z=407.2 [M+1]$^+$).

Example 3: Synthesis of (R)-2-(7-methyl-4-((1-methylpiperidin-3-yl)amino)phthalazin-1-yl)-5-(trifluoromethyl)phenol

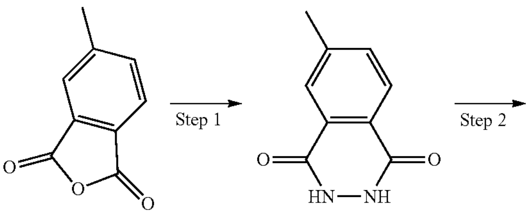

3a 3b

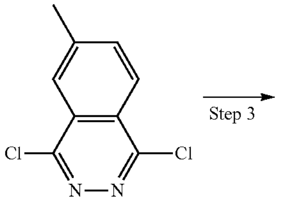

3c

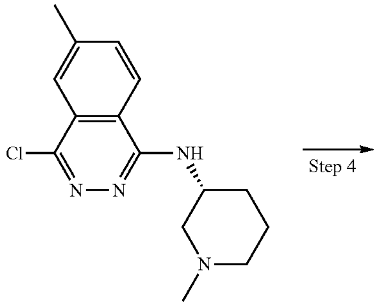

3d

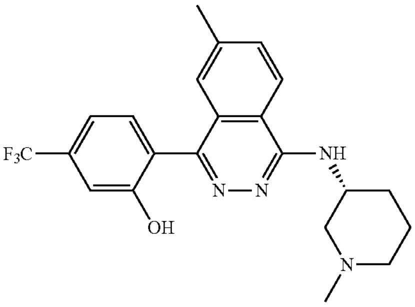

3

Step 1: A compound 4-methylphthalic anhydride (3a) (2.0 g, 12.33 mmol) and $N_2H_4 \cdot H_2O$ (1.85 g, 37.00 mmol) were dissolved in acetic acid (30 mL), followed by heating to 120 °C for overnight reflux. Complete reaction was determined by TLC, the reaction solution was directly concentrated, then water (20 ml) was added to disperse the solid, filtration was performed, and filter cakes were drained and dried in vacuum overnight to obtain a target compound 3b (6-methyl-2,3-dihydrophthalazine-1,4-dione) (1.51 g, yield: 69.03%, LCMS m/z=177.2 [M+1]$^+$).

Step 2: The compound (3b) (1.51 g, 8.57 mmol) was dissolved in $POCl_3$ (10 mL), followed by heating to 100 °C for overnight reaction. Complete reaction was determined by TLC, the reaction solution was directly concentrated to remove the $POCl_3$, then the oily crude product was slowly added dropwise to ice water (50 ml), the solution was stirred thoroughly, the pH value was adjusted to 8 with 2N sodium hydroxide aqueous solution, extraction was performed with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (PE: EA=10:1) to obtain a target compound (3c) (1,4-dichloro-6-methylphthalazine) (1.45 g, yield: 79.40%, LCMS m/z=213.2 $[M+1]^+$).

Step 3: The compound (3c) (0.20 g, 0.94 mmol), (R)-1-methylpiperidine-3-amine (0.12 g, 1.04 mmol), and $Na_2CO_3$ (0.20 g, 1.89 mmol) were dissolved in dry DMF (2 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10:1) to obtain a mixture of target compounds (3d) and (4d) (0.08 g, yield: 29.31%, LCMS m/z=291.2 $[M+1]^+$).

Step 4: The mixture of compounds (3d) and (4d) (0.08 g, 0.27 mmol), (2-hydroxy-4-(trifluoromethyl)phenyl)boronic acid (0.074 g, 0.357 mmol), sodium carbonate (0.058 g, 0.55 mmol), and Pd(dppf)$Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by PTLC (DCM:$CH_3OH$=10:1) to obtain a target compound 3 ((R)-2-(7-methyl-4-((1-methylpiperidin-3-yl)amino)phthalazin-1-yl)-5-(trifluoromethyl)phenol) (0.011 g, yield: 8.73%, LCMS m/z=417.2 $[M+1]^+$).

Example 4: Synthesis of (R)-2-(6-methyl-4-((1-methylpiperidin-3-yl)amino)phthalazin-1-yl)-5-(trifluoromethyl)phenol

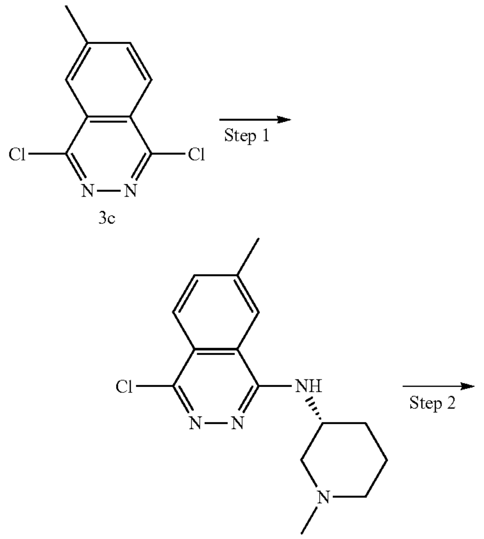

3c

4d

-continued

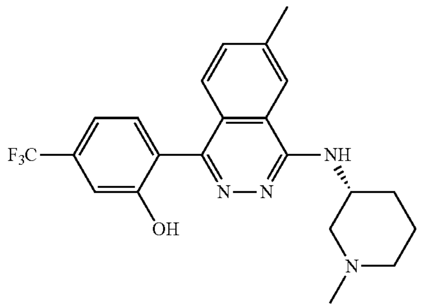

4

Step 1: The compound (3c) (0.20 g, 0.94 mmol), (R)-1-methylpiperidine-3-amine (0.12 g, 1.04 mmol), and $Na_2CO_3$ (0.20 g, 1.89 mmol) were dissolved in dry DMF (2 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10:1) to obtain a mixture of target compounds (4d) and (3d) (0.08 g, yield: 29.31%, LCMS m/z=291.2 $[M+1]^+$).

Step 2: The mixture of compounds (3d) and (4d) (0.08 g, 0.27 mmol), (2-hydroxy-4-(trifluoromethyl)phenyl)boronic acid (0.074 g, 0.357 mmol), sodium carbonate (0.058 g, 0.55 mmol), and Pd(dppf)$Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by PTLC (DCM:$CH_3OH$=10:1) to obtain a target compound 4 ((R)-2-(6-methyl-4-((1-methylpiperidin-3-yl)amino)phthalazin-1-yl)-5-(trifluoromethyl)phenol) (0.008 g, yield: 6.98%, LCMS m/z=417.2 $[M+1]^+$).

Example 5: Synthesis of (R)-2-(7-methoxy-4-((1-methylpiperidin-3-yl)amino)phthalazin-1-yl)-5-(trifluoromethyl)phenol

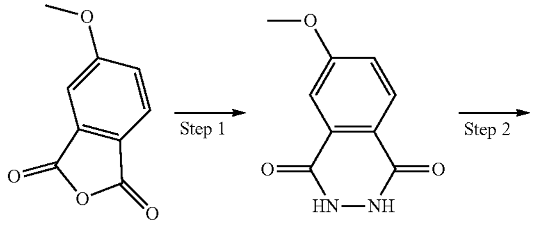

5a

5b

-continued

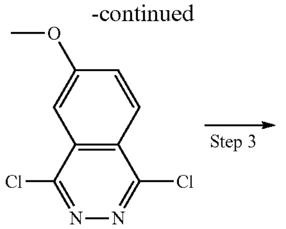

5c

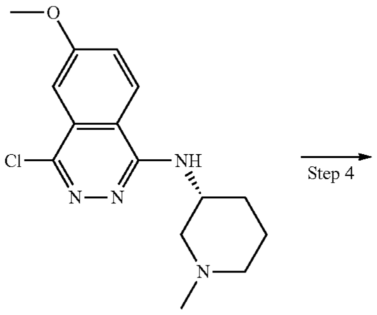

5d

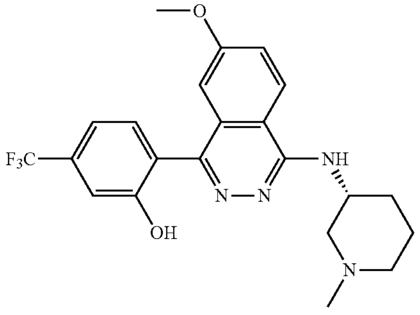

5

Step 1: A compound 4-methoxyphthalic anhydride (5a) (2.0 g, 11.23 mmol) and $N_2H_4 \cdot H_2O$ (1.69 g, 33.68 mmol) were dissolved in acetic acid (30 mL), followed by heating to 120 °C for overnight reflux. Complete reaction was determined by TLC, the reaction solution was directly concentrated, then water (20 ml) was added to disperse the solid, filtration was performed, and filter cakes were drained and dried in vacuum overnight to obtain a target compound 5b (6-methoxy-2,3-dihydrophthalazine-1,4-dione) (1.42 g, yield: 65.82%, LCMS m/z=193.2 [M+1]1.

Step 2: The compound (5b) (1.42 g, 7.39 mmol) was dissolved in $POCl_3$ (10 mL), followed by heating to 100 °C for overnight reaction. Complete reaction was determined by TLC, the reaction solution was directly concentrated to remove the $POCl_3$, then the oily crude product was slowly added dropwise to ice water (50 ml), the solution was stirred thoroughly, the pH value was adjusted to 8 with 2N sodium hydroxide aqueous solution, extraction was performed with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (PE: EA=10:1) to obtain a target compound (5c) (1,4-dichloro-6-methoxyphthalazine) (1.20 g, yield: 70.90%, LCMS m/z=229.2 $[M+1]^+$).

Step 3: The compound (5c) (0.20 g, 0.87 mmol), (R)-1-methylpiperidine-3-amine (0.11 g, 0.96 mmol), and $Na_2CO_3$ (0.20 g, 1.89 mmol) were dissolved in dry DMF (2 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10: 1) to obtain a mixture of target compounds (5d) and (6d) (0.09 g, yield: 33.60%, LCMS m/z=307.2 $[M+1]^+$).

Step 4: The mixture of compounds (5d) and (6d) (0.09 g, 0.29 mmol), (2-hydroxy-4-(trifluoromethyl)phenyl)boronic acid (78.53 mg, 0.38 mmol), sodium carbonate (62.18 mg, 0.58 mmol), and Pd(dppf)$Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by PTLC (DCM:$CH_3OH$=10:1) to obtain a target compound 5 ((R)-2-(7-methoxy-4-((1-methylpiperidin-3-yl)amino)phthalazin-1-yl)-5-(trifluoromethyl) phenol) (0.01 g, yield: 7.88%, LCMS m/z=433.2 $[M+1]^+$).

Example 6: Synthesis of (R)-2-(6-methoxy-4-((1-methylpiperidin-3-yl)amino)phthalazin-1-yl)-5-(trifluoromethyl)phenol

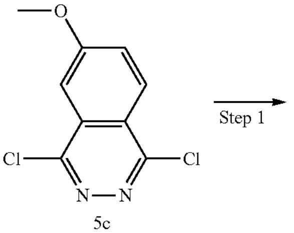

5c

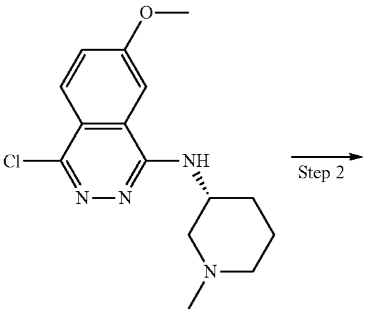

6d

-continued

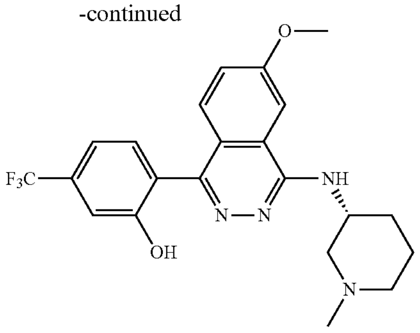

6

Step 1: The compound (5c) (0.20 g, 0.87 mmol), (R)-1-methylpiperidine-3-amine (0.11 g, 0.96 mmol), and $Na_2CO_3$ (0.20 g, 1.89 mmol) were dissolved in dry DMF (2 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10: 1) to obtain a mixture of target compounds (6d) and (5d) (0.09 g, yield: 33.60%, LCMS m/z=307.2 $[M+1]^+$).

Step 2: The mixture of compounds (5d) and (6d) (0.09 g, 0.29 mmol), (2-hydroxy-4-(trifluoromethyl)phenyl)boronic acid (78.53 mg, 0.38 mmol), sodium carbonate (62.18 mg, 0.58 mmol), and $Pd(dppf)Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by PTLC (DCM:$CH_3OH$=10:1) to obtain a target compound 6 ((R)-2-(6-methoxy-4-((1-methylpiperidin-3-yl)amino)phthalazin-1-yl)-5-(trifluoromethyl)phenol) (0.008 g, yield: 6.31%, LCMS m/z=433.2 $[M+1]^+$).

Example 7: Synthesis of (R)-2-(4-((1-phenylethyl)amino)phthalazin-1-yl)-5-(trifluoromethyl)phenol

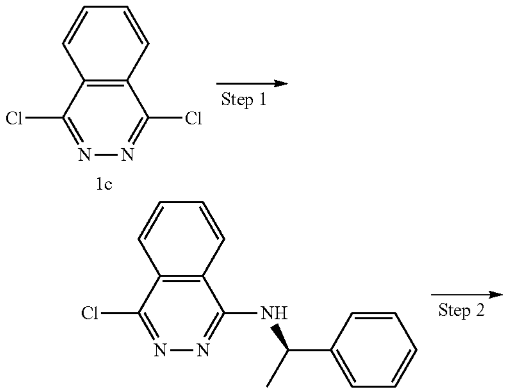

1c

7a

-continued

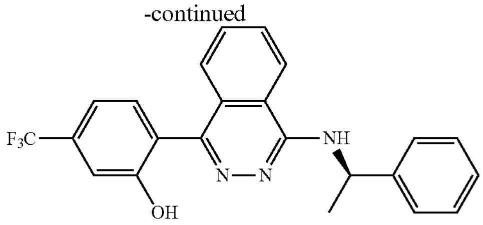

7

Step 1: The compound (1c) (0.20 g, 1.00 mmol), (R)-1-methylbenzylamine (0.15 g, 1.21 mmol), and $Na_2CO_3$ (0.21 g, 2.01 mmol) were dissolved in dry DMF (2 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (PE:EA=3:1) to obtain a target compound (7a) ((R)-4-chloro-N-(1-phenylethyl)phthalazin-1-amine) (0.14 g, yield: 49.10%, LCMS m/z=284.2 $[M+1]^+$).

Step 2: The compound (7a) (0.05 g, 0.17 mmol), (2-hydroxy-4-(trifluoromethyl)phenyl)boronic acid (39.91 mg, 0.19 mmol), sodium carbonate (37.35 mg, 0.35 mmol), and $Pd(dppf)Cl_2$ (10.24 mg, 0.014 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (PE:EA=3:1) to obtain a target compound 7 ((R)-2-(4-((1-phenylethyl)amino)phthalazin-1-yl)-5-(trifluoromethyl)phenol) (0.02 g, yield: 27.72%. LCMS m/z=410.2 $[M+1]^+$).

Example 8: Synthesis of (S)-2-(4-((1-phenylethyl)amino)phthalazin-1-yl)-5-(trifluoromethyl)phenol

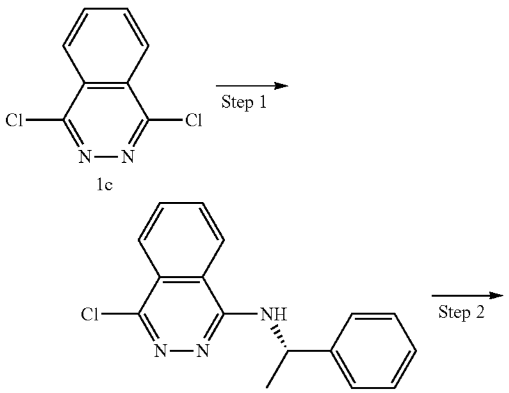

1c

8a

-continued

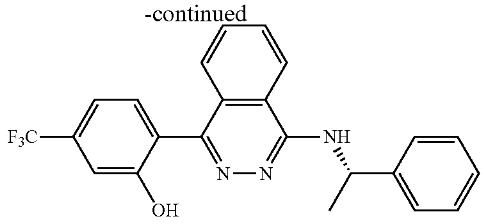

8

Step 1: The compound (1c) (0.20 g, 1.0) mmol), (S)-1-methylbenzylamine (0.15 g, 1.21 mmol), and $Na_2CO_3$ (0.21 g, 2.01 mmol) were dissolved in dry DMF (2 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (PE:EA=3:1) to obtain a target compound (8a) ((S)-4-chloro-N-(1-phenylethyl)phthalazin-1-anine) (0.14 g, yield: 49.10%, LCMS m/z=284.2 $[M+1]^+$).

Step 2: The compound (8a) (0.05 g, 0.17 mmol). (2-hydroxy-4-(trifluoromethyl)phenyl)boronic acid (39.91 mg, 0.19 mmol), sodium carbonate (37.35 mg, 0.35 mmol), and $Pd(dppf)Cl_2$ (10.24 mg, 0.014 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (PE:EA=3:1) to obtain a target compound 8 ((S)-2-(4-((1-phenylethyl)amino)phthalazin-1-yl)-5-(trifluoromethyl)phenol) (0.02 g, yield: 27.72%. LCMS m/z=410.2 $[M+1]^+$).

Example 9: Synthesis of (R)-2-(4-((1-(4-fluorophenyl)ethyl)amino)phthalazin-1-yl)-5-(trifluoromethyl) phenol

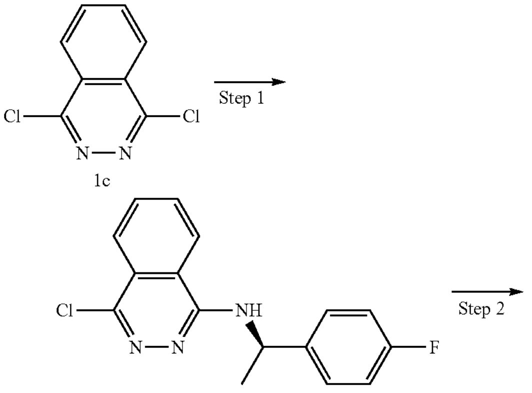

1c

9a

-continued

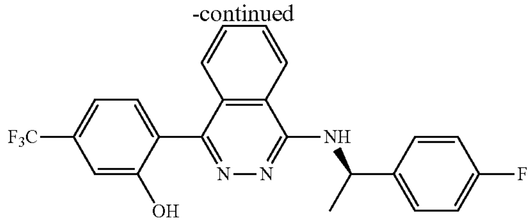

9

Step 1: The compound (1c) (0.20 g, 1.00 mmol), (R)-1-(4-fluorophenyl)ethane-1-amine (0.16 g, 1.20 mmol), and $Na_2CO_3$ (0.21 g, 2.01 mmol) were dissolved in dry DMF (2 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (PE: EA=3:1) to obtain a target compound (9a) (R)-4-chloro-N-(1-(4-fluorophenyl)ethyl)phthalazine-1-amine (0.12 g, yield: 39.58%, LCMS m/z=302.2 $[M+1]^+$).

Step 2: The compound (9a) (0.05 g, 0.16 mmol). (2-hydroxy-4-(trifluoromethyl)phenyl)boronic acid (37.53 mg, 0.18 mmol), sodium carbonate (35.12 mg, 0.33 mmol), and $Pd(dppf)Cl_2$ (10.24 mg, 0.014 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (PE:EA=3:1) to obtain a target compound 9 (((R)-2-(4-(1-(4-fluorophenyl)ethyl) amino)phthalazin-1-yl)-5-(trifluoromethyl)phenol) (0.02 g, yield: 28.24%, LCMS m/z=428.2 [M+1]f).

Example 10: Synthesis of (S)-2-(4-((1-(4-fluorophenyl)ethyl)amino)phthalazin-1-yl)-5-(trifluoromethyl) phenol

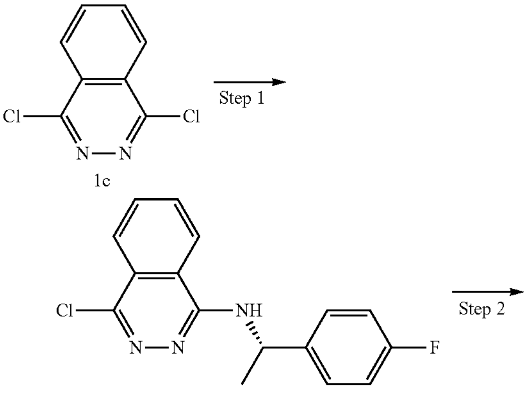

1c

10a

-continued

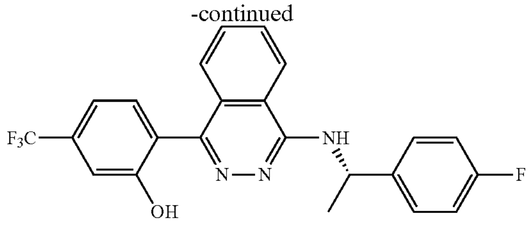

10

Step 1: The compound (1c) (0.20 g, 1.00 mmol), (S)-1-(4-fluorophenyl)ethane-1-amine (0.16 g, 1.20 mmol), and $Na_2CO_3$ (0.21 g, 2.01 mmol) were dissolved in dry DMF (2 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (PE: EA=3:1) to obtain a target compound (10a) ((S)-4-chloro-N-(1-(4-fluorophenyl)ethyl)phthalazine-1-amine) (0.12 g, yield: 39.58%, LCMS m/z=302.2 $[M+1]^+$).

Step 2: The compound (10a) (0.05 g, 0.16 mmol), (2-hydroxy-4-(trifluoromethyl)phenyl)boronic acid (37.53 mg, 0.18 mmol), sodium carbonate (35.12 mg, 0.33 mmol), and $Pd(dppf)Cl_2$ (10.24 mg, 0.014 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (PE:EA=3:1) to obtain a target compound 10 (((S)-2-(4-(1-(4-fluorophenyl)ethyl)amino)phthalazin-1-yl)-5-(trifluoromethyl)phenol) (0.015 g, yield: 21.18%, LCMS m/z=428.2 $[M+1]^+$).

Example 11: Synthesis of 2-(4-(butylamino)phthalazin-1-yl)-5-(trifluoromethyl)phenol

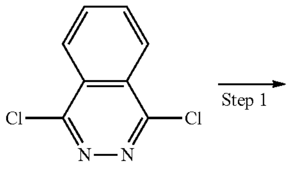

1c

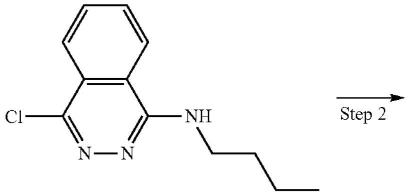

11a

-continued

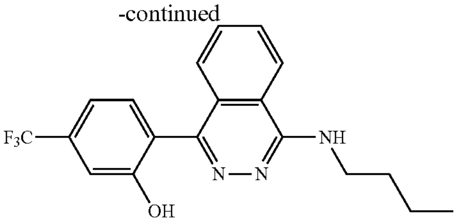

11

Step 1: The compound (1c) (0.10 g, 0.50 mmol), n-butylamine (0.036 g, 0.50 mmol), and $Na_2CO_3$ (0.11 g, 1.00 mmol) were dissolved in dry DMF (2 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL-3), dried with anhydrous sodium sulfate, and filtered, the solvent was removed from the filtrate under reduced pressure, and the residue was separated by column chromatography (PE:EA=3:1) to obtain a target compound (11a) (n-butyl-4-chlorophthalazine-1-amine) (0.05 g, yield: 42.22%, LCMS m/z=236.2 $[M+1]^+$).

Step 2: The compound (11a) (0.05 g, 0.21 mmol), (2-hydroxy-4-(trifluoromethyl)phenyl)boronic acid (52.42 mg, 0.25 mmol), sodium carbonate (44.96 mg, 0.42 mmol), and $Pd(dppf)Cl_2$ (10.24 mg, 0.014 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (PE:EA=3:1) to obtain a target compound 11 (2-(4-(butylamino)phthalazin-1-yl)-5-(trifluoromethyl)phenol (0.025 g, yield: 32.61%. LCMS m/z=362.2 $[M+1]^+$).

Example 12: (R)-2-(4-((1-(pyridin-2-yl)ethyl)amino)phthalazin-1-yl)-5-(trifluoromethyl)phenol

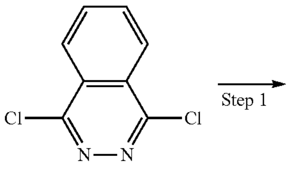

1c

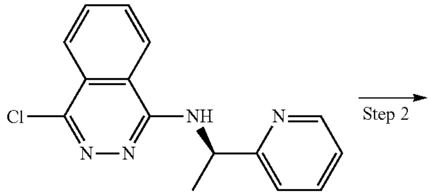

12a

-continued

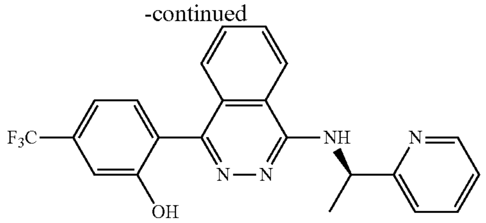

12

Step 1: The compound (1c) (0.10 g, 0.50 mmol), (R)-1-(pyrid-2-yl)ethane-1-amine (67.52 mg, 0.55 mmol), and $Na_2CO_3$ (0.11 g, 1.00 mmol) were dissolved in dry DMF (2 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (PE:EA=3:1) to obtain a target compound (12a) ((R)-4-chloro-N-(1-(pyridin-2-yl)ethyl)phthalazine-1-amine) (0.06 g, yield: 41.94%, LCMS m/z=285.2 $[M+1]^+$).

Step 2: The compound (12a) (0.06 g, 0.21 mmol), (2-hydroxy-4-(trifluoromethyl)phenyl)boronic acid (52.07 mg, 0.25 mmol), sodium carbonate (44.67 mg, 0.42 mmol), and $Pd(dppf)Cl_2$ (15.36 mg, 0.021 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (PE:EA=3:1) to obtain a target compound 12 ((R)-2-(4-((1-(pyridin-2-yl)ethyl)amino)phthalazin-1-yl)-5-(trifluoromethyl)phenol) (0.025 g, yield: 28.91%, LCMS m/z=411.2 $[M+1]^+$).

Example 13: Synthesis of (S)-2-(4-((1-(pyridin-2-yl)ethyl)amino)phthalazin-1-yl)-5-(trifluoromethyl)phenol

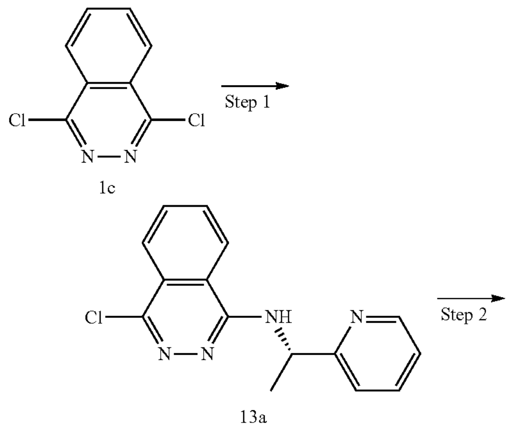

-continued

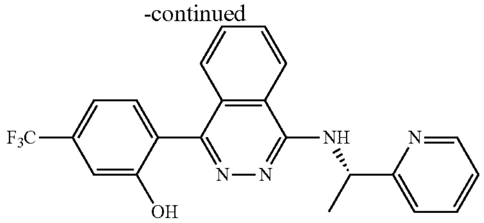

13

Step 1: The compound (1c) (0.10 g, 0.50 mmol), (S)-1-(pyrid-2-yl)ethane-1-amine (67.52 mg, 0.55 mmol), and $Na_2CO_3$ (0.11 g, 1.00 mmol) were dissolved in dry DMF (2 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (PE:EA=3:1) to obtain a target compound (13a) ((S)-4-chloro-N-(1-(pyridin-2-yl)ethyl)phthalazine-1-amine) (0.05 g. yield: 34.95%, LCMS m/z=285.2 $[M+1]^+$).

Step 2: The compound (13a) (0.05 g, 0.17 mmol), (2-hydroxy-4-(trifluoromethyl)phenyl)boronic acid (43.39 mg, 0.21 mmol), sodium carbonate (38.22 mg, 0.35 mmol), and $Pd(dppf)Cl_2$ (15.36 mg, 0.021 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (PE:EA=3:1) to obtain a target compound 13 ((S)-2-(4-((1-(pyridin-2-yl)ethyl)amino)phthalazin-1-yl)-5-(trifluoromethyl)phenol) (0.02 g, yield: 27.75%, LCMS m/z=411.2 $[M+1]^+$).

Example 14: Synthesis of 2-(5-{[(3R)-1-methylpiperidin-3-yl]amino}pyridino[2,3-d]pyridazin-8-yl)-5-(trifluoromethyl)phenol

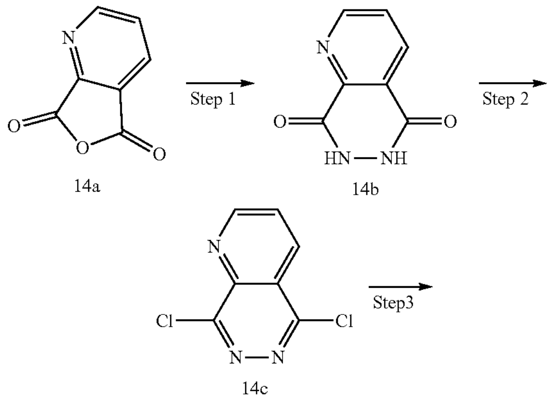

-continued

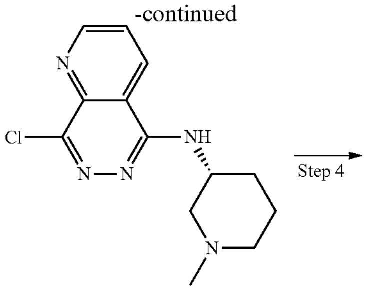

14d

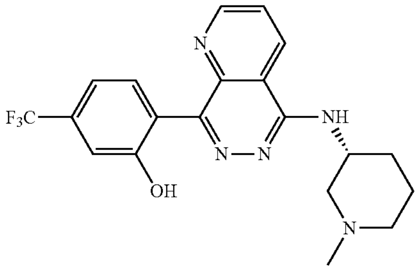

14

Step 1: A compound furano[3,4-b]pyridine-5,7-dione (14a) (3.0 g, 20.12 mmol) and $N_2H_4 \cdot H_2O$ (3.02 g, 60.36 mmol) were dissolved in acetic acid (50 mL), followed by heating to 120 °C for overnight reflux. Complete reaction was determined by TLC, the reaction solution was directly concentrated, then water (50 ml) was added to disperse the solid, filtration was performed, and filter cakes were drained and dried in vacuum overnight to obtain a target compound (14b) (6,7-dihydropyridino[2,3-d]pyridazine-5,8-dione) (2.30 g, yield: 70.07%, LCMS m/z=164.2 [M+1]J).

Step 2: The compound (14b) (2.30 g, 14.10 mmol) was dissolved in $POCl_3$ (20 mL), followed by heating to 100 °C for overnight reaction. Complete reaction was determined by TLC, the reaction solution was directly concentrated to remove the $POCl_3$, then the oily crude product was slowly added dropwise to ice water (50 ml), the solution was stirred thoroughly, the pH value was adjusted to 8 with 2N sodium hydroxide aqueous solution, extraction was performed with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (PE: EA=10:1) to obtain a target compound (14c) (5,8-dichloropyridino[2,3-d]pyridazine) (1.25 g, yield: 44.33%, LCMS m/z=200.2 $[M+1]^+$).

Step 3: The compound (14c) (0.20 g, 1.00 mmol), (R)-1-methylpiperidine-3-amine (0.14 g, 1.20 mmol), and $Na_2CO_3$ (0.21 g, 1.99 mmol) were dissolved in dry DMF (3 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10:1) to obtain a target compound (14d) ((3R)—N-(8-chloropyrido[2,3-d]pyridazin-5-yl)-1-methylpiperidine-3-anine) (0.13 g, yield: 46.80%, LCMS m/z=278.2 $[M+11]^+$).

Step 4: The compound (14d) (0.05 g, 0.18 mmol), (2-hydroxy-4-(trifluoromethyl)phenyl)boronic acid (44.00 mg, 0.22 mmol), sodium carbonate (29.15 mg, 0.27 mmol), and $Pd(dppf)Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound 14 (2-(5-{[(3R)-1-methylpiperidin-3-yl]amino}pyridino[2,3-d]pyridazin-8-yl)-5-(trifluoromethyl)phenol) (0.022 g, yield: 30.30%, LCMS m/z=404.4 $[M+1]^+$).

Example 15: Synthesis of 2-(8-{[(3R)-1-methylpiperidin-3-yl]amino}pyridino[2,3-d]pyridazin-5-yl)-5-(trifluoromethyl)phenol

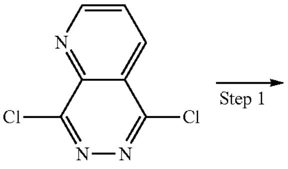

14c

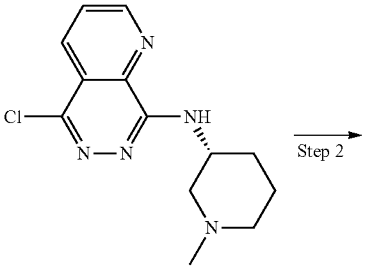

15d

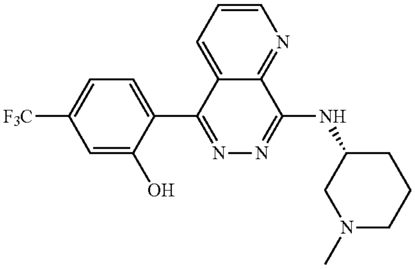

15

Step 1: The compound (14c) (0.20 g, 1.00 mmol), (R)-1-methylpiperidine-3-amine (0.14 g, 1.20 mmol), and $Na_2CO_3$ (0.21 g, 1.99 mmol) were dissolved in dry DMF (3 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10:1) to obtain a target compound (15d) ((3R)—N-(5-chloropyrido[2,3-d]pyridazin-8-yl)-1-methylpiperidine-3-amine) (0.04 g, yield: 14.40%, LCMS m/z=278.2 $[M+1]^+$).

Step 2: The compound (15d) (0.04 g, 0.14 mmol), (2-hydroxy-4-(trifluoromethyl)phenyl)boronic acid (35.00 mg, 0.17 mmol), sodium carbonate (22.10 mg, 0.21 mmol), and Pd(dppf)$Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound 15 (2-(8-{[(3R)-1-methylpiperidin-3-yl]amino}pyridino[2,3-d]pyridazin-5-yl)-5-(trifluoromethyl)phenol (0.015 g, yield: 26.56%, LCMS m/z=404.4 $[M+1]^+$).

Example 16: Synthesis of 2-(7-fluoro-4-{[(3R)-1-methylpiperidin-3-yl]amino}phthalazin-1-yl)-5-(trifluoromethyl)phenol

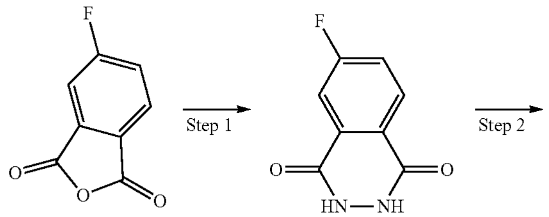

16a 16b

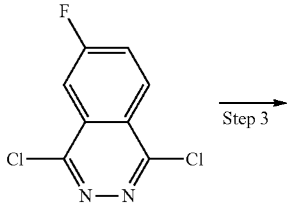

16c

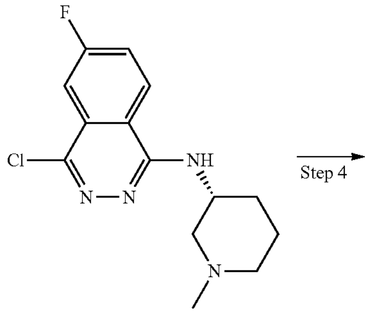

16d

-continued

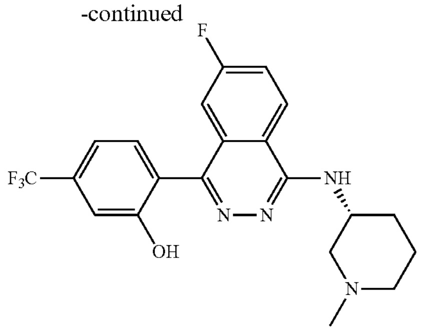

16

Step 1: A compound 5-fluoroisobenzofuran-1,3-dione (16a) (5.0 g, 30.10 mmol) and $N_2H_4{\cdot}H_2O$ (7.53 g, 150.50 mmol) were dissolved in acetic acid (50 mL), followed by heating to 120 °C for overnight reflux. Complete reaction was determined by TLC, the reaction solution was directly concentrated, then water (50 ml) was added to disperse the solid, filtration was performed, and filter cakes were drained and dried in vacuum overnight to obtain a target compound (16b) (6-fluoro-2,3-dihydrophthalazine-1,4-dione) (5.40 g, yield: 99.59%, LCMS m/z=181.1 $[M+1]^+$).

Step 2: The compound (16b) (5.40 g, 29.98 mmol) was dissolved in $POCl_3$ (30 mL), followed by heating to 100 °C for overnight reaction. Complete reaction was determined by TLC, the reaction solution was directly concentrated to remove the $POCl_3$, then the oily crude product was slowly added dropwise to ice water (50 ml), the solution was stirred thoroughly, the pH value was adjusted to 8 with 2N sodium hydroxide aqueous solution, extraction was performed with ethyl acetate (50 mL×3), organic phases were combined, washed with saturated salt water (50 mL×3), dried with anhydrous sodium sulfate, and filtered, the solvent was removed from the filtrate under reduced pressure, and the residue was separated by column chromatography (PE: EA=5:1) to obtain a target compound (16c) (1,4-dichloro-6-fluorophthalazine) (4.83 g, yield: 74.23%, LCMS m/z=217.0 $[M+1]^+$).

Step 3: The compound (16c) (0.20 g, 0.92 mmol), (R)-1-methylpiperidine-3-amine (0.14 g, 1.20 mmol), and $Na_2CO_3$ (0.21 g, 1.99 mmol) were dissolved in dry DMF (3 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10:1) to obtain a target compound (16d) ((R)-4-chloro-6-fluoro-N-(1-methylpiperidin-3-yl)phthalazine-1-amine) (0.05 g, yield: 18.41%, LCMS m/z=295.2 $[M+1]^+$)).

Step 4: The compound (16d) (0.05 g, 0.17 mmol), (2-hydroxy-4-(trifluoromethyl)phenyl)boronic acid (44.00 mg, 0.22 mmol), sodium carbonate (29.15 mg, 0.27 mmol), and Pd(dppf)$Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound 16 ((R)-2-(7-fluoro-4-((1-methylpiperidin-3-yl)amino)phthalazin-1-yl)-5-(trifluoromethyl)phenol) (0.01 g, yield: 14.02%, LCMS m/z=421.4 $[M+1]^+$).

Example 17: Synthesis of (R)-2-(1-((1-methylpiperidin-3-yl)amino)pyridino[3,4-d]pyridazin-4-yl))-5-(trifluoromethyl)phenol

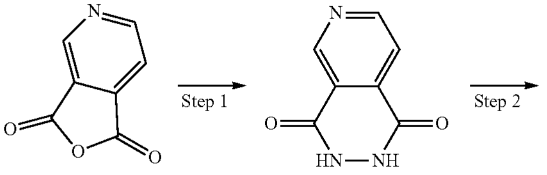

17a 17b

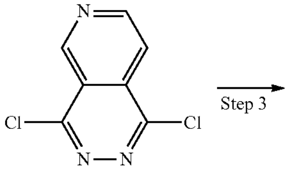

17c

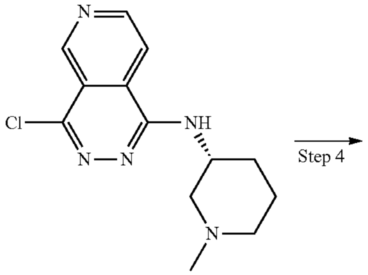

17d

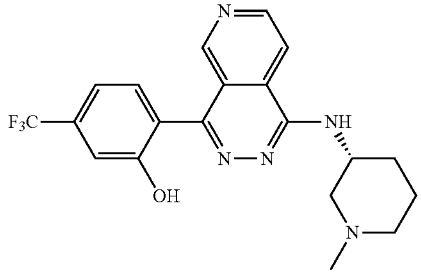

17

Step 1: A compound furano[3,4-c]pyridine-1,3-dione (17a) (3.0 g, 20.12 mmol) and $N_2H_4 \cdot H_2O$ (3.02 g, 60.36 mmol) were dissolved in acetic acid (50 mL), followed by heating to 120 °C for overnight reflux. Complete reaction was determined by TLC, the reaction solution was directly concentrated, then water (50 ml) was added to disperse the solid, filtration was performed, and filter cakes were drained and dried in vacuum overnight to obtain a target compound (17b) (2,3-dihydropyridino[3,4-d]pyridazine-1,4-dione) (2.10 g, yield: 63.97%, LCMS m/z=164.2 $[M+1]^+$).

Step 2: The compound (17b) (2.10 g, 12.87 mmol) was dissolved in $POCl_3$ (20 mL), followed by heating to 100 °C for overnight reaction. Complete reaction was determined by TLC, the reaction solution was directly concentrated to remove the $POCl_3$, then the oily crude product was slowly added dropwise to ice water (50 ml), the solution was stirred thoroughly, the pH value was adjusted to 8 with 2N sodium hydroxide aqueous solution, extraction was performed with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (PE: EA=10:1) to obtain a target compound (17c) (1,4-dichloropyridino[3,4-d]pyridazine) (0.92 g, yield: 32.63%. LCMS m/z=200.2 $[M+1]^+$).

Step 3: The compound (17c) (0.20 g, 1.00 mmol), (R)-1-methylpiperidine-3-amine (0.14 g, 1.20 mmol), and $Na_2CO_3$ (0.21 g, 1.99 mmol) were dissolved in dry DMF (3 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10:1) to obtain a target compound (17d) ((R)-4-chloro-N-(1-methylpiperidin-3-yl)pyridino[3,4-d]pyridazine-1-amine) (0.11 g, yield: 39.60%, LCMS m/z=278.2 $[M+1]^+$).

Step 4: The compound (17d) (0.05 g, 0.18 mmol), (2-hydroxy-4-(trifluoromethyl)phenyl)boronic acid (44.00 mg, 0.22 mmol), sodium carbonate (29.15 mg, 0.27 mmol), and $Pd(dppf)Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound 17 ((R)-2-(1-((1-methylpiperidin-3-yl)amino)pyridino[3,4-d]pyridazin-4-yl))-5-(trifluoromethyl)phenol) (0.01 g, yield: 13.77%, LCMS m/z=404.4 $[M+1]^+$).

Example 18: Synthesis of 2-(4-((trans)-4-(dimethylamino)cyclohexyl)amino)phthalazin-1-yl)-5-(trifluoromethyl)phenol

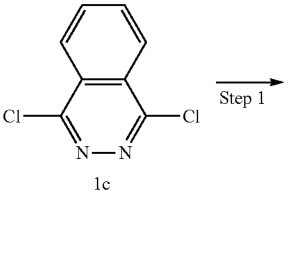

1c

-continued

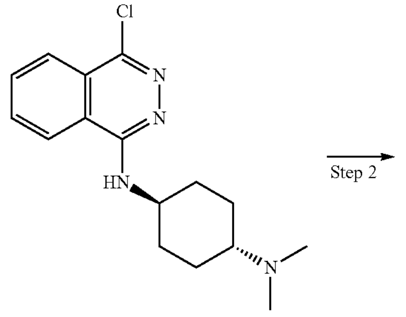

18b

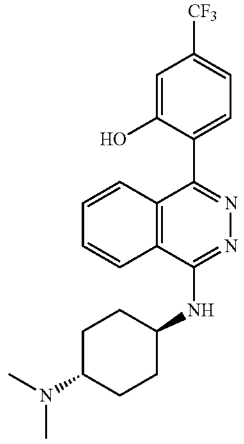

18

Step 1: The compound (1c) (0.20 g, 1.00 mmol), (trans)-$N^1$,$N^1$-dimethylcyclohexane-1,4-diamine (0.14 g, 1.00 mmol), and $Na_2CO_3$ (0.21 g, 1.99 mmol) were dissolved in dry DMF (3 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM:$CH_3OH$=10:1) to obtain a target compound (18b) (trans)-$N^1$-(4-chlorophthalazin-1-yl)-$N^4$,$N^4$-dimethylcyclohexane-1,4-diamine (0.04 g, yield: 13.15%, LCMS m/z=305.2 [M+1]$^+$).

Step 2: The compound (18b) (0.04 g, 0.13 mmol), (2-hydroxy-4-(trifluoromethyl)phenyl)boronic acid (35.00 mg, 0.17 mmol), sodium carbonate (22.10 mg, 0.21 mmol), and Pd(dppf)$Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound 18 2-(4-((trans)-4-(dimethylamino)cyclohexyl)amino)phthalazin-1-yl)-5-(trifluoromethyl)phenol (0.012 g, yield: 21.46%, LCMS m/z=431.5[M+1]$^+$).

Example 19: Synthesis of 2-(4-((cis)-4-(dimethylamino)cyclohexyl)amino)phthalazin-1-yl)-5-(trifluoromethyl)phenol

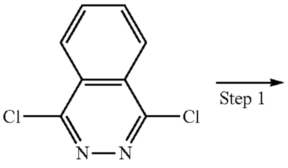

1c

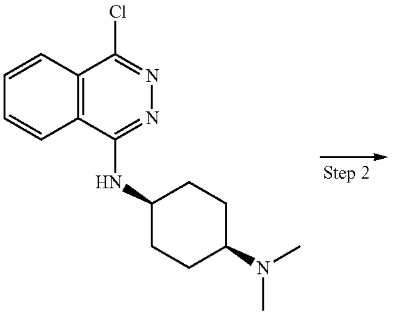

19b

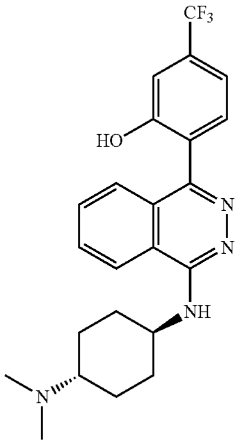

19

Step 1: The compound (1c) (0.20 g, 1.00 mmol), (cis)-$N^1$,$N^1$-dimethylcyclohexane-1,4-diamine (0.14 g, 1.00 mmol), and $Na_2CO_3$ (0.21 g, 1.99 mmol) were dissolved in dry DMF (3 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM:$CH_3OH$=10:1) to obtain a target compound (19b) (cis)-$N^1$-(4-chlorophthalazin-1-yl)-$N^4$,$N^4$-dimethylcyclohexane-1,4-diamine (0.05 g, yield, 16.45%, LCMS m/z=305.2 [M+1]$^+$).

Step 2: The compound (19b) (0.05 g, 0.13 mmol), (2-hydroxy-4-(trifluoromethyl)phenyl)boronic acid (35.00 mg, 0.17 mmol), sodium carbonate (22.10 mg, 0.21 mmol), and Pd(dppf)$Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound 19 2-(4-((cis)-4-(dimethylamino)cyclohexyl)amino)phthalazin-1-yl)-5-(trifluoromethyl)phenol (0.020 g, yield, 35.78%, LCMS m/z=431.5[M+1]$^+$).

Example 20: Synthesis of 2-(4-((2-hydroxy-2-methylpropyl)amino)phthalazin-1-yl)-5-(trifluoromethyl)phenol

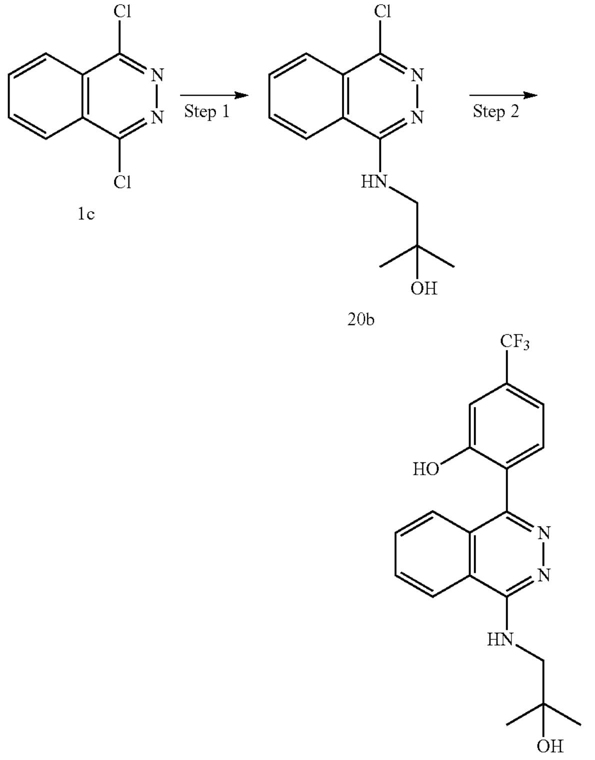

1c

20b

20

Step 1: The compound (1c) (0.20 g, 1.00 mmol), 1-amino-2-methylpropane-2-ol (0.14 g, 1.00 mmol), and $Na_2CO_3$ (0.21 g, 1.99 mmol) were dissolved in dry DMF (3 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10: 1) to obtain a target compound (20b) 1-((4-chlorophthalazin-1-yl)amino)-2-methylpropane-2-ol (0.05 g, yield: 19.92%, LCMS m/z=252.1 [M+1]$^+$).

Step 2: The compound (20b) (0.05 g, 0.20 mmol), (2-hydroxy-4-(trifluoromethyl)phenyl)boronic acid (50.00 mg, 0.24 mmol), sodium carbonate (42.40 mg, 0.40 mmol), and Pd(dppf)$Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound 20 2-(4-((2-hydroxy-2-methylpropyl)amino)phthalazin-1-yl)-5-(trifluoromethyl)phenol (0.01 g, yield: 11.60%, LCMS m/z=378.4[M+1]$^+$).

Example 21: Synthesis of 2-(4-((2-morpholinylethyl)amino)phthalazin-1-yl)-5-(trifluoromethyl)phenol

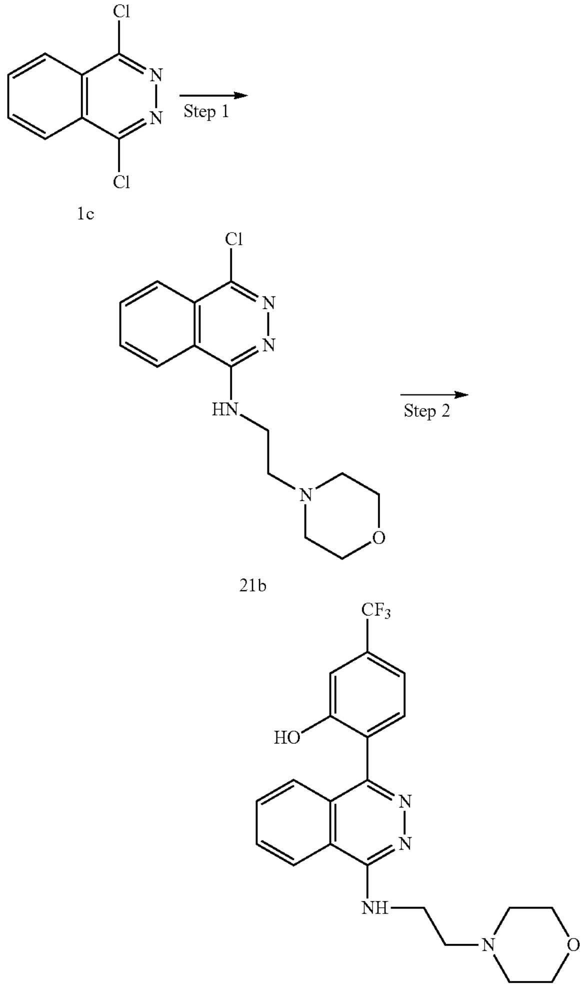

1c

21b

21

Step 1: The compound (1c) (0.20 g, 1.00 mmol), 2-morpholine ether-1-amine (0.12 g, 1.00 mmol), and $Na_2CO_3$ (0.21 g, 1.99 mmol) were dissolved in dry DMF (3 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10: 1) to obtain a target compound (21b) 4-chloro-N-(2-morpholinylethyl)phthalazine-1-amine (0.05 g, yield: 17.12%, LCMS m/z=293.1 $[M+1]^+$).

Step 2: The compound (21b) (0.05 g, 0.17 mmol), (2-hydroxy-4-(trifluoromethyl)phenyl)boronic acid (42.00 mg, 0.20 mmol), sodium carbonate (42.40 mg, 0.40 mmol), and Pd(dppf)$Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound 21 2-(4-((2-morpholinylethyl) amino)phthalazin-1-yl)-5-(trifluoromethyl)phenol (0.01 g, yield: 11.60%, LCMS m/z=419.4$[M+1]^+$)

Example 22: Synthesis of (R)-2-(4-(piperidin-3-ylamino)phthalazin-1-yl)-5-(trifluoromethyl)phenol

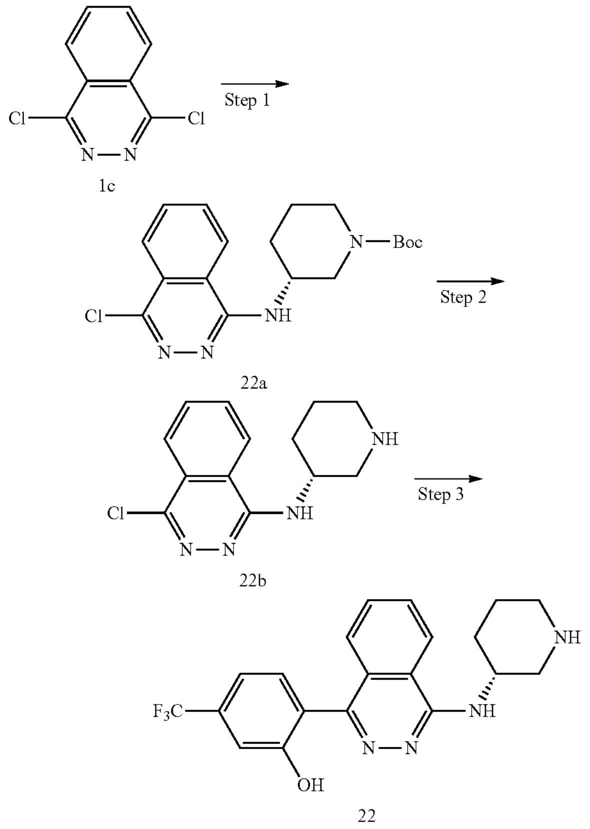

Step 1: The compound (1c) (0.20 g, 1.00 mmol), tert-butyl (R)-3-aminopiperidine-1-carboxylate (0.20 g, 1.00 mmol), and $Na_2CO_3$ (0.21 g, 1.99 mmol) were dissolved in dry DMF (10 mL), and the mixed system was heated in a 50 mL single-necked flask to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (EA:PE=1:1) to obtain a target compound (22a) (tert-butyl (R)-3-((4-chlorophthalazin-1-yl)amino)piperidine-1-carboxylate) (0.22 g, yield: 60.34%, LCMS m/z=363.2 $[M+1]^+$).

Step 2: The compound (22a) (0.22 g, 0.61 mmol) was dissolved in dichloromethane (10 mL), the solution was added to trifluoroacetic acid (2 mL), and reaction occurred at room temperature overnight. Complete reaction was determined by TLC, the reaction solution was directly concentrated to remove the trifluoroacetic acid, the pH value was adjusted to 8 with 2N sodium hydroxide aqueous solution, extraction was performed with ethyl acetate (30 mL×3), organic phases were combined, washed with saturated salt water (30 mL×3), dried with anhydrous sodium sulfate, and filtered, and the solvent was removed from the filtrate under reduced pressure to obtain a target compound (22b) ((R)-4-chloro-N-(piperidin-3-yl)phthalazine-1-amine) (0.11 g, yield: 69.05%, LCMS m/z=263.2 $[M+1]^+$).

Step 3: The compound (22b) (0.05 g, 0.19 mmol), (2-hydroxy-4-(trifluoromethyl)phenyl)boronic acid (44.00 mg, 0.22 mmol), sodium carbonate (29.15 mg, 0.27 mmol), and Pd(dppf)$Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL 3), dried with anhydrous sodium sulfate, and filtered, the solvent was removed from the filtrate under reduced pressure, and the residue was separated by column chromatography (DCM:$CH_3OH$=10:1) to obtain a target compound 22 ((R)-2-(4-(piperidin-3-ylamino)phthalazin-1-yl)-5-(trifluoromethyl)phenol) (0.03 g, yield: 40.59%, LCMS m/z=389.2 $[M+1]^+$).

Example 23: Synthesis of (R)-2-(4-((1-ethylpiperidin-3-yl)amino)phthalazin-1-yl)-5-(trifluoromethyl) phenol

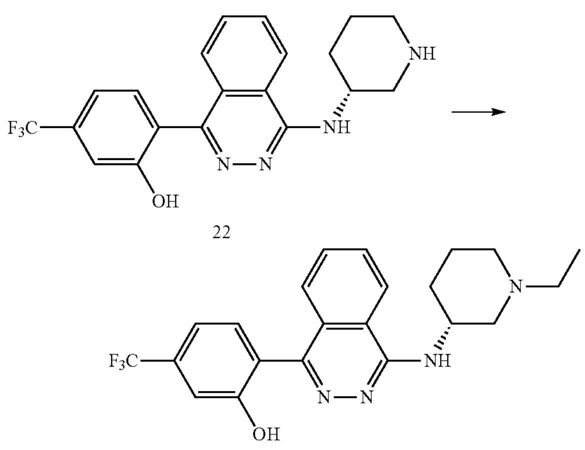

23

Step 1: The compound (22) (0.02 g, 0.051 mmol) and an acetaldehyde tetrahydrofuran solution (0.20 mL, 5.0 M) were dissolved in dry tetrahydrofuran (5 mL), two drops of acetic acid were added, the mixed system was placed in a 50 mL single-necked flask and stirred at room temperature for 1 hour, then $NaBH(OAc)_3$ was added, and the reaction continued for 3 hours. Complete reaction was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10:1) to obtain a target compound (23) ((R)-2-(4-((1-ethylpiperidin-3-yl)amino)phthalazin-1-yl)-5-(trifluoromethyl)phenol) (0.01 g, yield: 46.63%, LCMS m/z=417.4 $[M+1]^+$).

Example 24: (R)-2-(4-((1-methylpyrrolidin-3-yl) amino)phthalazin-1-yl)-5-(trifluoromethyl)phenol

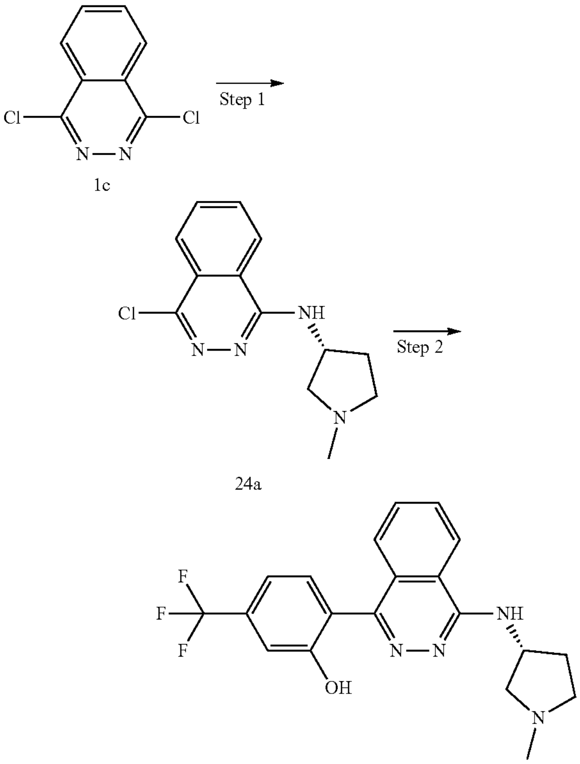

1c

24a

24

Step 1: The compound (1c) (0.20 g, 1.00 mmol), (R)-1-methylpyrrolidine-3-amine (0.11 g, 1.1 mmol), and $Na_2CO_3$ (0.21 g, 2.0 mmol) were dissolved in dry DMF (2 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10:1) to obtain a target compound (24a) ((R)-4-chloro-N-(1-methylpyrrolidin-3-yl)phthalazine-1-amine) (0.06 g, yield: 21.6%, LCMS m/z=263.4$[M+1]^+$).

Step 2: The compound (24a) (27 mg, 0.10 mmol), (2-hydroxy-4-(trifluoromethyl)phenyl)boronic acid (0.045 g, 0.217 mmol), sodium carbonate (42 mg, 0.40 mmol), and $Pd(dppf)Cl_2$ (5 mg, 0.007 mmol) were added to 5 mL of a mixed solvent of dioxane and water (v/v=4:1) at room temperature, followed by nitrogen displacement 3 times and heating to 110 °C for reaction for 16 hours. The reaction solution was spin-dried and then directly separated by silica gel column chromatography (DCM:$CH_3OH$=10:1) to obtain a compound 24 ((R)-2-(4-((1-methylpyrrolidin-3-yl)amino) phthalazin-1-yl)-5-(trifluoromethyl)phenol) (30 mg, yield: 71.24%.

LCMS m/z=389.4 $[M+1]^+$)

Example 25: (R)-2-(4-((1-ethylpyrrolidin-3-yl) amino)phthalazin-1-yl)-5-(trifluoromethyl)phenol

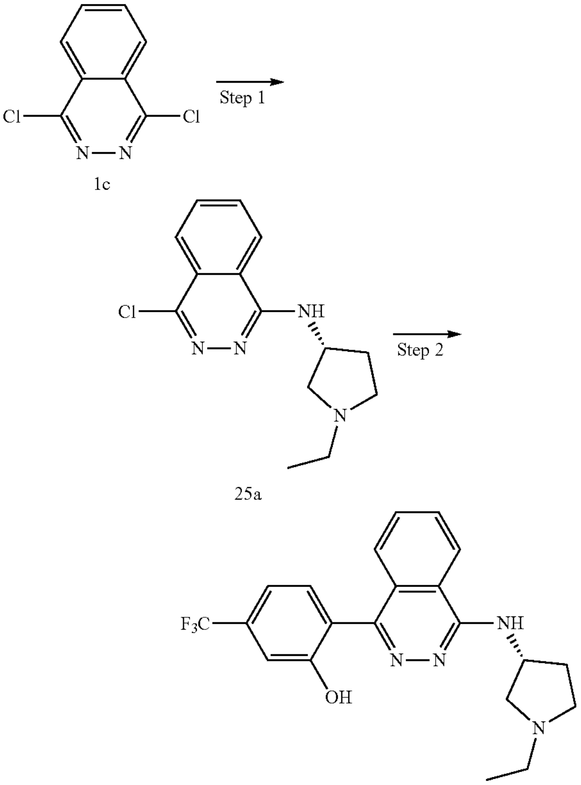

1c

25a

25

Step 1: The compound (1c) (0.20 g, 1.00 mmol), (R)-1-ethylpyrrolidine-3-amine (0.14 g, 1.1 mmol), and $Na_2CO_3$ (0.21 g, 2.0 mmol) were dissolved in dry DMF (2 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10:

1) to obtain a target compound (25a) ((R)-4-chloro-N-(1-ethylpyrrolidin-3-yl)phthalazine-1-amine) (0.10 g, yield: 36.23%, LCMS m/z=277.4[M+1]+).

Step 2: The compound (25a) (28 mg, 0.10 mmol), (2-hydroxy-4-(trifluoromethyl)phenyl)boronic acid (0.045 g, 0.217 mmol), sodium carbonate (42 mg, 0.40 mmol), and Pd(dppf)$Cl_2$ (5 mg, 0.007 mmol) were added to 5 mL of a mixed solvent of dioxane and water (v/v=4:1) at room temperature, followed by nitrogen displacement 3 times and heating to 110 °C for reaction for 16 hours. The reaction solution was spin-dried and then directly separated by silica gel column chromatography (DCM:$CH_3OH$=10:1) to obtain a compound 25 ((R)-2-(4-((1-ethylpyrrolidin-3-yl)amino)phthalazin-1-yl)-5-(trifluoromethyl)phenol (20 mg, yield: 49.75%, LCMS m/z=403.4 [M+1]+)

Example 27: (R)-2-(4-(((1-ethylpyrrolidin-2-yl)methyl)amino)phthalazin-1-yl)-5-(trifluoromethyl)phenol

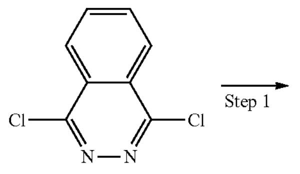

1c

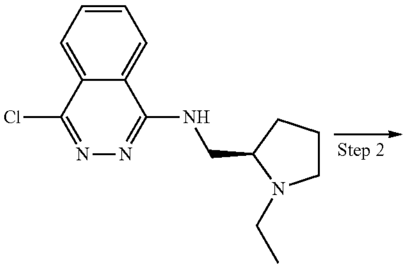

27a

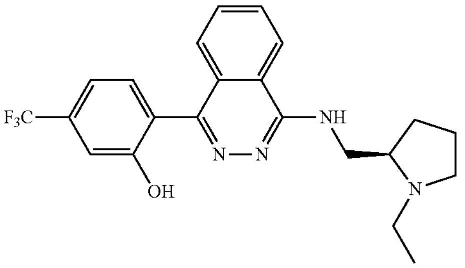

27

Step 1: The compound (1c) (0.20 g, 1.00 mmol), (R)-(1-ethylpyrrolidin-2-yl)methylamine (0.11 g, 1.1 mmol), and $Na_2CO_3$ (0.21 g, 2.0 mmol) were dissolved in dry DMF (2 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM:$CH_3OH$=10:1) to obtain a target compound (27a) ((R)-4-chloro-N-((1-ethylpyrrolidin-2-yl)methyl)phthalazine-1-amine) (0.08 g, yield: 27.5%, LCMS m/z=291.4[M+1]+).

Step 2: The compound (27a) (30 mg, 0.10 mmol), (2-hydroxy-4-(trifluoromethyl)phenyl)boronic acid (0.045 g, 0.217 mmol), sodium carbonate (42 mg, 0.40 mmol), and Pd(dppf)$Cl_2$ (5 mg, 0.007 mmol) were added to 5 mL of a mixed solvent of dioxane and water (v/v=4:1) at room temperature, followed by nitrogen displacement 3 times and heating to 110 °C for reaction for 16 hours. The reaction solution was spin-dried and then directly separated by silica gel column chromatography (DCM:$CH_3OH$=10:1) to obtain a compound 27 ((R)-2-(4-(((1-ethylpyrrolidin-2-yl)methyl)amino)phthalazin-1-yl)-5-(trifluoromethyl)phenol (10 mg, yield: 23.98%, LCMS m/z=417.4 [M+1]+)

Example 29: Synthesis of (R)-2-(4-((6,7-dihydro-5H-cyclopenta[b]pyridin-5-yl)amino)phthalazin-1-yl)-5-(trifluoromethyl)phenol

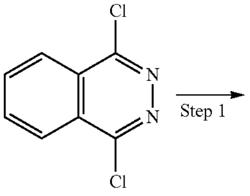

1c

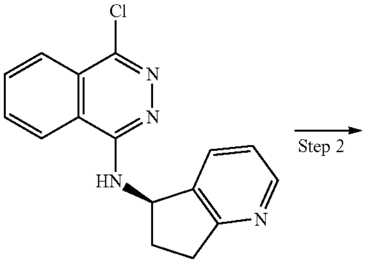

29b

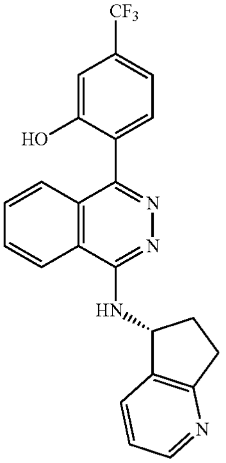

29

Step 1: The compound (1c) (0.20 g, 1.00 mmol), (R)-6,7-dihydro-5H-cyclopenta[b]pyridine-5-amine (0.13 g, 1.00 mmol), and $Na_2CO_3$ (0.21 g, 1.99 mmol) were dissolved in dry DMF (3 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM:$CH_3OH$=10:1) to obtain a target compound (29b) (R)-4-chloro-N-(6,7-dihydro-5H-cyclopenta[b]pyridin-5-yl)phthalazine-1-amine (0.06 g. yield: 20.27%. LCMS m/z=297.8 $[M+1]^+$).

Step 2: The compound (29b) (0.06 g, 0.20 mmol), (2-hydroxy-4-(trifluoromethyl)phenyl)boronic acid (50.00 mg, 0.24 mmol), sodium carbonate (42.40 mg, 0.40 mmol), and Pd(dppf)$Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound 29 (R)-2-(4-((6,7-dihydro-5H-cyclopenta[b]pyridin-5-yl)amino)phthalazin-1-yl)-5-(trifluoromethyl)phenol (0.01 g, yield: 11.84%, LCMS m/z=423.5$[M+1]^+$).

Example 30: Synthesis of (S)-2-(4-((6,7-dihydro-5H-cyclopenta[b]pyridin-5-yl)amino)phthalazin-1-yl)-5-(trifluoromethyl)phenol

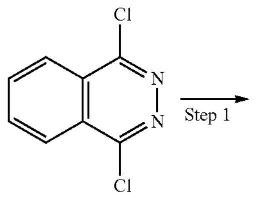

1c

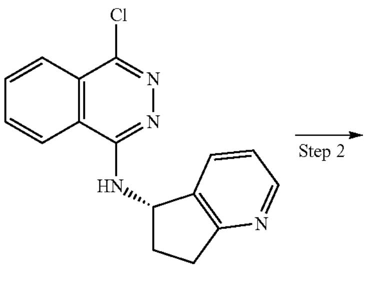

30b

-continued

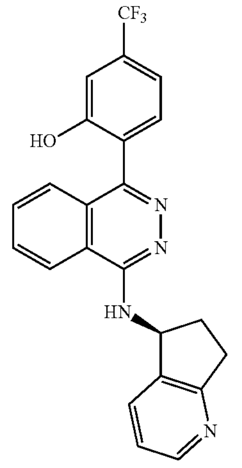

30

Step 1: The compound (1c) (0.20 g, 1.00 mmol), (S)-6,7-dihydro-5H-cyclopenta[b]pyridine-5-amine (0.13 g, 1.00 mmol), and $Na_2CO_3$ (0.21 g, 1.99 mmol) were dissolved in dry DMF (3 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM:$CH_3OH$=10:1) to obtain a target compound (30b) (S)-4-chloro-N-(6,7-dihydro-5H-cyclopenta[b]pyridin-5-yl)phthalazine-1-amine (0.05 g, yield: 16.83%, LCMS m/z=297.8 $[M+1]^+$).

Step 2: The compound (30b) (0.06 g, 0.17 mmol), (2-hydroxy-4-(trifluoromethyl)phenyl)boronic acid (42.00 mg, 0.20 mmol), sodium carbonate (42.40 mg, 0.40 mmol), and Pd(dppf)$Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound 30 (S)-2-(4-((6,7-dihydro-5H-cyclopenta[b]pyridin-5-yl)amino)phthalazin-1-yl)-5-(trifluoromethyl)phenol (0.01 g, yield: 13.94%, LCMS m/z=423.5[M+1]j).

Example 31: (R)-2-(4-((1-methylpiperidin-3-yl)amino)phthalazin-1-yl)phenol

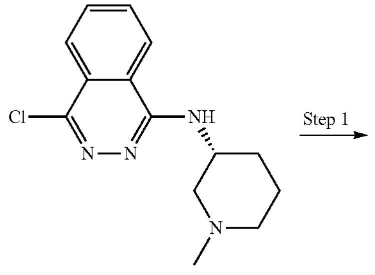

1d

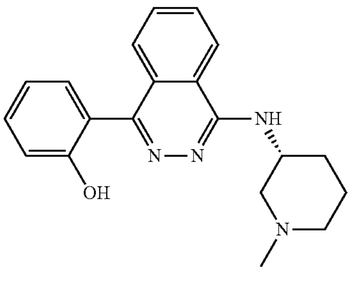

31

Step 1: The compound (1d) (50 mg, 0.18 mmol), (2-hydroxyphenyl)boric acid (50 mg, 0.36 mmol), sodium carbonate (60 mg, 0.57 mmol), and Pd(dppf)$Cl_2$ (5 mg, 0.007 mmol) were added to 5 mL of a mixed solvent of dioxane and water (v/v=4:1), followed by nitrogen displacement 3 times and heating to 110 °C for reaction for 16 hours. The reaction solution was spin-dried and then directly separated by silica gel column chromatography (DCM:$CH_3OH$=10:1) to obtain a compound 31 ((R)-2-(4-((1-methylpiperidin-3-yl)amino)phthalazin-1-yl)phenol (20 mg, yield: 33.23%, LCMS m/z=335.4 $[M+1]^+$)

Example 32: Synthesis of (R)-1-(3-((4-(2-hydroxy-4-(trifluoromethyl)phenyl)phthalazin-1-yl)amino)piperidin-1-yl)ethane-1-one

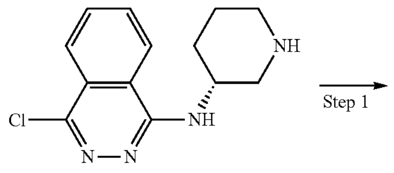

22b

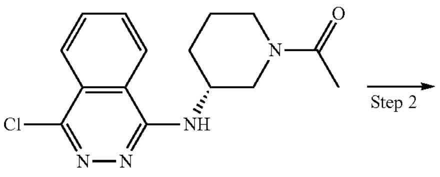

32a

-continued

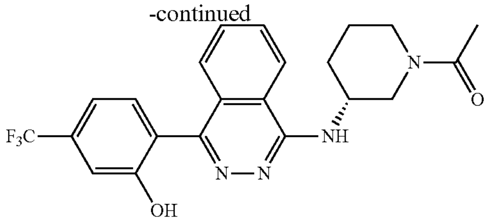

32

Step 1: The compound (22b) (0.01 g, 0.038 mmol) and triethylamine (77.03 mg, 0.76 mmol) were dissolved in dichloromethane (5 mL), acetyl chloride (29.88 mg, 0.038 mmol) was added dropwise, and reaction occurred at room temperature for 0.5 hour. Complete reaction was determined by TLC, the reaction solution was added to water (20 ml), stirred thoroughly, and extracted with DCM (20 mL×3), organic phases were combined, washed with saturated salt water (10 mL×3), dried with anhydrous sodium sulfate, and filtered, the solvent was removed from the filtrate under reduced pressure, and the residue was separated by column chromatography (EA:PE=1:3) to obtain a target compound (32a) ((R)-1-(3-((4-chlorophthalazin-1-yl)amino)piperidin-1-yl)ethane-1-one) (0.06 g, yield: 51.72%, LCMS m/z=305.2 $[M+1]^+$).

Step 2: The compound (32a) (0.05 g, 0.16 mmol), (2-hydroxy-4-(trifluoromethyl)phenyl)boronic acid (44.00 mg, 0.22 mmol), sodium carbonate (29.15 mg, 0.27 mmol), and Pd(dppf)$Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound 32 ((R)-1-(3-((4-(2-hydroxy-4-(trifluoromethyl)phenyl)phthalazin-1-yl)amino)piperidin-1-yl)ethane-1-one) (0.02 g, yield: 28.32%, LCMS m/z=431.2 $[M+1]^+$).

Example 33: Synthesis of isomers 1 and 2 of 2-(4-((-3-hydroxycyclohexyl)amino)phthalazin-1-yl)-5-(trifluoromethyl)phenol

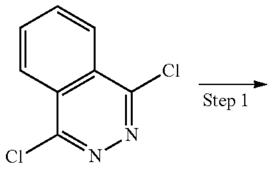

1c

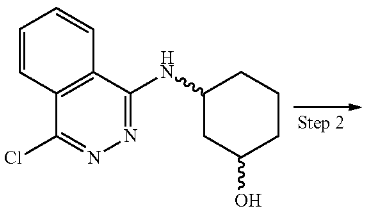

33a

-continued

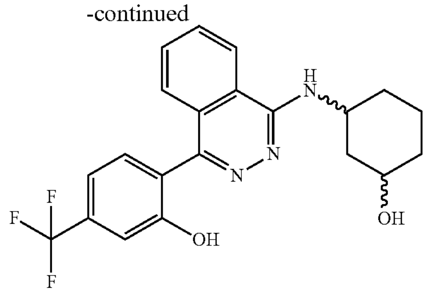

33

-continued

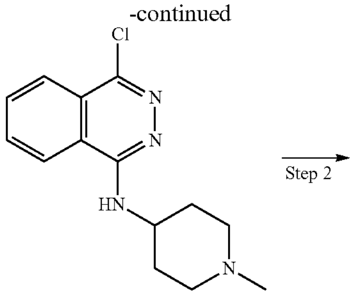

35b

Step 1: The compound (1c) (0.28 g, 1.39 mmol), 3-aminocyclohexanol (0.16 g, 1.39 mmol), and $Na_2CO_3$ (0.44 g, 4.17 mmol) were dissolved in dry DMAc (2.5 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10:1) to obtain a target compound (33a) 3-((4-chlorophthalazin-1-yl)amino)cyclohexan-1-ol (0.35 g, yield: 90.66%, LCMS m/z=278.2 $[M+1]^+$).

Step 2: The compound (33a) (0.05 g, 0.18 mmol), (2-hydroxy-4-(trifluoromethyl)phenyl)boronic acid (0.048 g, 0.23 mmol), sodium carbonate (0.057 g, 0.54 mmol), and Pd(dppf)$Cl_2$ (15.00 mg, 0.02 mmol) were added to 5 mL of a mixed solvent of dioxane and water (v/v=4:1), followed by nitrogen displacement 3 times and heating to 110 °C for reaction for 16 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=20:1) to obtain an isomer 1 (compound 33) (developing agent DCM: $CH_3OH$=10:1, Rf=0.2, 15 mg, yield; 20.66%. LC-MS m/z=404.5 $[M+1]^+$) and an isomer 2 (compound 34) (developing agent DCM: $CH_3OH$=10:1, Rf=0.3, 15 mg, yield: 20.66%, LCMS m/z=404.5 $[M+1]^+$) of a compound (2-(4-((-3-hydroxycyclohexyl)amino)phthalazin-1-yl)-5-(trifluoromethyl)phenol).

Example 35: Synthesis of 2-(4-((1-methylpiperidin-4-yl)amino)phthalazin-1-yl)-5-(trifluoromethyl)phenol

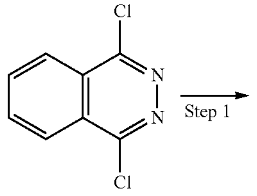

1c

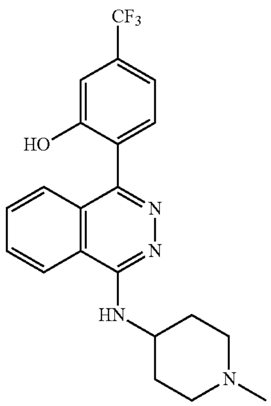

35

Step 1. The compound (1c) (0.20 g, 1.00 mmol), 1-methylpiperidine-4-amine (0.12 g, 1.00 mmol), and $Na_2CO_3$ (0.21 g, 1.99 mmol) were dissolved in dry DMF (3 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10:1) to obtain a target compound (35b) 4-chloro-N-(1-methylpiperidin-4-yl)phthalazine-1-amine (0.06 g, yield: 21.73%, LCMS m/z=277.2 $[M+1]^+$).

Step 2: The compound (35b) (0.03 g, 0.21 mmol), (2-hydroxy-4-(trifluoromethyl)phenyl)boronic acid (25.00 mg, 0.24 mmol), sodium carbonate (21.20 mg, 0.20 mmol), and Pd(dppf)$Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound 35 2-(4-((1-methylpiperidin-4-yl)amino)phthalazin-1-yl)-5-(trifluoromethyl)phenol (0.02 g, yield: 23.69%, LCMS m/z=403.3$[M+1]^+$).

Example 36: Synthesis of (R)-2-(1-methyl-7-((1-methylpiperidin-3-yl)amino)-1H-imidazo[4,5-d]pyridazin-4-yl)-5-(trifluoromethyl)phenol

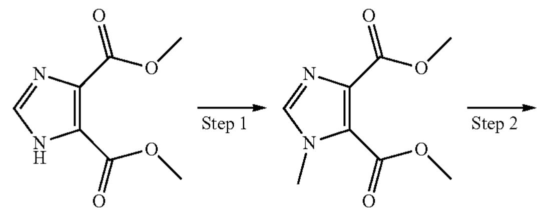

36a 36b

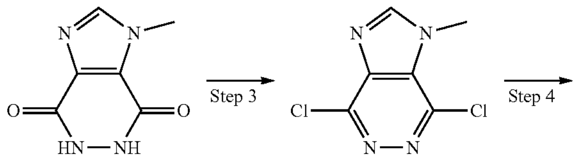

36c 36d

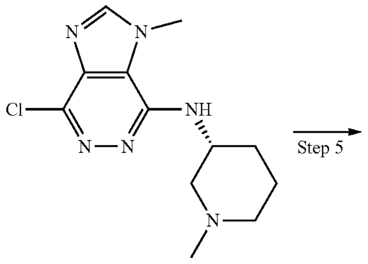

36e

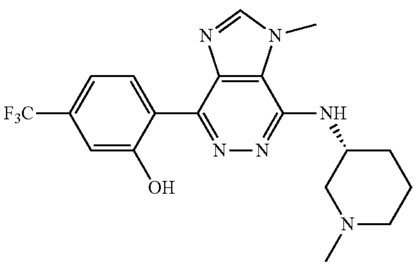

36

Step 1: A compound 1H-imidazole-4,5-dimethyl dicarboxylate (36a) (3.0 g, 16.29 mmol), iodomethane (3.47 g, 24.43 mmol), and potassium carbonate (3.38 g, 24.43 mmol) were dissolved in DMF (20 mL), followed by heating to 60 °C and reaction for 3 hours. Complete reaction was determined by TLC, the reaction solution was added to water (50 ml) and extracted with ethyl acetate (30 mL/3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound (36b) (1-methyl-1H-imidazol-4,5-dimethyl dicarboxylate) (0.80 g, yield: 24.78%, LCMS m/z=199.2 $[M+1]^+$).

Step 2: The compound 1-methyl-1H-imidazol-4,5-dimethyl dicarboxylate (36b) (0.8 g, 4.04 mmol) and $N_2H_4 \cdot H_2O$ (0.61 g, 12.12 mmol) were dissolved in acetic acid (5 mL), followed by heating to 120 °C for overnight reflux. Complete reaction was determined by TLC, the reaction solution was directly concentrated, then water (30 ml) was added to disperse the solid, filtration was performed, and filter cakes were drained and dried in vacuum overnight to obtain a target compound (36c) (1-methyl-5,6-dihydro-1H-imidazo[4,5-d]pyridazine-4,7-dione) (0.40 g, yield: 59.59%, LCMS m/z=167.2 $[M+1]^+$).

Step 3: The compound (36c) (0.40 g, 2.41 mmol) was dissolved in $POCl_3$ (10 mL), followed by heating to 100 °C for overnight reaction. Complete reaction was determined by TLC, the reaction solution was directly concentrated to remove the $POCl_3$, then the oily crude product was slowly added dropwise to ice water (50 ml), the solution was stirred thoroughly, the pH value was adjusted to 8 with 2N sodium hydroxide aqueous solution, extraction was performed with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (PE:EA=5:1) to obtain a target compound (36d) (4,7-dichloro-1-methyl-1H-imidazo[4,5-d]pyridazine) (0.40 g, yield: 81.75%, LCMS m/z=203.2 $[M+1]^+$).

Step 4: The compound (36d) (0.40 g, 1.97 mmol), (R)-1-methylpiperidine-3-amine (0.27 g, 2.36 mmol), and $Na_2CO_3$ (0.21 g, 1.97 mmol) were dissolved in dry DMF (5 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM:$CH_3OH$=10:1) to obtain a target compound (36e) ((R)-4-chloro-1-methyl-N-(1-methylpiperidin-3-yl)-1H-imidazo[4,5-d]pyridazine-7-amine) (0.05 g, yield: 9.04%, LCMS m/z=281.2 $[M+1]^+$).

Step 5: The compound (36e) (0.04 g, 0.14 mmol), (2-hydroxy-4-(trifluoromethyl)phenyl)boronic acid (35.00 mg, 0.17 mmol), sodium carbonate (22.10 mg, 0.22 mmol), and $Pd(dppf)Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound 36 ((R)-2-(1-methyl-7-((1-methylpiperidin-3-yl)amino)-1H-imidazo[4,5-d]pyridazin-4-yl)-5-(trifluoromethyl)phenol (0.020 g, yield: 35.15%, LCMS m/z=407.4 $[M+1]^+$).

Example 37: Synthesis of (R)-2-(1-methyl-4-((1-methylpiperidin-3-yl)amino)-1H-imidazo[4,5-d]pyridazin-7-yl)-5-(trifluoromethyl)phenol

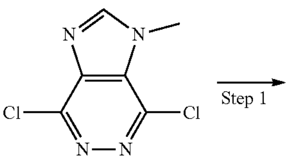

36d

-continued

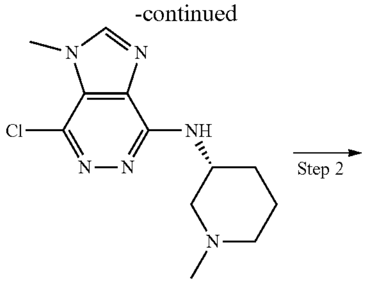

37a

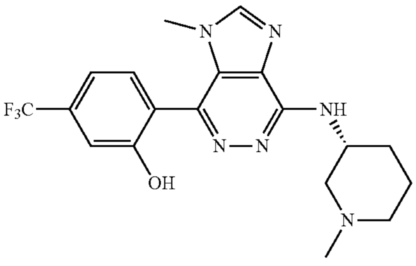

37

Step 1: The compound (36d) (0.40 g, 1.97 mmol), (R)-1-methylpiperidine-3-amine (0.27 g, 2.36 mmol), and $Na_2CO_3$ (0.21 g, 1.97 mmol) were dissolved in dry DMF (5 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10:1) to obtain a target compound (37a) ((R)-7-chloro-1-methyl-N-(1-methylpiperidin-3-yl)-1H-imidazo[4,5-d]pyridazine-4-amine) (0.10 g, yield: 18.08%, LCMS m/z=281.2 $[M+1]^+$).

Step 2: The compound (37a) (0.05 g, 0.18 mmol), (2-hydroxy-4-(trifluoromethyl)phenyl)boronic acid (44.00 mg, 0.22 mmol), sodium carbonate (22.10 mg, 0.22 mmol), and $Pd(dppf)Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound 37 ((R)-2-(1-methyl-4-((1-methylpiperidin-3-yl)amino)-1H-imidazo[4,5-d]pyridazin-7-yl)-5-(trifluoromethyl)phenol (0.030 g, yield: 41.04%, LCMS m/z=407.4 $[M+1]^+$).

Example 38: Synthesis of (R)-2-(4-((1-methylpiperidin-3-yl)amino)-7-(trifluoromethyl)phthalazin-1-yl)-5-(trifluoromethyl)phenol

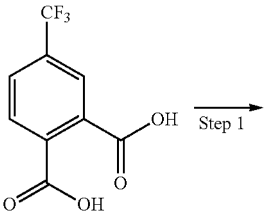

38a

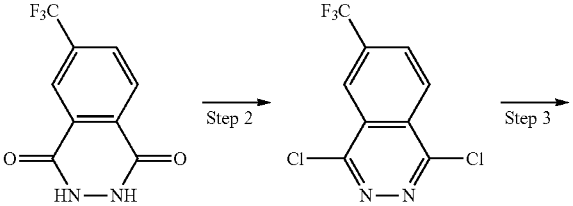

38b 38c

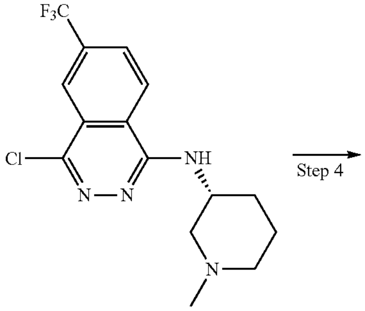

38d

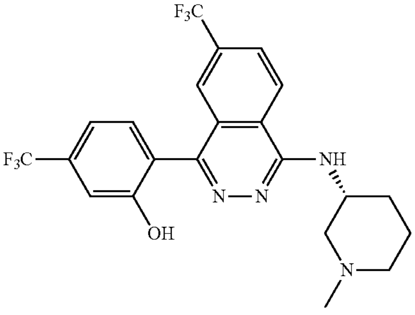

38

Step 1: A compound 4-(trifluoromethyl)phthalic acid (38a) (2.0 g, 8.54 mmol) was dissolved in 15 ml of thionyl chloride, 2 drops of dry DMF was added, heating was performed until reflux reaction for 2 hours, the reaction solution was concentrated, the concentrate was repeatedly dissolved with toluene (20 mL), then the solution was concentrated, the residue was dissolved in acetic acid (30 mL), and $N_2H_4 \cdot H_2O$ (1.85 g, 37.00 mmol) was added, followed by heating to 120 °C for overnight reflux. The reaction solution was directly concentrated, then water (20 ml) was added to disperse the solid, filtration was performed, and filter cakes were drained and dried in vacuum overnight to obtain a target compound 38b (6-(trifluoromethyl)-2,3-dihydrophthalazine-1,4-dione) (0.70 g, yield: 35.61%, LCMS m/z=231.2 $[M+1]^+$).

Step 2: The compound (38b) (0.70 g, 3.04 mmol) was dissolved in $POCl_3$ (10 mL), followed by heating to 100 °C for overnight reaction. Complete reaction was determined by TLC, the reaction solution was directly concentrated to remove the $POCl_3$, then the oily crude product was slowly added dropwise to ice water (50 ml), the solution was stirred thoroughly, the pH value was adjusted to 8 with 2N sodium hydroxide aqueous solution, extraction was performed with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (PE: EA=10:1) to obtain a target compound (38c) (1,4-dichloro-6-(trifluoromethyl)phthalazine) (0.52 g, yield: 64.02%, LCMS m/z=267.2 $[M+1]^+$).

Step 3: The compound (38c) (0.22 g, 0.82 mmol). (R)-1-methylpiperidine-3-amine (0.12 g, 1.04 mmol), and $Na_2CO_3$ (0.20 g, 1.89 mmol) were dissolved in dry DMF (2 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10:1) to obtain a mixture of target compounds (38d) and (39d) (0.15 g, yield: 52.81%, LCMS m/z=345.2 $[M+1]^+$).

Step 4: The mixture of compounds (38d) and (39d) (0.10 g, 0.29 mmol), (2-hydroxy-4-(trifluoromethyl)phenyl)boronic acid (0.074 g, 0.357 mmol), sodium carbonate (0.058 g, 0.55 mmol), and $Pd(dppf)Cl_2$ (20.00 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL 3), organic phases were combined, washed with saturated salt water (30 mL×3), dried with anhydrous sodium sulfate, and filtered, the solvent was removed from the filtrate under reduced pressure, and the residue was separated by PTLC (DCM:$CH_3OH$=10:1) to obtain a target compound 38 ((R)-2-(4-((1-methylpiperidin-3-yl)amino)-7-(trifluoromethyl)phthalazin-1-yl)-5-(trifluoromethyl)phenol (0.01 g, yield: 7.33%, LCMS m/z=471.4 $[M+1]^+$).

Example 39: Synthesis of (R)-2-(4-((1-methylpiperidin-3-yl)amino)-6-(trifluoromethyl)phthalazin-1-yl)-5-(trifluoromethyl)phenol

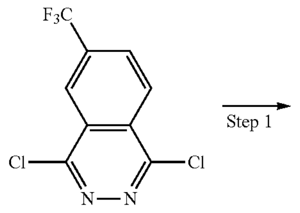

38c

-continued

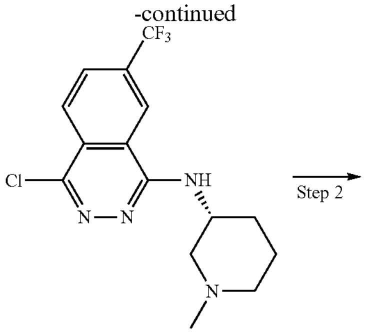

39d

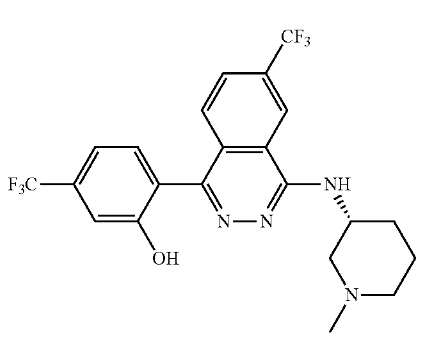

39

Step 1: The compound (38c) (0.22 g, 0.82 mmol), (R)-1-methylpiperidine-3-amine (0.12 g, 1.04 mmol), and $Na_2CO_3$ (0.20 g, 1.89 mmol) were dissolved in dry DMF (2 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10:1) to obtain a mixture of target compounds (38d) and (39d) (0.15 g, yield: 52.81%, LCMS m/z=345.2 $[M+1]^+$).

Step 2: The mixture of compounds (38d) and (39d) (0.10 g, 0.29 mmol), (2-hydroxy-4-(trifluoromethyl)phenyl)boronic acid (0.074 g, 0.357 mmol), sodium carbonate (0.058 g, 0.55 mmol), and $Pd(dppf)Cl_2$ (20.00 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 ml×3), organic phases were combined, washed with saturated salt water (30 mL×3), dried with anhydrous sodium sulfate, and filtered, the solvent was removed from the filtrate under reduced pressure, and the residue was separated by PTLC (DCM:$CH_3OH$=10:1) to obtain a target compound 39 (R)-2-(4-((1-methylpiperidin-3-yl)amino)-6-(trifluoromethyl)phthalazin-1-yl)-5-(trifluoromethyl)phenol (0.007 g, yield: 5.13%, LCMS m/z=471.4 $[M+1]^+$).

Example 40: Synthesis of (R)-5-methyl-2-(4-((1-methylpiperidin-3-yl)amino)phthalazin-1-yl)phenol

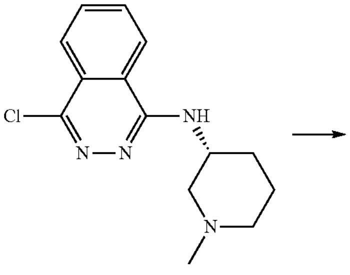

1d

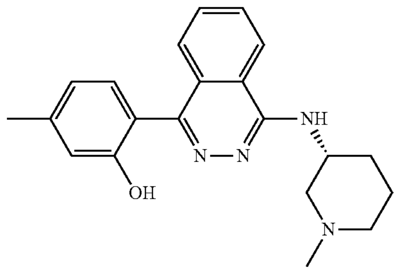

40

Step: The compound (1d) (0.05 g, 0.18 mmol), (2-hydroxy-4-methylphenyl)boric acid (40.77 mg, 0.27 mmol), sodium carbonate (42.40 mg, 0.40 mmol), and Pd(dppf)$Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound 40 (R)-5-methyl-2-(4-((1-methylpiperidin-3-yl)amino) phthalazin-1-yl)phenol (0.02 g, yield: 23.69%, LCMS m/z=348.31M+1|+).

Example 41: Synthesis of (R)-2-(4-((1-methylpiperidin-3-yl)amino)phthalazin-1-yl)-5-(trifluoromethoxy)phenol

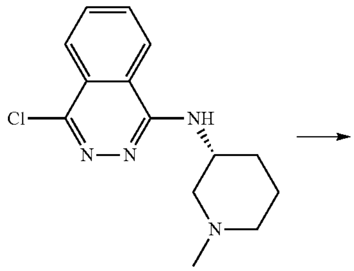

1d

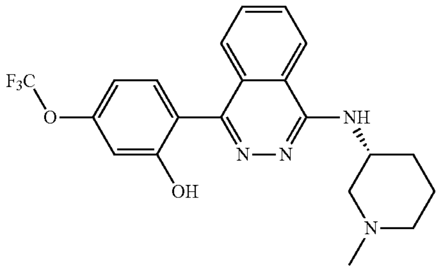

41

Step: The compound (1d) (0.05 g, 0.18 mmol), (2-hydroxy-4-(trifluoromethoxy)phenyl)boronic acid (59.94 mg, 0.27 mmol), sodium carbonate (42.40 mg, 0.40 mmol), and Pd(dppf)$Cl_2$ (19.75 mg, 0.027 mmol) were added to 5 mL of a mixed solvent of dioxane and water (v/v=4:1), followed by nitrogen displacement 3 times and heating to 110° for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound 41 (R)-2-(4-((1-methylpiperidin-3-yl)amino)phthalazin-1-yl)-5-(trifluoromethoxy)phenol (0.02 g, yield: 26.52%, LCMS m/z=419.2[M+1]$^+$).

Example 43: (R)-(1-(2-hydroxy-4-(trifluoromethyl) phenyl)-4-((1-methylpiperidin-3-yl)amino)phthalazin-6-yl)dimethylphosphine oxide

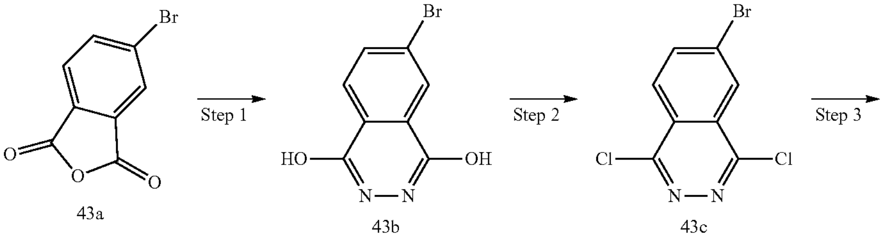

43a 43b 43c

-continued

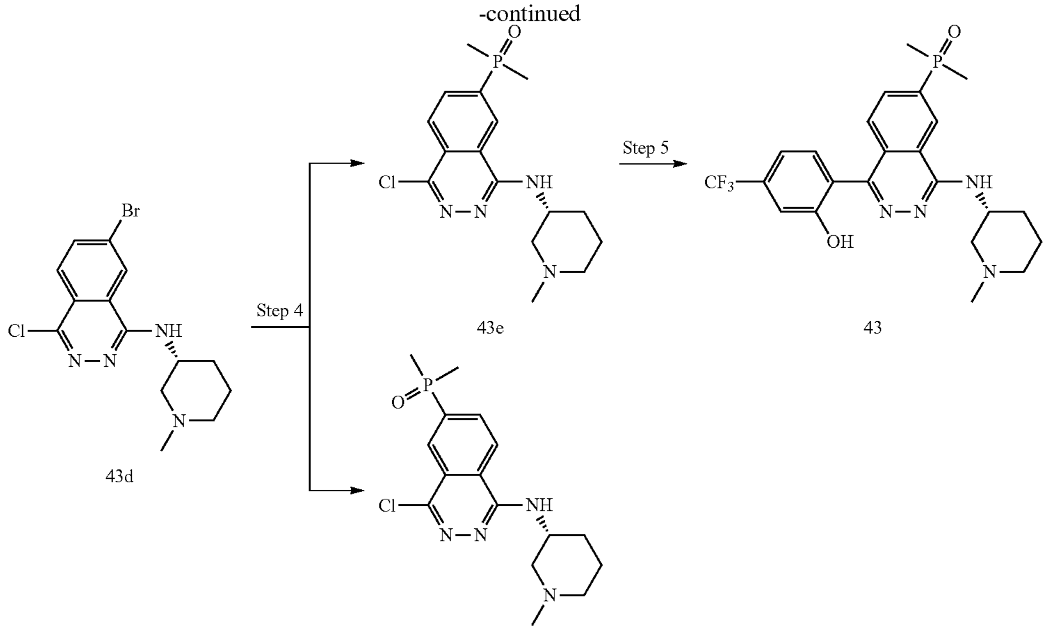

43d 43e 43f 43

Step 1: A compound (43a) (1.0 g, 4.44 mmol) and $N_2H_4 \cdot H_2O$ (2.5 g, 41.1 mmol, 80% wt) were dissolved in acetic acid (20 mL), followed by heating to 120 °C for overnight reflux. Complete reaction was determined by TLC, the reaction solution was directly filtered, washing with water (20 mL×3) was performed, and filter cakes were drained and dried in vacuum to obtain a target compound 43b (6-bromophthalazine-1,4-diol) (1.0 g, yield: 94.34%, LCMS m/z=241.1 $[M+1]^+$).

Step 2: The compound (43b) (0.70 g, 2.9 mmol) was dissolved in $POCl_3$ (4 mL), followed by heating to 110 °C for overnight reaction. Complete reaction was determined by TLC, the reaction solution was concentrated to one tenth of the volume, then slowly added dropwise to ice water (20 ml), and stirred thoroughly, the pH value was adjusted to 8 with 2N sodium hydroxide aqueous solution, extraction was performed with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (PE:EA=20:1) to obtain a target compound 43c (6-bromo-1,4-dichlorophthalazine) (0.61 g, yield: 75.68%, LCMS m/z=277.0 $[M+1]^+$).

Step 3: The compound (43c) (0.60 g, 2.16 mmol), (R)-1-methylpiperidine-3-amine (0.25 g, 2.16 mmol), and $Na_2CO_3$ (0.43 g, 4.00 mmol) were dissolved in dry DMF (4 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10:1) to obtain a target compound (43d) ((R)-7-bromo-4-chloro-N-(1-methylpiperidin-3-yl)phthalazine-1-amine) (0.50 g, yield: 65.09%, LCMS m/z=355.1 $[M+1]^+$).

Step 4: The compound (43d) (0.40 g, 1.12 mmol), dimethylphosphine oxide (87.4 mg, 1.12 mmol), palladium acetate (25 mg, 0.11 mmol), Xantphos (92 mg, 0.16 mmol), and anhydrous potassium phosphate (467 mg, 2.2 mmol) were added to dry DMF (6 mL) at room temperature, followed by argon displacement 3 times and heating to 150 °C for reaction for 3 hours. The reaction solution was spin-dried and then directly separated by silica gel column chromatography (DCM: $CH_3OH$=10:1) to obtain a compound 43e ((R)-(1-chloro-4-((1-methylpiperazin-3-yl)amino)phthalazin-6-yl)dimethylphosphine oxide) (32 mg, yield: 7.7%, LCMS m/z=353.2 $[M+1]^+$) and a compound 43f (R)-4-chloro-1-((1-methylpiperazin-3-yl)amino)phthalazin-6-yl)dimethylphosphine oxide (30 mg, yield: 7.6%, LCMS m/z=353.2 $[M+1]^+$).

Step 5: The compound (43e) (30 mg, 0.08 mmol), (2-hydroxy-4-(trifluoromethyl)phenyl)boronic acid (35 mg, 0.17 mmol), sodium carbonate (26 mg, 0.24 mmol), and Pd(dppf) $Cl_2$ (5 mg, 0.007 mmol) were added to 5 mL of a mixed solvent of dioxane and water (v/v=4:1), followed by nitrogen displacement 3 times and heating to 110 °C for reaction for 16 hours. The reaction solution was spin-dried and then directly separated by silica gel column chromatography (DCM:$CH_3OH$=10:1) to obtain a compound 43 (R)-(1-(2-hydroxy-4-(trifluoromethyl)phenyl)-4-((1-methylpiperidin-3-yl)amino)phthalazin-6-yl)dimethylphosphine oxide) (0.01 g, yield: 24.59%, LCMS m/z=479.6 $[M+1]^+$).

Example 44: Synthesis of (R)-5-fluoro-2-(4-((1-methylpiperidin-3-yl)amino)phthalazin-1-yl)phenol

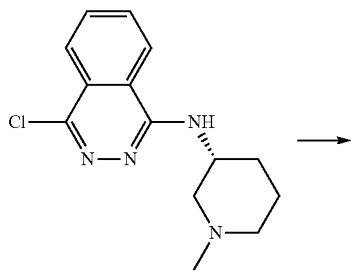

1d

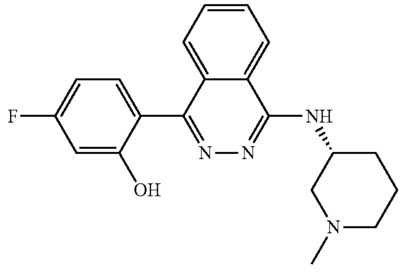

44

Step: The compound (1d) (0.05 g, 0.18 mmol), (4-fluoro-2-hydroxyphenyl)boric acid (41.85 mg, 0.27 mmol), sodium carbonate (42.40 mg, 0.40 mmol), and Pd(dppf)$Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound 44 (R)-5-fluoro-2-(4-((1-methylpiperidin-3-yl)amino)phthalazin-1-yl)phenol (0.02 g, yield: 31.54%. LCMS m/z=353.2[M+1]$^+$).

Example 45: (R)-(4-(2-hydroxy-4-(trifluoromethyl)phenyl)-1-((1-methylpiperidin-3-yl)amino)phthalazin-6-yl)dimethylphosphine oxide

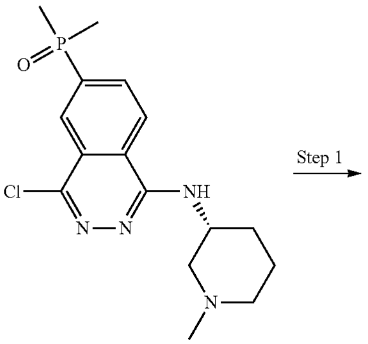

43f

-continued

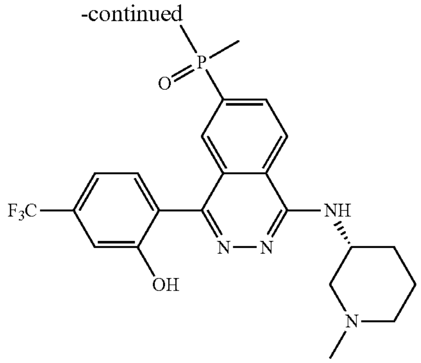

45

Step 1: The compound (43f) (30 mg, 0.08 mmol), (2-hydroxy-4-(trifluoromethyl)phenyl)boronic acid (35 mg, 0.17 mmol), sodium carbonate (26 mg, 0.24 mmol), and Pd(dppf)$Cl_2$ (5 mg, 0.007 mmol) were added to 5 mL of a mixed solvent of dioxane and water (v/v=4:1), followed by nitrogen displacement 3 times and heating to 110 °C for reaction for 16 hours. The reaction solution was spin-dried and then directly separated by silica gel column chromatography (DCM:$CH_3OH$=10:1) to obtain a compound 45 (R)-(4-(2-hydroxy-4-(trifluoromethyl)phenyl)-1-((1-methylpiperidin-3-yl)amino)phthalazin-6-yl)dimethylphosphine oxide (0.01 g, yield: 24.59%, LCMS m/z=479.6 [M+1]$^+$).

Example 46: Synthesis of (R)-4-fluoro-2-(4-((1-methylpiperidin-3-yl)amino)phthalazin-1-yl)phenol

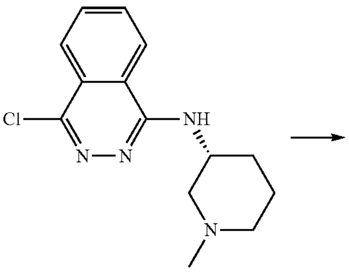

1d

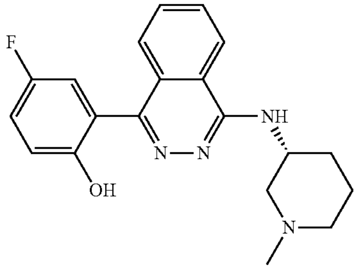

46

Step: The compound (1d) (0.05 g, 0.18 mmol), (5-fluoro-2-hydroxyphenyl)boric acid (41.85 mg, 0.27 mmol), sodium carbonate (42.40 mg, 0.40 mmol), and Pd(dppf)$Cl_2$ (19.75 mg, 0.027 mmol) were added to 5 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound 46 (R)-4-fluoro-2-(4-((1-methylpiperidin-3-yl)amino)phthalazin-1-yl)phenol (0.012 g, yield: 18.93%. LCMS m/z=353.2[M+1]$^+$).

Example 47: Synthesis of ((R)-4-methyl-2-(4-((1-methylpiperidin-3-yl)amino)phthalazin-1-yl)phenol

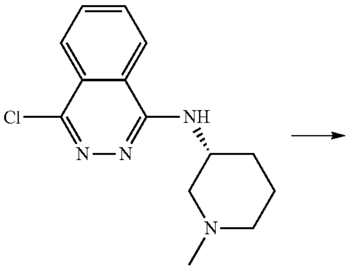

1d

-continued

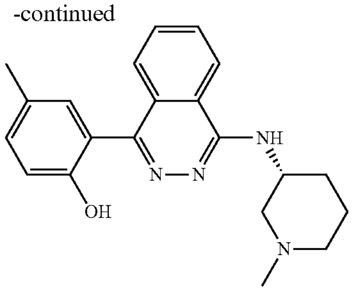

47

Step: The compound (1d) (0.05 g, 0.18 mmol), (2-hydroxy-5-methylphenyl)boric acid (40.77 mg, 0.27 mmol), sodium carbonate (42.40 mg, 0.40 mmol), and Pd(dppf)$Cl_2$ (19.75 mg, 0.027 mmol) were added to 5 mL of a mixed solvent of dioxane and water (v/v=4:1), followed by nitrogen displacement 3 times and heating to 110° for reaction for 3 hours. The reaction solution was quenched with water (50 mL) and extracted with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (DCM:$CH_3OH$=10:1) to obtain a target compound 47 (R)-4-methyl-2-(4-((1-methylpiperidin-3-yl)amino) phthalazin-1-yl)phenol (0.015 g, yield: 23.%, LCMS m/z=349.2[M+1]$^+$).

Example 48: 2-(3-methyl-8-{([(3R)-1-methylpiperidin-3-yl]amino}pyridino[2,3-d]pyridazin-5-yl)-5-(trifluoromethyl)phenol and Example 49: 2-(3-methyl-5-{[(3R)-1-methylpiperidin-3-yl]amino}pyridino[2,3-d]pyridazin-8-yl)-5-(trifluoromethyl)phenol

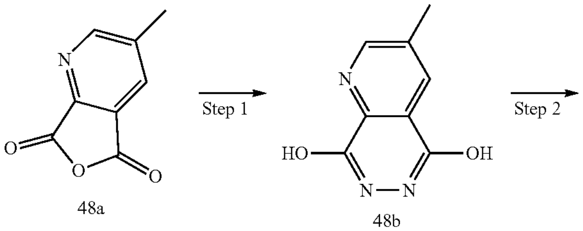

48a

48b

-continued

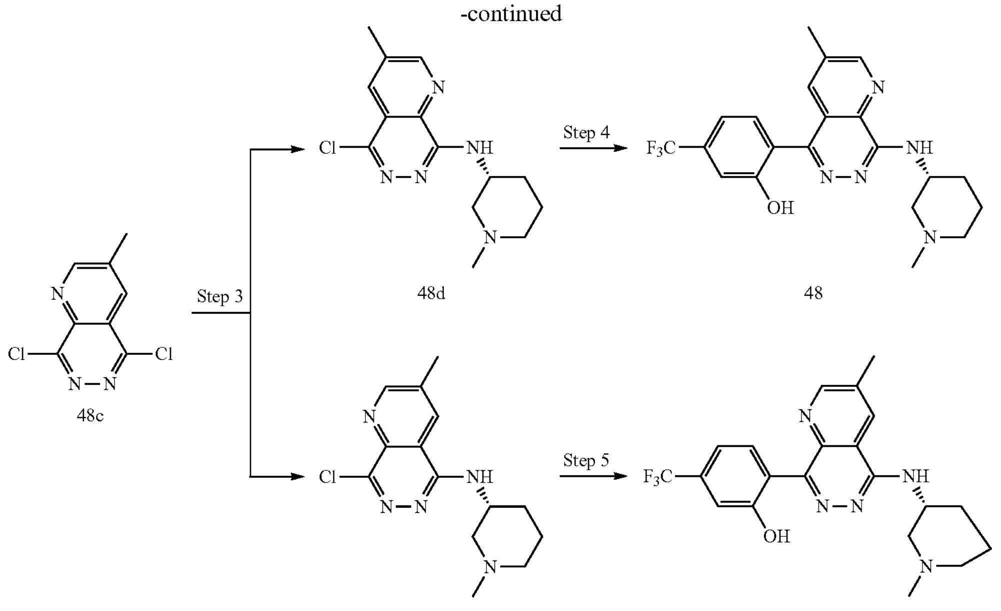

48c 48d 48 48e 49

Step 1: A compound (48a) (3-methyl-5H,7H-furano[3,4-b]pyridine-5,7-dione) (1.0 g, 6.13 mmol) and $N_2H_4 \cdot H_2O$ (2.5 g, 41.1 mmol, 80% wt) were dissolved in acetic acid (20 mL), followed by heating to 110 °C for overnight reflux. Complete reaction was determined by TLC, the reaction solution was directly filtered, washing with water (20 mL×3) was performed, and filter cakes were drained and dried in vacuum to obtain a target compound 48b (3-methylpyridino [2,3-d]pyridazine-5,8-diol) (1.0 g, yield: 92.08%, LCMS m/z=177.1 $[M+1]^+$).

Step 2: The compound (48b) (1.0 g, 5.6 mmol) was dissolved in $POCl_3$ (5 mL), followed by heating to 110 °C for overnight reaction. Complete reaction was determined by TLC, the reaction solution was concentrated to one tenth of the volume, then slowly added dropwise to ice water (20 ml), and stirred thoroughly, the pH value was adjusted to 8 with 2N sodium hydroxide aqueous solution, extraction was performed with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (PE:EA=20:1) to obtain a target compound 48c (5,8-dichloro-3-methylpyridino[2,3-d]pyridazine) (0.70 g, yield: 58.66%, LCMS m/z=214.2 $[M+1]^+$).

Step 3: The compound (48c) (0.46 g, 2.16 mmol), (R)-1-methylpiperidine-3-amine (0.25 g, 2.16 mmol), and $Na_2CO_3$ (0.43 g, 4.00 mmol) were dissolved in dry DMF (4 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10:1) to obtain a target compound 48d ((R)-5-chloro-3-methyl-N-(1-methylpiperidin-3-yl)pyridino[2,3-d] pyridazine-8-amine) (0.20 g, yield: 31.73%, LCMS m/z=292.2 $[M+1]^+$) and a compound 48e (3R)—N-(8-chloro-3-methylpyridino[2,3-d]pyridazin-5-yl)-1-methylpiperidine-3-amine (50 mg, yield: 7.95%, LCMS m/z=292.2 $[M+1]^+$).

Step 4: The compound (48d) (200 mg, 0.69 mmol), (2-hydroxy-4-(trifluoromethyl)phenyl)boronic acid (280 mg, 1.38 mmol), sodium carbonate (220 mg, 2.07 mmol), and $Pd(dppf)Cl_2$ (50 mg, 0.07 mmol) were added to 10 mL of a mixed solvent of dioxane and water (v/v=4:1), followed by nitrogen displacement 3 times and heating to 110 °C for reaction for 16 hours. The reaction solution was spin-dried and then directly separated by silica gel column chromatography (DCM:$CH_3OH$=10:1) to obtain a compound 48 (2-(3-methyl-8-{[(3R)-1-methylpiperidin-3-yl]amino}pyridino [2,3-d]pyridazin-5-yl)-5-(trifluoromethyl)phenol) (0.10 g, yield: 34.72%, LCMS m/z=418.6 $[M+1]^+$).

Step 5: The compound (48e) (25 mg, 0.086 mmol), (2-hydroxy-4-(trifluoromethyl)phenyl)boronic acid (35 mg, 0.17 mmol), sodium carbonate (28 mg, 0.26 mmol), and $Pd(dppf)Cl_2$ (5 mg, 0.007 mmol) were added to 5 mL of a mixed solvent of dioxane and water (v/v=4:1), followed by nitrogen displacement 3 times and heating to 110 °C for reaction for 16 hours. The reaction solution was spin-dried and then directly separated by silica gel column chromatography (DCM:$CH_3OH$=10:1) to obtain a compound 49 (2-(3-methyl-5-{[(3R)-1-methylpiperidin-3-yl]amino}pyridino [2,3-d]pyridazin-8-yl)-5-(trifluoromethyl)phenol) (20 mg, yield: 55.71%, LCMS n/z, =418.6 $[M+1]^+$).

Example 50: (R)-2-(3-ethyl-8-((1-methylpiperidin-3-yl)amino)pyridino[2,3-d]pyridazin-5-yl)-5-(trifluoromethyl)phenol and Example 51: (R)-2-(3-ethyl-5-((1-methylpiperidin-3-yl)amino)pyridino[2,3-d]pyridazin-8-yl)-5-(trifluoromethyl)phenol

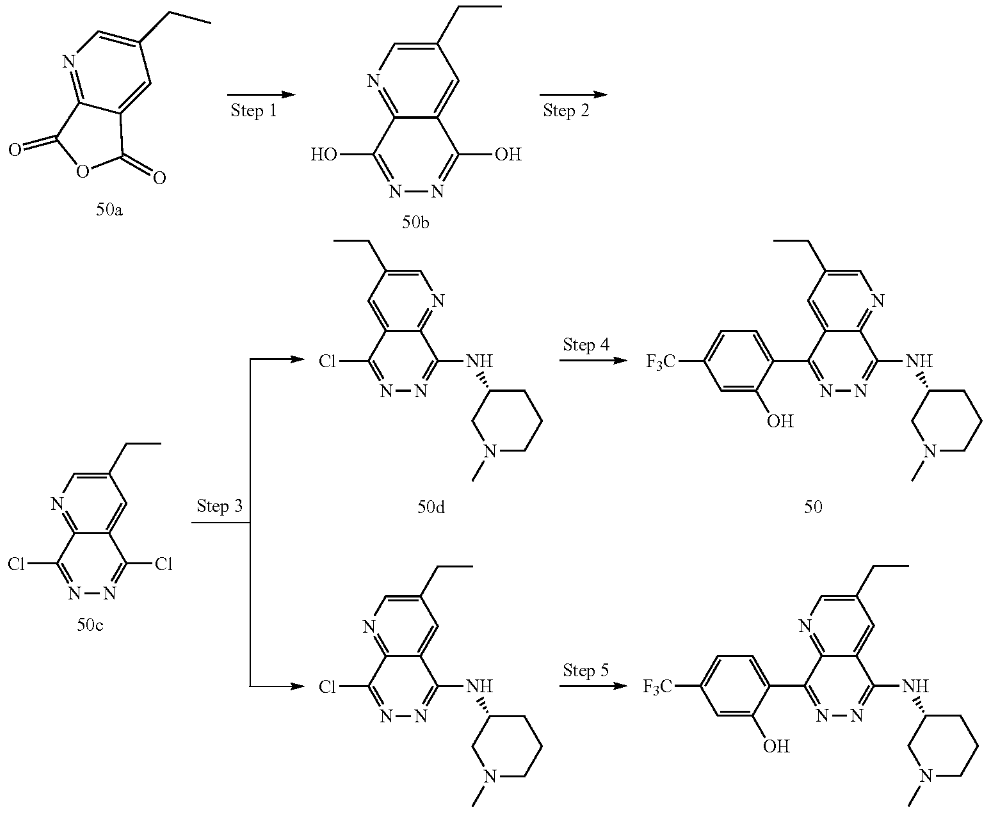

50a 50b 50c 50d 50 50e 51

Step 1: A compound (50a) 3-ethylfurfuro[3,4-b]pyridine-5,7-dione (1.0) g, 5.64 mmol) and $N_2H_4 \cdot H_2O$ (2.5 g, 41.1 mmol, 80% wt) were dissolved in acetic acid (20 mL), followed by heating to 110 °C for overnight reflux. Complete reaction was determined by TLC, the reaction solution was directly filtered, washing with water (20 mLx3) was performed, and filter cakes were drained and dried in vacuum to obtain a target compound 50b (3-ethylpyridino [2,3-d]pyridazine-5,8-diol) (0.8 g, yield: 74.26%, LCMS m/z=192.2 $[M+1]^+$).

Step 2: The compound (50b) (0.8 g, 4.2 mmol) was dissolved in $POCl_3$ (5 mL), followed by heating to 110° (C for overnight reaction. Complete reaction was determined by TLC, the reaction solution was concentrated to one tenth of the volume, then slowly added dropwise to ice water (20 ml), and stirred thoroughly, the pH value was adjusted to 8 with 2N sodium hydroxide aqueous solution, extraction was performed with ethyl acetate (10 mLx3), organic phases were combined, washed with saturated salt water (10 mLx3), dried with anhydrous sodium sulfate, and filtered, the solvent was removed from the filtrate under reduced pressure, and the residue was separated by column chromatography (PE:EA=20:1) to obtain a target compound 50c (5,8-dichloro-3-ethylpyridino[2,3-d]pyridazine) (0.70 g, yield: 73.09%, LCMS m/z=228.1 $[M+1]^+$).

Step 3; The compound (50c) (0.46 g, 2.01 mmol), (R)-1-methylpiperidine-3-amine (0.25 g, 2.16 mmol), and $Na_2CO_3$ (0.43 g, 4.0) mmol) were dissolved in dry DMF (4 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mLx3), organic phases were combined, washed with saturated salt water (10 mLx3), dried with anhydrous sodium sulfate, and filtered, the solvent was removed from the filtrate under reduced pressure, and the residue was separated by column chromatography (DCM: $CH_3OH$=10:1) to obtain a target compound 50d ((R)-5-chloro-3-ethyl-N-(1-methylpiperidin-3-yl)pyridino[2,3-d] pyridazine-8-amine) (0.20 g, yield: 32.51%, LCMS m/z=306.2 $[M+1]^+$) and a compound 50e (R)-8-chloro-3-ethyl-N-(1-methylpiperidin-3-yl)pyridino[2,3-d]pyridazine-5-amine (100 mg, yield: 16.25%, LCMS m/z=305.4 $[M+1]^+$).

Step 4: The compound (50d) (100 mg, 0.326 mmol), (2-hydroxy-4-(trifluoromethyl)phenyl)boronic acid (280 mg, 1.38 mmol), sodium carbonate (220 mg, 2.07 mmol), and Pd(dppf)$Cl_2$ (50 mg, 0.07 mmol) were added to 10 mL of a mixed solvent of dioxane and water (v/v=4:1), followed by nitrogen displacement 3 times and heating to 110 °C for reaction for 16 hours. The reaction solution was spin-dried and then directly separated by silica gel column chromatography (DCM:$CH_3OH$=10:1) to obtain a compound 50 ((R)-2-(3-ethyl-8-((1-methylpiperidin-3-yl)amino)pyridino[2,3-d]pyridazin-5-yl)-5-(trifluoromethyl)phenol) (0.05 g, yield: 35.56%, LCMS m/z=432.6 $[M+1]^+$).

Step 5: The compound (50e) (100 mg, 0.326 mmol), (2-hydroxy-4-(trifluoromethyl)phenyl)boronic acid (35 mg, 0.17 mmol), sodium carbonate (28 mg, 0.26 mmol), and Pd(dppf)$Cl_2$ (5 mg, 0.007 mmol) were added to 5 mL of a mixed solvent of dioxane and water (v/v=4:1), followed by nitrogen displacement 3 times and heating to 110 °C for reaction for 16 hours. The reaction solution was spin-dried and then directly separated by silica gel column chromatography (DCM:$CH_3OH$=10:1) to obtain a compound 51 ((R)-2-(3-ethyl-5-((1-methylpiperidin-3-yl)amino)pyridino[2,3-d]pyridazin-8-yl)-5-(trifluoromethyl)phenol) (0.1 g, yield: 71.17%, LCMS m/z=432.6 $[M+1]^+$).

Example 52: (R)-2-(2-methyl-8-((1-methylpiperidin-3-yl)amino)pyridino[2,3-d]pyridazin-5-yl)-5-(trifluoromethyl)phenol and

Example 53: (R)-2-(2-methyl-5-((1-methylpiperidin-3-yl)amino)pyridino[2,3-d]pyridazin-8-yl)-5-(trifluoromethyl)phenol Step 1: A compound (52a) (2-methylfurfuro[3,4-b]pyridine-5,7-dione) (1.0 g, 6.13 mmol) and $N_2H_4 \cdot H_2O$ (2.5 g, 41.1 mmol, 80% wt) were dissolved in acetic acid (20 mL), followed by heating to 110 °C for overnight reflux. Complete reaction was determined by TLC, the reaction solution was directly filtered, washing with water (20 mL×3) was performed, and filter cakes were drained and dried in vacuum to obtain a target compound 52b (2-methylpyridino[2,3-d]pyridazine-5,8-diol) (1.0 g, yield: 92.08%, LCMS m/z=177.1 $[M+1]^+$).

Step 2: The compound (52b) (1.0 g, 5.6 mmol) was dissolved in $POCl_3$ (5 mL), followed by heating to 110 °C for overnight reaction. Complete reaction was determined by TLC, the reaction solution was concentrated to one tenth of the volume, then slowly added dropwise to ice water (20 ml), and stirred thoroughly, the pH value was adjusted to 8 with 2N sodium hydroxide aqueous solution, extraction was performed with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (PE:EA=20:1) to obtain a target compound 52c (5,8-dichloro-2-methylpyridino[2,3-d]pyridazine) (0.70 g, yield: 58.66%, LCMS m/z=214.21$[M+1]^+$).

Step 3: The compound (52c) (0.46 g, 2.16 mmol), (R)-1-methylpiperidine-3-amine (0.25 g, 2.16 mmol), and $Na_2CO_3$ (0.43 g, 4.00 mmol) were dissolved in dry DMF (4 mL), and the mixed system was heated in a sealed tube to 120 °C for overnight reaction. Complete conversion of raw

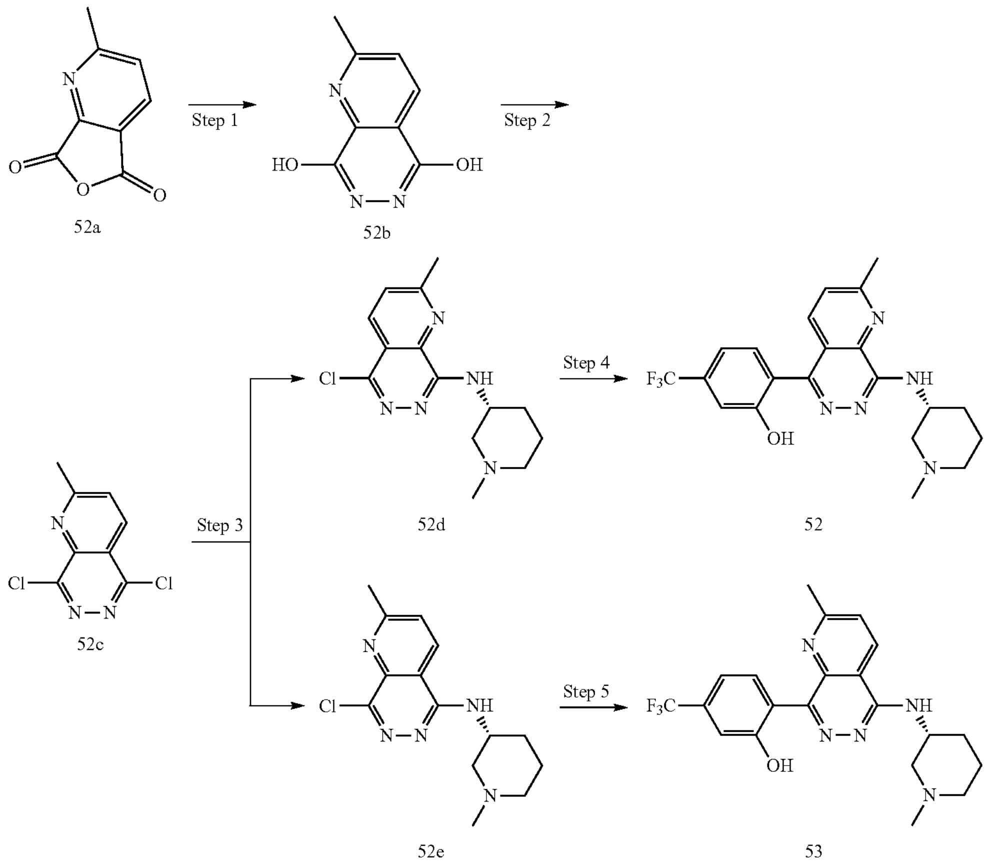

52a
52b
52c
52d
52
52e
53 materials was determined by TLC, the reaction solution was added to water (20 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10:1) to obtain a target compound 52d ((R)-5-chloro-2-methyl-N-(1-methylpiperidin-3-yl)pyridino[2,3-d] pyridazine-8-amine) (0.10 g, yield: 15.90%, LCMS m/z=292.4 $[M+1]^+$) and a compound 52e ((R)-8-chloro-2-methyl-N-(1-methylpiperidin-3-yl)pyridino[2,3-d] pyridazine-5-amine) (0.10 g, yield: 15.90%, LCMS m/z=292.4 $[M+1]^+$).

Step 4: The compound (52d) (100 mg, 0.34 mmol), (2-hydroxy-4-(trifluoromethyl)phenyl)boronic acid (280 mg, 1.38 mmol), sodium carbonate (220 mg, 2.07 mmol), and Pd(dppf)$Cl_2$ (50 mg, 0.07 mmol) were added to 10 mL of a mixed solvent of dioxane and water (v/v=4:1), followed by nitrogen displacement 3 times and heating to 110 °C for reaction for 16 hours. The reaction solution was spin-dried and then directly separated by silica gel column chromatography (DCM:$CH_3OH$=10:1) to obtain a compound 52 ((R)-2-(2-methyl-8-((1-methylpiperidin-3-yl)amino)pyridino[2, 3-d]pyridoin-5-yl)-5-(trifluoromethyl)phenol) (25 mg, yield: 17.63%, LCMS m/z=418.6 $[M+1]^+$).

Step 5: The compound (52e) (100 mg, 0.34 mmol), (2-hydroxy-4-(trifluoromethyl)phenyl)boronic acid (35 mg, 0.17 mmol), sodium carbonate (28 mg, 0.26 mmol), and Pd(dppf)$Cl_2$ (5 mg, 0.007 mmol) were added to 5 mL of a mixed solvent of dioxane and water (v/v=4:1), followed by nitrogen displacement 3 times and heating to 110 °C for reaction for 16 hours. The reaction solution was spin-dried and then directly separated by silica gel column chromatography (DCM:$CH_3OH$=10:1) to obtain a compound 53 ((R)-2-(2-methyl-5-((1-methylpiperidin-3-yl)amino)pyridino[2, 3-d]pyridazin-8-yl)-5-(trifluoromethyl)phenol) (20 mg, yield: 14.10%, LCMS m/z=418.6 $[M+1]^+$).

Example 54: (R)-2-(4-((1-methylpiperidin-3-yl) amino)thieno[3,4-d]pyridazin-1-yl)-5-(trifluoromethyl)phenol

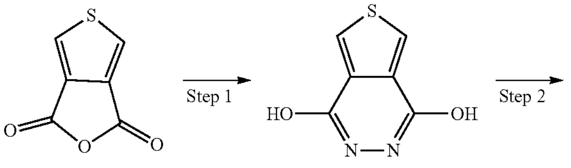

54a 54b

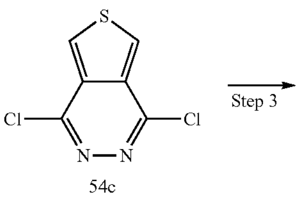

54c

-continued

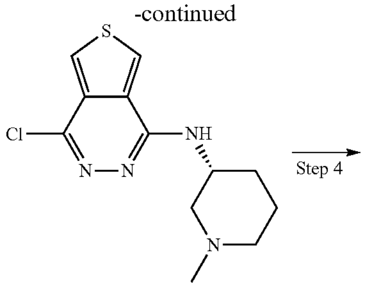

54d

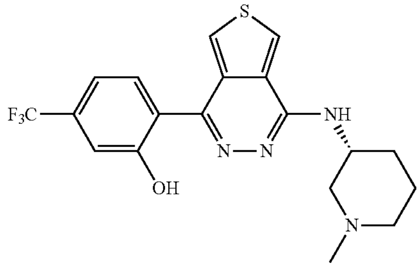

54

Step 1: A compound (54a) (3,4-thiophene dicarboxylic anhydride) (180 mg, 1.16 mmol) and $N_2H_4 \cdot H_2O$ (0.6 mL, 9.88 mmol, 80% wt) were dissolved in acetic acid (10 mL), followed by heating to 110 °C for overnight reflux. Complete reaction was determined by TLC, the reaction solution was directly filtered, washing with water (10 mL×3) was performed, and filter cakes were drained and dried in vacuum to obtain a target compound 54b (thieno[3,4-d] pyridazine-1,4-diol) (150 mg, yield: 76.89%, LCMS m/z=169.1 $[M+1]^+$).

Step 2: The compound (54b) (150 mg, 0.89 mmol) was dissolved in $POCl_3$ (3 mL), followed by heating to 110 °C for overnight reaction. Complete reaction was determined by TLC, the reaction solution was concentrated to one tenth of the volume, then slowly added dropwise to ice water (10 ml), and stirred thoroughly, the pH value was adjusted to 8 with 2N sodium hydroxide aqueous solution, extraction was performed with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (PE:EA=20:1) to obtain a target compound 54c (1,4-dichlorothieno[3,4-d]pyridazine) (76 mg, yield: 41.64%, LCMS m/z=205.0 $[M+1]^+$).

Step 3: The compound (54c) (70 mg, 0.34 mmol), (R)-1-methylpiperidine-3-amine (40 mg, 0.35 mmol), and $Na_2CO_3$ (74 mg, 0.70 mmol) were dissolved in dry DMF (3 mL), and the mixed system was heated in a sealed tube to 120 °C for overnight reaction. Complete conversion of raw materials was determined by TLC, the reaction solution was added to water (10 ml), stirred thoroughly, and extracted with ethyl acetate (10 mL×3), organic phases were combined, washed with saturated salt water (10 mL×3), dried with anhydrous sodium sulfate, and filtered, the solvent was removed from the filtrate under reduced pressure, and the residue was separated by column chromatography (DCM: $CH_3OH$=10:1) to obtain a target compound 54d ((R)-4-chloro-N-(1-methylpyrid-3-yl)thieno[3,4-d]pyridazine-1-amine) (50 mg, yield: 52.00%, LCMS m/z=283.1 $[M+1]^+$).

Step 4: The compound (54d) (50 mg, 0.18 mmol), (2-hydroxy-4-(trifluoromethyl)phenyl)boronic acid (74 mg, 0.36 mmol), sodium carbonate (60 mg, 0.57 mmol), and Pd(dppf)$Cl_2$ (5 mg, 0.007 mmol) were added to 5 mL of a mixed solvent of dioxane and water (v/v=4:1), followed by nitrogen displacement 3 times and heating to 110 °C for reaction for 16 hours. The reaction solution was spin-dried and then directly separated by silica gel column chromatography (DCM:$CH_3OH$=10:1) to obtain a compound 54 ((R)-2-(4-((1-methylpiperidin-3-yl)amino)thieno[3,4-d]pyridazin-1-yl)-5-(trifluoromethyl)phenol) (20 mg, yield: 27.2%, LCMS m/z=409.4 $[M+1]^+$).

Example 55: (R)-5-fluoro-2-(3-methyl-S-((1-methylpiperidin-3-yl)amino)pyridino[2,3-d]pyridazin-5-yl)phenol

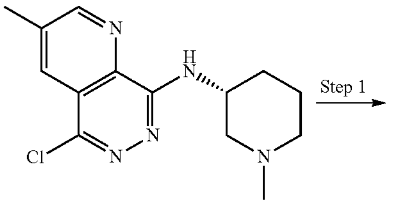

48d

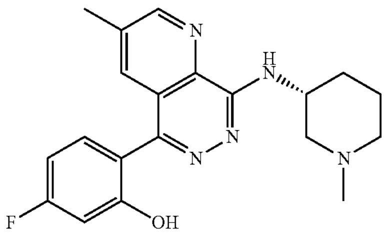

55

Step 1: The compound (48d) (30 mg, 0.10 mmol), 5-fluoro-2-(tetramethyl-1,3,2-dioxaborolan-2-yl)phenol (86 mg, 0.36 mmol), sodium carbonate (42 mg, 0.40 mmol), and Pd(dppf)$Cl_2$ (5 mg, 0.007 mmol) were added to 5 mL of a mixed solvent of dioxane and water (v/v=4:1), followed by nitrogen displacement 3 times and heating to 110 °C for reaction for 16 hours. The reaction solution was spin-dried and then directly separated by silica gel column chromatography (DCM:$CH_3OH$=10:1) to obtain a compound 55 ((R)-5-fluoro-2-(3-methyl-8-((1-methylpiperidin-3-yl)amino)pyridino[2,3-d]pyridazin-5-yl)phenol) (20 mg, yield: 45.36%, LCMS m/z=368.6 $[M+1]^+$)

Example 56: (R)-2-(3-methyl-S-((1-methylpiperidin-3-yl)amino)pyridino[2,3-d]pyridazin-5-yl)phenol

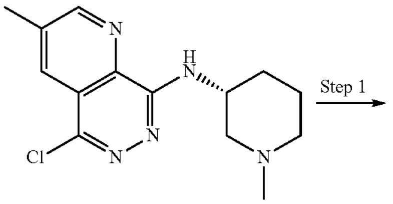

48d

-continued

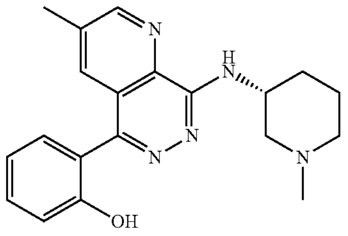

56

Step 1: The compound (48d) (30 mg, 0.10 mmol), 5-fluoro-2-(tetramethyl-1,3,2-dioxaborolan-2-yl)phenol (79 mg, 0.36 mmol), sodium carbonate (42 mg, 0.40 mmol), and Pd(dppf)$Cl_2$ (5 mg, 0.007 mmol) were added to 5 mL of a mixed solvent of dioxane and water (v/v=4:1), followed by nitrogen displacement 3 times and heating to 110 °C for reaction for 16 hours. The reaction solution was spin-dried and then directly separated by silica gel column chromatography (DCM:$CH_3OH$=10:1) to obtain a compound 56 ((R)-2-(3-methyl-8-((1-methylpiperidin-3-yl)amino)pyridino[2,3-d]pyridazin-5-yl)phenol) (30 mg, yield: 71.55%, LCMS m/z=350.6 $[M+1]^+$)

Example 60: 5-methyl-2-(3-methyl-8-{[(3R)-1-methylpiperidin-3-yl]amino}pyridino[2,3-d]pyridazin-5-yl)phenol

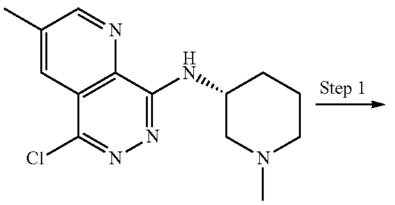

48d

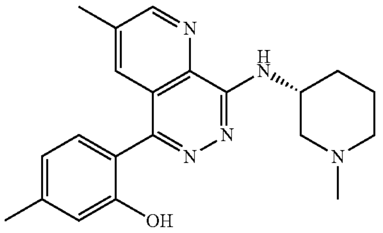

60

Step 1: The compound (48d) (30 mg, 0.10 mmol), 5-methyl-2-(tetramethyl-1,3,2-dioxaborolan-2-yl)phenol (47 mg, 0.20 mmol), sodium carbonate (42 mg, 0.40 mmol), and Pd(dppf)$Cl_2$ (5 mg, 0.007 mmol) were added to 5 mL of a mixed solvent of dioxane and water (v/v=4:1), followed by nitrogen displacement 3 times and heating to 110 °C for reaction for 16 hours. The reaction solution was spin-dried and then directly separated by silica gel column chromatography (DCM:$CH_3OH$=10:1) to obtain a compound 60 (5-methyl-2-(3-methyl-8-{[(3R)-1-methylpiperidin-3-yl]amino}pyridino[2,3-d]pyridazin-5-yl)phenol) (10 mg, yield: 27.51%, LCMS m/z=364.6 $[M+1]^+$)

Example 61: 2-(3-methyl-8-{[(3R)-1-methylpiperidin-3-yl]amino}pyridino[2,3-d]pyridazin-5-yl)-5-(trifluoromethoxy)phenol

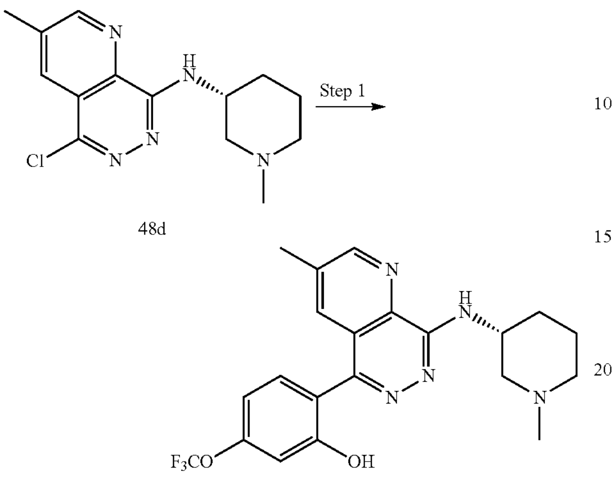

48d

61

Step 1: The compound (48d) (30 mg, 0.10 mmol), 5-trifluoromethoxy-2-(tetramethyl-1,3,2-dioxaborolan-2-yl)phenol (61 mg, 0.20 mmol), sodium carbonate (42 mg, 0.40 mmol), and Pd(dppf)$Cl_2$ (5 mg, 0.007 mmol) were added to 5 mL of a mixed solvent of dioxane and water (v/v=4:1), followed by nitrogen displacement 3 times and heating to 110 °C for reaction for 16 hours. The reaction solution was spin-dried and then directly separated by silica gel column chromatography (DCM:$CH_3OH$=10:1) to obtain a compound 61 (2-(3-methyl-8-{[(3R)-1-methylpiperidin-3-yl]amino}pyridino[2,3-d]pyridazin-5-yl)-5-(trifluoromethoxy)phenol) (20 mg, yield: 46.14%, LCMS m/z=434.6 $[M+1]^+$)

Example 62: ((R)-2-(1-methyl-7-((1-methylpiperidin-3-yl)amino)-1H-pyrazolo[3,4-d]pyridazin-4-yl)-5-(trifluoromethyl)phenol) and Example 63: ((R)-2-(1-methyl-4-((1-methylpiperidin-3-yl)amino)-1H-pyrazolo[3,4-d]pyridazin-7-yl)-5-(trifluoromethyl)phenol)

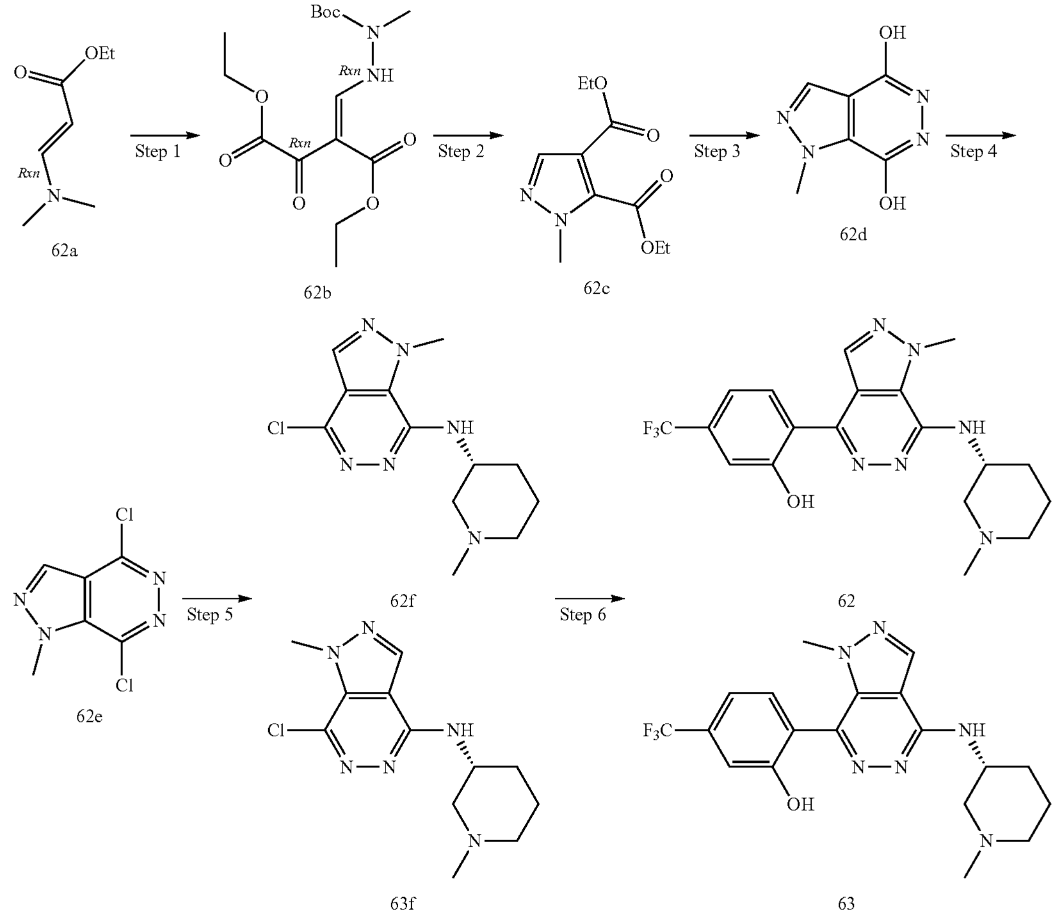

62a 62b 62c 62d 62e 62f 62 63f 63

Step 1: A compound (62a) (10.0 g, 69.84 mmol), DMAP (0.14 g, 1.25 mmol), and triethylamine (9.19 g, 90.79 mmol) were dissolved in dry tetrahydrofuran (100 mL) in an ice water bath, a tetrahydrofuran solution (50 mL) of ethyl 2-chloro-2-oxoacetate (11.44 g, 83.81 mmol) was slowly added dropwise to the mixed solution, and then the mixed solution was naturally heated to room temperature for reaction for 1 hour. TLC showed that the raw material (62a) was used up, then the salt generated in the reaction solution was filtered, the filtrate was added to a reaction flask, t-butyl 1-methylhydrazine-1-carboxylate (12.25 g, 83.81 mmol) was added, and the reaction continued at room temperature for 2 hours. The reaction solution was directly concentrated and dried to obtain a yellow solid. The solid was recrystallized with methanol/water (100 mL, v/v=1:1), and then dried in vacuum to obtain a target compound 62b (diethyl (Z/E mixed)-2-(2-(tert-butoxycarbonyl)-2-methylhydrazino) methylene)-3-oxosuccinate) (19.2 g, yield: 79.83%)

Step 2: The raw material (62b) (19.2 g, 55.75 mmol) was dispersed with ethyl acetate (60 ml), a HCl/dioxane solution (200 ml) was added, and the mixed solution was heated to 50 °C for reaction for 3 hours. Concentration and dissolution again in ethyl acetate (200 ml) were performed, the pH value was adjusted to be greater than 7 with 2N sodium carbonate aqueous solution, the solution was separated, organic phases were washed with saturated salt water (50 mL×3), dried with anhydrous sodium sulfate, and filtered, the solvent was removed from the filtrate under reduced pressure, and the residue was separated by column chromatography (PE: EA=5:1) to obtain a target compound 62c (diethyl 1-methyl-1H-pyrazole-4,5-dicarboxylate) (10.2 g, yield: 80.87%, LCMS m/z=227.2 $[M+1]^+$)

Step 3: The compound diethyl 1-methyl-1H-pyrazole-4,5-dicarboxylate (62c) (0.8 g, 4.04 mmol) and $N_2H_4 \cdot H_2O$ (0.61 g, 12.12 mmol) were dissolved in acetic acid (5 mL), followed by heating to 120 °C for overnight reflux. Complete reaction was determined by TLC, the reaction solution was directly concentrated, then water (30 ml) was added to disperse the solid, filtration was performed, and filter cakes were drained and dried in vacuum overnight to obtain a target compound 62d (1-methyl-1H-pyrazolo[3,4-d] pyridazine-4,7-diol) (0.40 g, yield: 59.59%, LCMS m/z=167.2 $[M+1]^+$).

Step 4: The compound 62d (0.40 g, 2.41 mmol) was dissolved in $POCl_3$ (10 mL), followed by heating to 100 °C for overnight reaction. Complete reaction was determined by TLC, the reaction solution was directly concentrated to remove the $POCl_3$, then the oily crude product was slowly added dropwise to ice water (50 ml), the solution was stirred thoroughly, the pH value was adjusted to 8 with 2N sodium hydroxide aqueous solution, extraction was performed with ethyl acetate (30 mL×3), organic phases were combined, washed with saturated salt water (30 mL×3), dried with anhydrous sodium sulfate, and filtered, the solvent was removed from the filtrate under reduced pressure, and the residue was separated by column chromatography (PE: EA=5:1) to obtain a target compound (62e) (4,7-dichloro-1-methyl-1H-pyrazolo[3,4-d]pyridazine) (0.40 g, yield: 81.75%, LCMS m/z=203.2 $[M+1]^+$).

Step 5: The compound (62e) (0.40 g, 1.97 mmol), (R)-1-methylpiperidine-3-amine (0.27 g, 2.36 mmol), and $Na_2CO_3$ (0.21 g, 1.97 mmol) were dissolved in dry DMF (5 mL), and the mixed system was heated in a sealed tube to 120 °C for overnight reaction. Complete conversion of raw materials was determined by TLC, the reaction solution was added to water (20 ml), stirred thoroughly, and extracted with ethyl acetate (10 mL×3), organic phases were combined, washed with saturated salt water (10 ml×3), dried with anhydrous sodium sulfate, and filtered, the solvent was removed from the filtrate under reduced pressure, and the residue was separated by column chromatography (DCM: $CH_3OH$=10:1) to obtain a target compound (mixture of 62f and 63f) (((R)-4-chloro-1-methyl-N-(1-methylpiperidin-3-yl)-1H-pyrazolo[3,4-d]pyridazine-7-amine, (R)-7-chloro-1-methyl-N-(1-methylpiperidin-3-yl)-1H-pyrazolo[3,4-d] pyridazin-4-amine) (0.31 g, yield: 56.04%, LCMS m/z, =281.2 $[M+1]^+$).

Step 6: The compound (mixture of 62f and 63f) (0.31 g, 1.10 mmol), (2-hydroxy-4-(trifluoromethyl)phenyl)boronic acid (350.00 mg, 1.72 mmol), sodium carbonate (220.10 mg, 2.22 mmol), and $Pd(dppf)Cl_2$ (90.75 mg, 0.13 mmol) were added to 30 mL of a mixed solvent of dioxane and water (v/v=4:1), followed by nitrogen displacement 3 times and heating to 110 °C for reaction for 3 hours. The reaction solution was quenched with water (50 mL) and extracted with ethyl acetate (30 mL×3), organic phases were combined, washed with saturated salt water (30 mL 3), dried with anhydrous sodium sulfate, and filtered, the solvent was removed from the filtrate under reduced pressure, and the residue was separated by column chromatography (DCM: $CH_3OH$=10:1) to obtain a target compound mixture (mixture of 62 and 63), and then the mixture was separated by pre-HPLC to obtain a target compound 62 ((R)-2-(1-methyl-7-((1-methylpiperidin-3-yl)amino)-1H-pyrazolo[3,4-d] pyridazin-4-yl)-5-(trifluoromethyl)phenol) (0.04 g, yield: 8.91%, LCMS m/z=407.4 $[M+1]^+$) and a target compound 63 ((R)-2-(1-methyl-4-(1-methylpiperidin-3-yl)amino)-1H-pyrazolo[3,4-d]pyridazin-7-yl)-5-(trifluoromethyl)phenol (0.16 g, yield: 35.66%, LCMS m/z=407.4 $[M+1]^+$).

Examples 26 and 28 were similar to Example 25, except that the amine in step 1 was replaced with a corresponding commercially available raw amine.

Examples 57-59 were similar to Example 36, except that the imidazole dicarboxylate was replaced with a corresponding commercially available raw material in step 2 and required boric acid or borate in step 5.

Examples 64-75 were similar to Example 62, except that the amine was replaced with a required commercially available amine in step 5 and required boric acid or borate in step 6.

Examples 76-88 were similar to Example 36, except that the amine was replaced with a required commercially available amine in step 4 and required boric acid or borate in step 5.

TABLE 1

| Characterization of compound data in examples | | | |
|---|---|---|---|
| Number | Structural formula | Nuclear magnetic resonance | Ms + 1 |
| 1 | 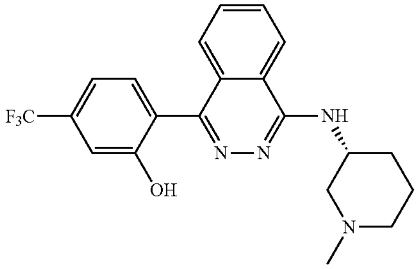 | $^1$H NMR (400 MHz, DMSO) δ 10.33 (s, 1H), 8.41 (d, 1H), 7.88 (t, 1H), 7.83 - 7.76 (m, 1H), 7.51 (d, 1H), 7.46 (d, 1H), 7.34 - 7.14 (m, 3H), 4.59 - 4.46 (m, 1H), 2.98 - 2.84 (m, 1H), 2.47 (s, 3H), 2.37 - 2.30 (m, 1H), 2.05 - 1.94 (m, 2H), 1.91 - 1.80 (m, 1H), 1.76 - 1.63 (m, 1H), 1.62 - 1.39 (m, 2H). | 403.2 |
| 2 | 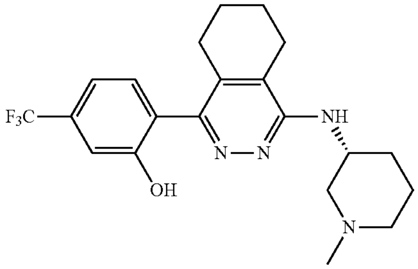 [SMILES: CN1CCC[C@@H](Nc2nnc(-c3ccc(C(F)(F)F)cc3O)c3c2CCCC3)C1] | $^1$H NMR (400 MHz, DMSO) δ 10.33 (s, 1H), 7.34 (d, 1H), 7.23 - 7.17 (m, 2H), 5.61 (d, 1H), 4.35 - 4.23 (m, 1H), 3.04 - 2.89 (m, 1H), 2.49 (s, 3H), 2.39 - 2.36 (m, 2H), 2.34 - 2.24 (m, 4H), 2.04 - 1.95 (m, 2H), 1.88 - 1.81 (m, 1H), 1.80 - 1.72 (m, 2H), 1.64 - 1.57 (m, 2H), 1.51 - 1.44 (m, 1H), 1.37 - 1.32 (m, 1H). | 407.2 |
| 3 | 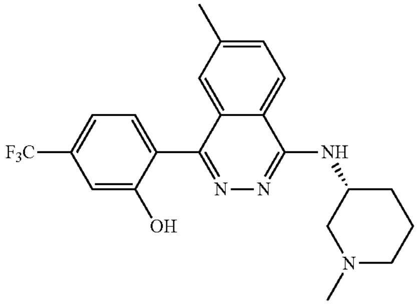 [SMILES: Cc1ccc2c(N[C@@H]3CCCN(C)C3)nnc(-c3ccc(C(F)(F)F)cc3O)c2c1] | $^1$H NMR (400 MHz, DMSO) δ 10.37 (s, 1H), 8.34 (d, 1H), 7.71 (d, 1H), 7.49 (d, 1H), 7.30 - 7.29 (m, 2H), 7.22 - 7.18 (m, 2H), 4.68 - 4.35 (m, 1H), 3.03 - 2.77 (m, 2H), 2.56 - 2.49 (s, 3H), 2.42 (s, 3H), 2.35 - 2.10 (m. 2H), 2.06 - 1.95 (m, 1H), 1.91 - 1.81 (m, 1H), 1.75 - 1.62 (m, 1H), 1.61 - 1.47 (m, 1H). | 417.2 |
| 4 | 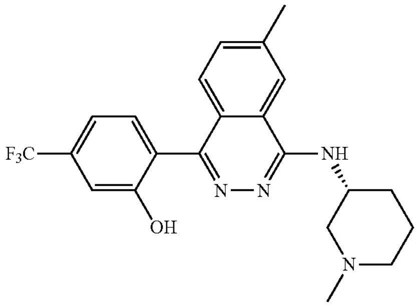 [SMILES: Cc1ccc2c(-c3ccc(C(F)(F)F)cc3O)nnc(N[C@@H]3CCCN(C)C3)c2c1] | $^1$H NMR (400 MHz, DMSO) δ 10.36 (s, 1H), 8.21 (s, 1H), 7.62 (d, 1H), 7.50 (d, 1H), 7.36 (d, 1H), 7.32 - 7.24 (m, 2H), 7.07 (d, 1H), 4.51 - 4.39 (m, 1H), 3.33 - 3.18 (m, 1H), 2.85 - 2.78 (m, 1H), 2.53 (s, 3H), 2.32 (s, 3H), 2.17 - 1.92 (m, 3H), 1.86 - 1.74 (m, 1H), 1.68 - 1.59 (m, 1H), 1.57 - 1.42 (m, 1H). | 417.2 |
| 5 | 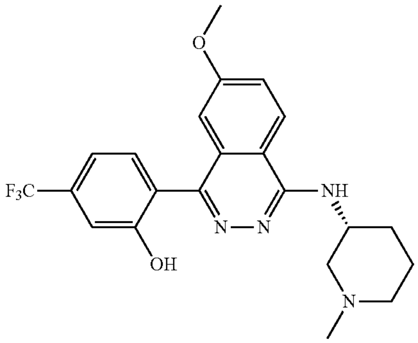 [SMILES: COc1ccc2c(N[C@@H]3CCCN(C)C3)nnc(-c3ccc(C(F)(F)F)cc3O)c2c1] | $^1$H NMR (400 MHz, DMSO) δ 10.43 (s, 1H), 8.40 (d, 1H), 7.54 - 7.50 (m, 2H), 7.34 - 7.30 (m, 2H), 7.20 - 7.16(brs, 1H), 6.76 (d, 1H), 4.58 - 4.44 (m, 1H), 3.77 (s, 3H), 3.49 - 3,44 (m, 1H), 2.99 - 2.93 (m, 1H),, 2.44 (s, 3H), 2.23 - 2.16 (m, 2H),2.01 - 1.97 (m, 1H), 1.88 - 1.83 (m, 1H), 1.69 - 1.63 (m,, 1H), 1.57 - 1.51 (m, 1H). | 433.2 |

TABLE 1-continued

| Characterization of compound data in examples | | | |
|---|---|---|---|
| Number | Structural formula | Nuclear magnetic resonance | Ms + 1 |
| 6 | 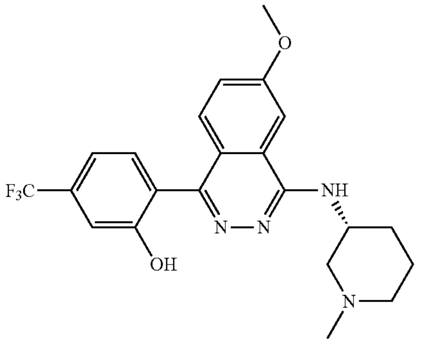 [SMILES: COc1ccc2c(-c3ccc(C(F)(F)F)cc3O)nnc(N[C@@H]3CCCN(C)C3)c2c1] | $^1H$ NMR (400 MHz, DMSO) δ 10.39 (s, 1H), 7.75 (s, 1H), 7.50 (d, 1H), 7.41-7.36 (m, 2H), 7.29 (d, 2H), 7.05(d, 1H), 4.54 – 4.36 (m, 1H), 3.96 (s, 3H), 3.23 – 3.13 (m, 1H), 2.88 – 2.74 (m, 1H), 2.28 (s, 3H), 2.10 – 1.94 (m, 3H), 1.87 – 1.74 (m, 1H), 1.78 – 1.64 (m, 1H), 1.54 – 1.38 (m, 1H). | 433.2 |
| 7 | 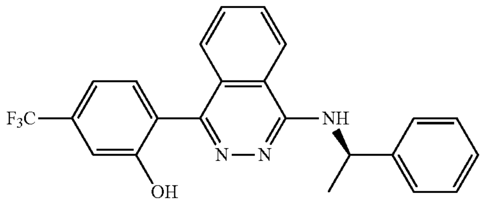 [SMILES: C[C@@H](Nc1nnc(-c2ccc(C(F)(F)F)cc2O)c2ccccc12)c1ccccc1] | $^1H$ NMR (400 MHz, DMSO) δ 10.32 (s, 1H), 8.58 (d, J = 8.3 Hz, 1H), 7.90 (t, J = 7.2 Hz, 1H), 7.84 – 7.76 (m, 2H), 7.53 – 7.40 (m, 4H), 7.35 – 7.24 (m, 4H), 7.20 (t, J = 7.3 Hz, 1H), 5.67 – 5.58 (m, 1H), 1.62 (d, J = 7.0 Hz, 3H). | 410.2 |
| 8 | 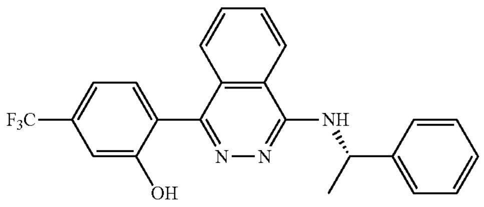 [SMILES: C[C@H](Nc1nnc(-c2ccc(C(F)(F)F)cc2O)c2ccccc12)c1ccccc1] | $^1H$ NMR (400 MHz, DMSO) δ 10.32 (s, 1H), 8.58 (d, 1H), 7.95 – 7.86 (m, 1H), 7.86 – 7.76 (m, 2H), 7.53 – 7.46 (m, 2H), 7.40 (dd, 2H), 7.35 – 7.24 (m, 3H), 7.23 – 7.13 (m, 2H), 5.68 – 5.57 (m, 1H), 1.62 (d, 3H). | 410.2 |
| 9 | 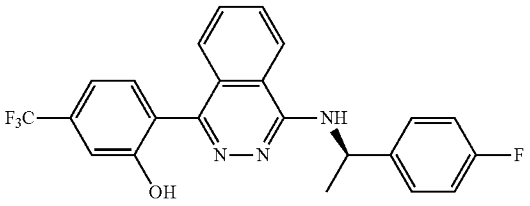 [SMILES: C[C@@H](Nc1nnc(-c2ccc(C(F)(F)F)cc2O)c2ccccc12)c1ccc(F)cc1] | $^1H$ NMR (400 MHz, DMSO) δ 10.32 (s, 1H), 8.55 (d, 1H), 7.93 – 7.87 (m, 1H), 7.84 – 7.77 (m, 2H), 7.56 – 7.50 (m, 2H), 7.45 (dd, 2H), 7.31 – 7.22 (m, 2H), 7.17 – 7.09 (m, 2H), 5.66 – 5,56 (m, 1H), 1.61 (d, 3H). | 428.2 |
| 10 | 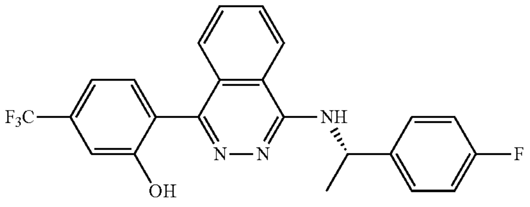 [SMILES: C[C@H](Nc1nnc(-c2ccc(C(F)(F)F)cc2O)c2ccccc12)c1ccc(F)cc1] | $^1H$ NMR (400 MHz, DMSO) δ 10.32 (s, 1H), 8.55 (d, 1H), 7.94 – 7.86 (m, 1H), 7.86 – 7.75 (m, 2H), 7.57 – 7.50 (m, 2H), 7.45 (dd, 2H), 7.30 – 7.24 (m. 2H), 7.19 – 7.08 (m, 2H), 5.67 – 5.56 (m, 1H), 1.61 (d, 3H). | 428.2 |
| 11 | 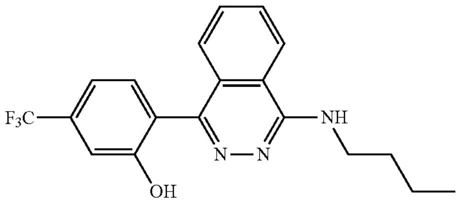 [SMILES: CCCCNc1nnc(-c2ccc(C(F)(F)F)cc2O)c2ccccc12] | $^1H$ NMR (400 MHz, DMSO) δ 10.35 (s, 1H), 8.34 (d, 1H), 7.96 (d,1H), 7.85 (t, 1H), 7.77 (t, 1H), 7.52 (dd, 1H), 7.44 (d, 1H), 7.34 – 7.25 (m. 2H), 3.64 – 3.56 (m, 2H), 1.77 – 1.66 (m, 2H), 1.49 – 1.36 (m, 2H), 0.96 (t, 3H). | 362.2 |

TABLE 1-continued

| Characterization of compound data in examples | | | |
|---|---|---|---|
| Number | Structural formula | Nuclear magnetic resonance | Ms + 1 |
| 12 | 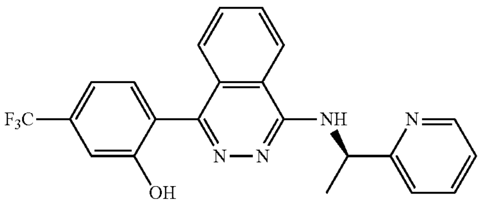 [SMILES: C[C@@H](Nc1nnc(-c2ccc(C(F)(F)F)cc2O)c2ccccc12)c1ccccn1] | $^1$H NMR (400 MHz, DMSO) δ 10.32 (s, 1H), 8.58 (d, 2H), 7.90 (t, 1H), 7.84 - 7.76 (m, 3H), 7.62(m, 1H) 7.53 - 7.40 (m, 4H), 7.35 - 7.24 (m, 4H), 7.20 (t, 1H), 5.67 - 5.58 (m, 1H), 1.62 (d, 3H). | 411.2 |
| 13 | 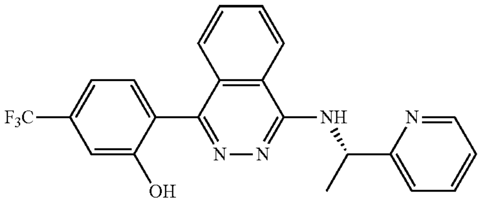 [SMILES: C[C@H](Nc1nnc(-c2ccc(C(F)(F)F)cc2O)c2ccccc12)c1ccccn1] | $^1$H NMR (400 MHz, DMSO) δ 10.32 (s, 1H), 8.58 (d, 2H), 7.90 (t, 1H), 7.84 - 7.76 (m, 3H), 7.62(m, 1H) 7.53 - 7.40 (m, 2H), 7.35 - 7.24 (m, 2H), 7.23 (t, 1H), 5.70 - 5.63 (m, 1H), 1.62 (d, 3H). | 411.2 |
| 14 | 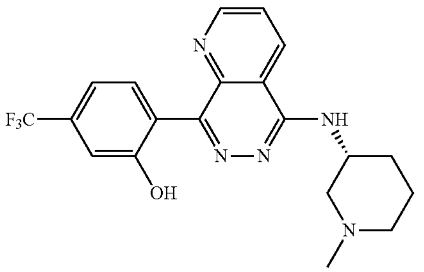 [SMILES: CN1CCC[C@@H](Nc2nnc(-c3ccc(C(F)(F)F)cc3O)c3ncccc23)C1] | $^1$H NMR (400 MHz, $CDCl_3$) δ 9.11 (d, 1H), 8.49 (d, 1H), 7.77 (dd, 1H), 7.61 (d, 1H), 7.43 (s, 1H), 7.25 (d, 1H), 4.68 (s, 1H), 2.96 - 2.88 (m, 1H), 2.50 (s, 3H), 2.08 - 1.99 (m, 2H), 1.91 - 1.79 (m, 4H), 1.23 - 1.16 (m, 2H). | 404.4 |
| 15 | 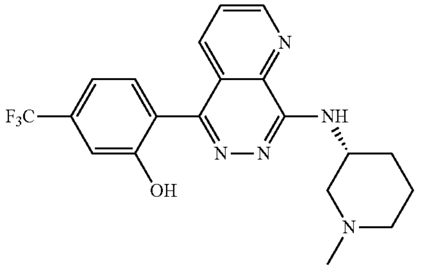 [SMILES: CN1CCC[C@@H](Nc2nnc(-c3ccc(C(F)(F)F)cc3O)c3cccnc23)C1] | $^1$H NMR (400 MHz, $CDCl_3$) δ 9.23 (d, 1H), 9.07 (d, 1H), 7.84 (dd, 1H), 7.36 (s, 1H), 7.27 (d, 1H), 7.22 (d, 1H), 5.01 (s, 1H), 3.50 - 3.16 (m, 1H), 2.75 - 2.49 (m, 4H), 2.34 - 2.24 (m, 1H), 1.84 - 1.71 (m, 4H), 1.23 - 1.17 (m, 2H). | 404.4 |
| 16 | 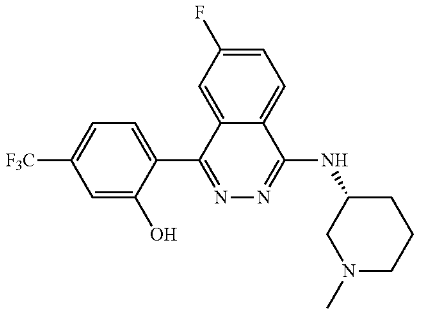 [SMILES: CN1CCC[C@@H](Nc2nnc(-c3ccc(C(F)(F)F)cc3O)c3cc(F)ccc23)C1] | $^1$H NMR (400 MHz, DMSO) δ 10.44 (s, 1H), 8.54 (dd, 1H), 7.98 (d, 1H), 7.79 (td, 1H), 7.55 - 7.49 (m, 1H), 7.33 - 7.23 (m, 2H), 7.08 (dd, 1H), 4.52 - 4.37 (m, 1H), 3.19 - 3.08 (m. 1H), 2.85 - 2.74 (m, 1H), 2.28 (s, 3H), 2.12 - 1.92 (m, 3H), 1.81 - 1.75 (m, 1H), 1.69 - 1.58 (m, 1H), 1.54 - 1.44 (m, 1H). | 421.4 |

TABLE 1-continued
| Characterization of compound data in examples | | | |
|---|---|---|---|
| Number | Structural formula | Nuclear magnetic resonance | Ms + 1 |
| 17 | 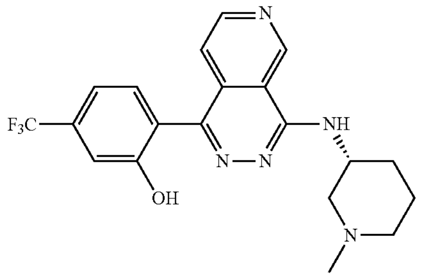 [SMILES: CN1CCC[C@@H](Nc2nnc(-c3ccc(C(F)(F)F)cc3O)c3ccncc23)C1] | $^1$H NMR (400 MHz, DMSO) δ 10.53 (s, 1H), 9.84 (s, 1H), 8.86 (d, 1H), 7.83 (d, 1H), 7.60 (d, 1H), 7.55 (d, 1H), 7.35 - 7.29 (m, 2H), 4.68 - 4.48 (m, 1H), 3.73 - 3.48 (m, 2H), 3.04 - 2.88 (m, 1H), 2.46 (s, 3H), 2.35 - 2.21 (m, 1H), 2.06 - 2.00 (m, 1H), 1.92 - 1.80 (m. 1H), 1.78 - 1.50 (m, 2H). | 404.4 |
| 18 | 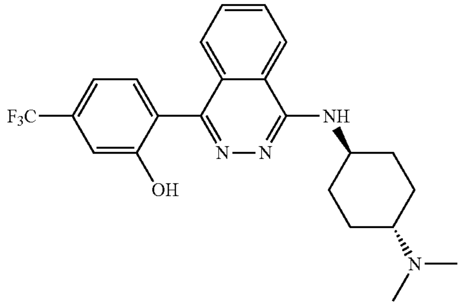 [SMILES: CN(C)[C@H]1CC[C@H](Nc2nnc(-c3ccc(C(F)(F)F)cc3O)c3ccccc23)CC1] | $^1$H NMR (400 MHz, DMSO) δ 10.37 (s, 1H), 8.39 (d, 1H), 7.86 (t, 1H), 7.78 (t, 1H), 7.51 (d, 1H), 7.44 (d, 1H), 7.33 - 7.20 (m, 3H), 4.70 - 4.63 (m, 1H), 4.28 - 4.23 (m, 1H), 2.61 (s, 6H), 2.27 - 2.19 (m, 2H), 2.09 - 1.99 (m, 2H), 1.59 - 1.44 (m, 4H). | 431.4 |
| 19 | 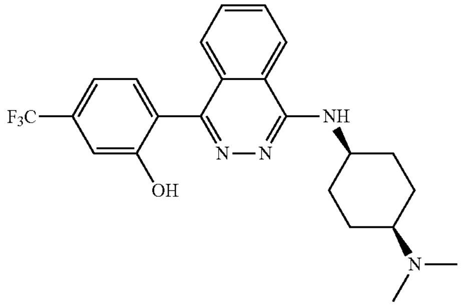 [SMILES: CN(C)[C@H]1CC[C@@H](Nc2nnc(-c3ccc(C(F)(F)F)cc3O)c3ccccc23)CC1] | $^1$H NMR (400 MHz, DMSO) $ 10.36 (s, 1H), 8.58 - 8.51 (m, 1H), 8.14 - 8.05 (m, 1H), 7.80 (d, 1H), 7.77 - 7.70 (m, 2H), 7.65 (dd, 1H), 7.36 (d, 1H), 6.60 (d, 1H), 3.70 (m, 1H), 2.54 (m, 1H), 2.19 (m, 6H), 1.80 - 1.53 (m, 9H). | 431.4 |
| 20 | 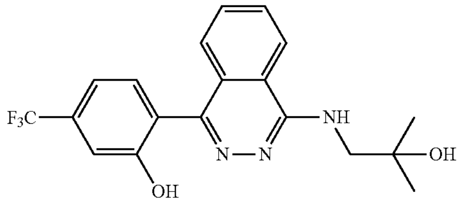 [SMILES: CC(C)(O)CNc1nnc(-c2ccc(C(F)(F)F)cc2O)c2ccccc12] | $^1$H NMR (400 MHz, DMSO) δ 10.41 (s, 1H), 8.41 (d, 1H), 7.90 (t, 1H), 7.82 (m, 2H), 7.59 - 7.43 (m, 2H), 7.30 (d, 2H), 5.10 (br, 1H), 3.64 (d,2H), 1.21 (s, 6H). | 378.4 |
| 21 | 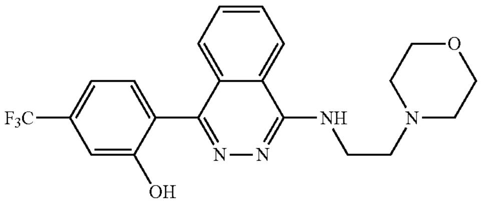 [SMILES: Oc1cc(C(F)(F)F)ccc1-c1nnc(NCCN2CCOCC2)c2ccccc12] | $^1$H NMR (400 MHz, DMSO-d6) δ 10.71 (s, 1H), 8.75 (s, 1H), 8.48 (d, 1H), 8.03 (t, 1H), 7.95 (t, 1H), 7.56 (dd, 2H), 7.35 (d, 2H), 3.99 (t, 2H), 3.85 (t, 4H), 3.47 (t, 2H), 3.34 (t, 4H). | 419.4 |

TABLE 1-continued

| Characterization of compound data in examples | | | |
|---|---|---|---|
| Number | Structural formula | Nuclear magnetic resonance | Ms + 1 |
| 22 | 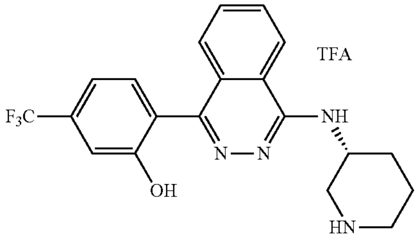 [SMILES: Oc1cc(C(F)(F)F)ccc1-c1nnc(N[C@@H]2CCCNC2)c2ccccc12] TFA | $^1$H NMR (400 MHz, DMSO) δ 11.20 (br, 1H), 10.51 (br, 1H), 8.40 (d, 1H), 7.87 (t, 1H), 7.79 (t, 1H), 7.51 (d, 1H), 7.45 (d, 1H), 7.34 – 7.25 (m, 3H), 7.21 (d, 1H), 4.49 – 4.36 (m, 1H), 3.20 – 3.10 (m, 1H), 3.10 – 2.97 (m, 1H), 2.73 – 2.60 (m, 2H), 2.11 – 2.05 (m, 1H), 1.86 – 1.76 (m, 1H), 1.73 – 1.55 (m, 2H). | 389.2 |
| 23 | 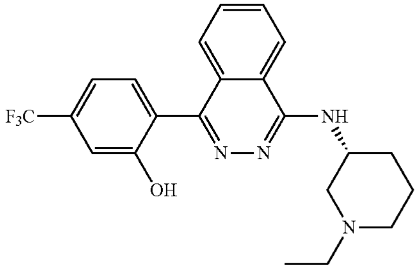 [SMILES: CCN1CCC[C@@H](Nc2nnc(-c3ccc(C(F)(F)F)cc3O)c3ccccc23)C1] | $^1$H NMR (400 MHz, DMSO) δ 10.41 (s, 1H), 8.39 (d, 1H), 7.88 – 7.83 (m, 1H), 7.77 (t, 1H), 7.50 (d, 1H), 7.44 (d, 1H), 7.33 – 7.22 (m, 2H), 7.11 (d, 1H), 4.48 – 4.36 (m, 1H), 2.83 – 2.78 (m, 2H), 2.41 – 2.36 (m, 2H), 2.04 – 1.90 (m, 4H), 1.61 – 1.58 (m, 1H), 1.48 – 1.44 (m, 1H), 1.02 (t, 3H). | 417.4 |
| 24 | 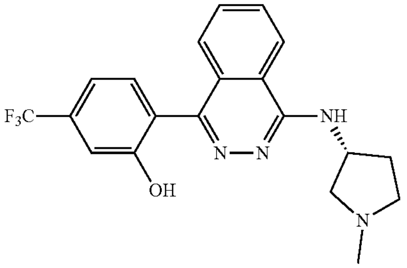 [SMILES: CN1CC[C@@H](Nc2nnc(-c3ccc(C(F)(F)F)cc3O)c3ccccc23)C1] | $^1$H NMR(DMSO) δ 10.36(s, 1H), 8.46(d, 1H), 7.88-7.85(m, 1H), 7.80-7.76(m, 1H), 7.52(d, 1H), 7.48-7.43(m, 2H), 7.30(d, 1H), 7.28(s, 1H), 4.77-4.72(m, 1H), 2.97-2.93(m, 1H), 2.79-2.75(m, 1H), 2.70-2.67(m, 1H), 2.56-2.54(m, 1H), 2.36-2.30(m, 4H), 2.01-1.95(m, 1H). | 389.4 |
| 25 | 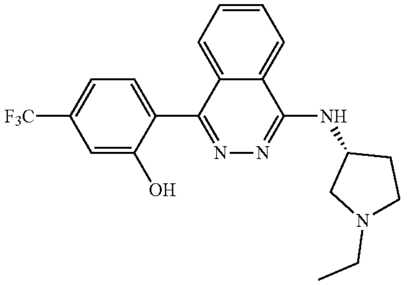 [SMILES: CCN1CC[C@@H](Nc2nnc(-c3ccc(C(F)(F)F)cc3O)c3ccccc23)C1] | $^1$H NMR(DMSO) δ 10.36(s, 1H), 8.44(d, 1H), 7.86-7.83(m, 1H), 7.80-7.76(m, 1H), 7.52(d, 1H), 7.45-7.40(m, 2H), 7.30(d, 1H), 7.27(s, 1H), 4.75-4.72(m. 1H), 2.97-2.93(m, 1H), 2.79-2.75(m, 1H), 2.70-2.67(m, 1H), 2.56-2.54(m, 1H), 2.36-2.30(m, 3H), 2.01-1.95(m, 1H), 1.24(t, 3H). | 403.4 |
| 26 | 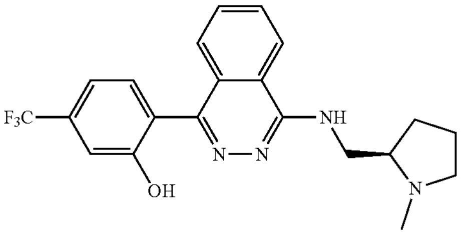 [SMILES: CN1CCC[C@@H]1CNc1nnc(-c2ccc(C(F)(F)F)cc2O)c2ccccc12] | $^1$H NMR (400 MHz, DMSO) δ 10.43 (s, 1H), 8.34 (d, 1H), 7.91 (t, 1H), 7.87 – 7.81 (m. 1H), 7.51 (t, 2H), 7.32 – 7.30 (m, 3H), 3.94 – 3.83 (m, 2H), 3.20 – 3.11 (m, 2H), 2.73 – 2.63 (m, 1H), 2.15 – 2.05 (m, 1H), 1.94 – 1.79 (m, 3H), 1.25 (d, 3H). | 403.4 |

TABLE 1-continued

| Number | Structural formula | Nuclear magnetic resonance | Ms + 1 |
|---|---|---|---|
| Characterization of compound data in examples | | | |
| 27 | 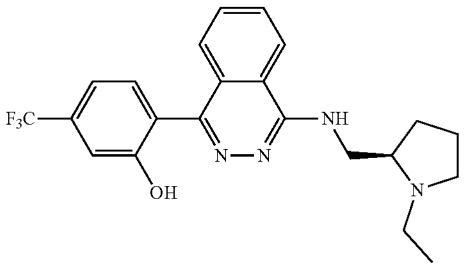 [SMILES: CCN1CCC[C@@H]1CNc1nnc(-c2ccc(C(F)(F)F)cc2O)c2ccccc12] | $^1$H NMR (400 MHz, DMSO) δ 10.43 (s, 1H), 8.34 (d, 1H), 7.92 (t, 1H), 7.88 - 7.80 (m, 1H), 7.51 (t, 2H), 7.32 - 7.30 (m, 3H), 3.94 - 3.80 (m, 2H), 3.20 - 3.11 (m, 2H), 2.73 - 2.63 (m. 1H), 2.15 - 2.05 (m, 2H), 1.94 - 1.79 (m, 4H), 1.24 (t, 3H). | 417.4 |
| 28 | 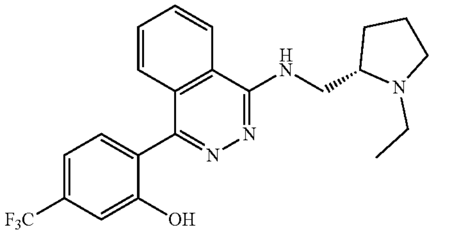 [SMILES: CCN1CCC[C@H]1CNc1nnc(-c2ccc(C(F)(F)F)cc2O)c2ccccc12] | $^1$H NMR (400 MHz, DMSO) δ 10.42 (s, 1H), 8.34 (d, 1H), 7.92 (t, 1H), 7.88 - 7.79 (m, 1H), 7.50 (t, 2H), 7.32 - 7.30 (m, 3H), 3.94 - 3.80 (m, 2H), 3.20 - 3.11 (m, 2H), 2.73 - 2.63 (m. 1H), 2.15 - 2.01 (m, 2H), 1.94 - 1.78 (m, 4H), 1.23 (t, 3H). | 417.4 |
| 29 | 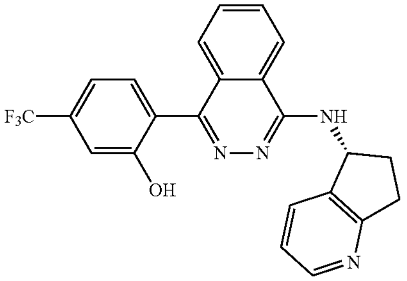 [SMILES: Oc1cc(C(F)(F)F)ccc1-c1nnc(N[C@@H]2CCc3ncccc32)c2ccccc12] | $^1$H NMR 400 MHz, DMSO-d6) δ 10.42 (s, 1H), 8.58 - 8.51 (m, 1H), 8.35 (dd, 1H), 8.10 - 8.04 (m, 1H), 7.82 (d, 1H), 7.75 - 7.70 (m, 3H), 7.65 (dd, 1H), 7.54 (s, 1H), 7.35 (d, 1H), 7.13 (m, 1H), 5.66 - 5.51 (m, 1H), 3.08 - 3.05 (m, 2H), 2.57 - 2.54 (m, 1H), 2.46 - 2.43 (m, 1H). | 423.5 |
| 30 | 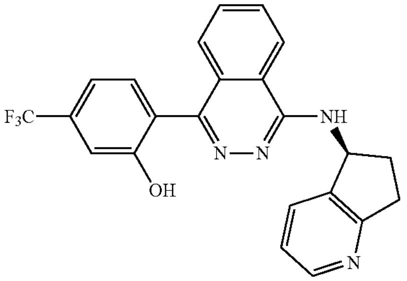 [SMILES: Oc1cc(C(F)(F)F)ccc1-c1nnc(N[C@H]2CCc3ncccc32)c2ccccc12] | $^1$H NMR 400 MHz,DMSO-d6) δ 10.42 (s, 1H), 8.58 - 8.51 (m, 1H), 8.35 (dd, 1H), 8.10 - 8.04 (m, 1H), 7.82 (d, 1H), 7.75 - 7.70 (m, 3H), 7.65 (dd, 1H), 7.54 (s, 1H), 7.35 (d, 1H), 7.13 (m, 1H), 5.66 - 5.51 (m, 1H), 3.08 - 3.05 (m, 2H), 2.57 - 2.54 (m, 1H), 2.46 - 2.43 (m, 1H). | 423.5 |
| 31 | 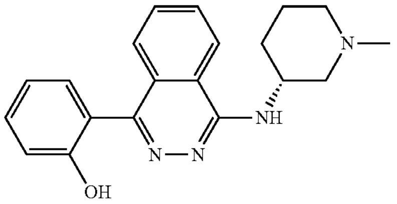 [SMILES: CN1CCC[C@@H](Nc2nnc(-c3ccccc3O)c3ccccc23)C1] | $^1$H NMR(DMSO-d6) δ 9.66 (s, 1H), 8.37(d, 1H), 7.85-7.75(m, 2H), 7.48(d, 1H), 7.33-7.26(m, 2H), 7.04-6.93(m, 3H). 4.44-4.35(m, 1H), 3.09-3.07(m, 1H), 2.72-2.69(m, 1H), 2.21(s, 3H), 2.00-1.88(m, 3H), 1.77-1.73(m, 1H), 1.62-1.59(m, 1H), 1.49-1.39(m, 1H). | 335.4 |

TABLE 1-continued

| Characterization of compound data in examples | | | |
|---|---|---|---|
| Number | Structural formula | Nuclear magnetic resonance | Ms + 1 |
| 32 | 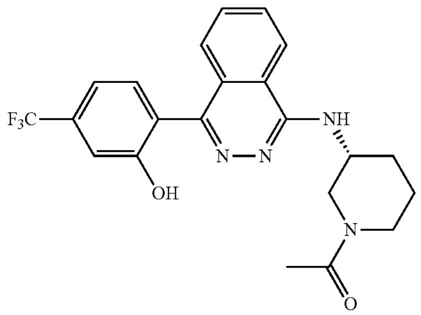 [SMILES: CC(=O)N1CCC[C@@H](Nc2nnc(-c3ccc(C(F)(F)F)cc3O)c3ccccc23)C1] | $^1$H NMR(DMSO-d6) δ 10.37(s, 1H), 8.45-8.41(m, 1H), 7.94-7.89(m, 1H), 7.84-7.78(m, 1H), 7.72-7.65(m, 1H), 7.53(d, 1H), 7.47(d, 1H), 7.32-7.28(m, 2H), 4.23-4.20(m, 1H), 3.08-3.05(m, 1H). 2.77-2.64(m, 2H), 2.14-2.12(m, 1H), 2.04(s, 3H), 1.83-1.81(m, 1H), 1.68-1.64(m, 1H), 1.48-1,46(m, 1H), 1.38-1.33(m, 1H). | 431.5 |
| 33 | 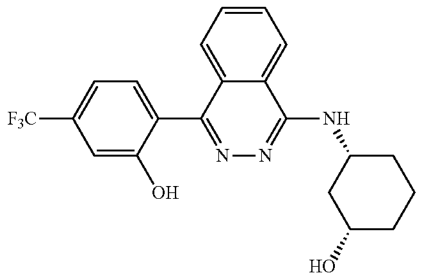 [SMILES: Oc1cc(C(F)(F)F)ccc1-c1nnc(N[C@@H]2CCC[C@H](O)C2)c2ccccc12] Isomer 1 (Rf = 0.2) | $^1$H NMR(DMSO-d6) δ 10.35(s, 1H), 8.39-8.37(m, 1H), 7.87-7.83(m, 1H), 7.79-7.75(m, 1H), 7.52-7.50(m, 1H). 7.45-7.43(m, 1H), 7.31-7.26(m, 3H), 4.72-4.71(m, 1H), 4.31-4.29(m, 1H), 3.57-356(m, 1H), 2.29-2.26(m, 1H), 2.02-1.99(m, 1H), 1.88-1.85(m, 1H). 1.78-1.75(m, 1H), 1.41-1.28(m, 3H), 1.19-1.13(m, 1H). | 404.5 |
| 34 | 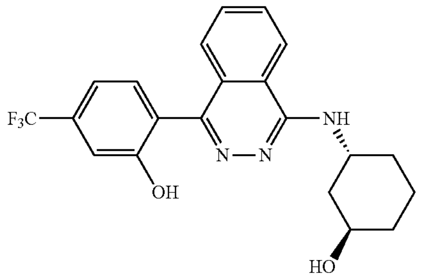 [SMILES: Oc1cc(C(F)(F)F)ccc1-c1nnc(N[C@@H]2CCC[C@@H](O)C2)c2ccccc12] Isomer 2 (Rf = 0.3) | $^1$H NMR(DMSO-d6) δ 10.43(s, 1H), 8.46-8.44(m, 1H), 7.89-7.85(m, 1H), 7.82-7.78(m, 1H), 7.53-7.51(m, 1H), 7.46-7.44(m, 1H), 7.32-7.28(m, 3H), 4.66(s, 1H), 4.51-4.48(m, 1H), 4.09-4.06(m, 1H), 2.04-1.93(m, 2H), 1.81-1.71(m, 2H), 1.62-1.54(m, 2H), 1.48-1.39(m, 2H). | 404.5 |
| 35 | 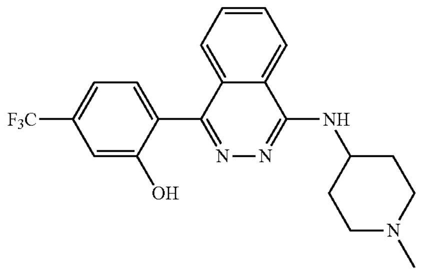 [SMILES: CN1CCC(Nc2nnc(-c3ccc(C(F)(F)F)cc3O)c3ccccc23)CC1] | $^1$H NMR (400 MHz, DMSO) δ 10.40 (s, 1H), 8.44 (d, 1H), 7.89 (t, 1H), 7.79 (t, 1H), 7.51 (d, 1H), 7.46 (d, 1H), 7.42 – 7.31 (m, 3H), 4.55 – 4.34 (m, 1H), 3.13 – 2.97 (m, 2H), 2.72 (s, 3H), 2.29 – 2.20 (m, 2H), 2.04 – 1.94 (m, 2H), 1.51 – 1.38 (m, 2H). | 403.4 |
| 36 | 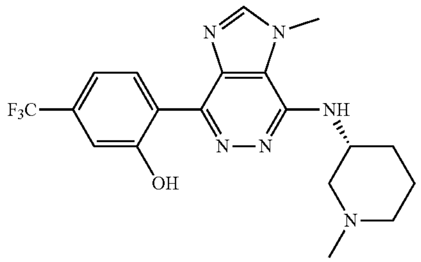 [SMILES: CN1CCC[C@@H](Nc2nnc(-c3ccc(C(F)(F)F)cc3O)c3ncn(C)c23)C1] | $^1$H NMR (400 MHz, DMSO) δ 15.54 (s, 1H), 9.49 (d, 1H), 8.58 (s, 1H), 7.30 (d, 1H), 7.24 (s, 1H), 6.40 (d, 1H), 4.51 – 4.39 (m, 1H), 4.21 (s, 3H), 3.20 – 3.03 (m, 1H), 2,88 – 2.71 (m, 1H), 2.45 – 2.25 (m, 4H), 1.99 – 1.79 (m, 2H), 1.74 – 1.57 (m, 2H), 1.36 – 1.32 (m, 1H). | 407.4 |

TABLE 1-continued

| Characterization of compound data in examples | | | |
|---|---|---|---|
| Number | Structural formula | Nuclear magnetic resonance | Ms + 1 |
| 37 | 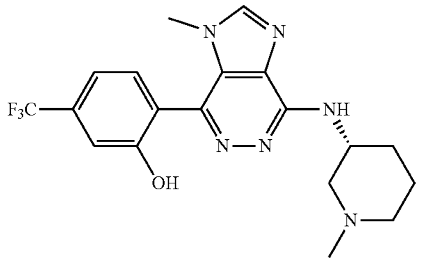 [SMILES: CN1CCC[C@@H](Nc2nnc(-c3ccc(C(F)(F)F)cc3O)c3c2ncn3C)C1] | $^1$H NMR (400 MHz, DMSO) δ 10.58 (s, 1H), 8.30 (s, 1H), 7.55 (d, 1H), 7.31 (d, 1H), 7.28 (s, 1H), 6.68 (br, 1H), 4.52 - 4.38 (m, 1H), 3.51 (s, 3H), 3.04 - 2.89 (m, 1H), 2.74 - 2.59 (m, 1H), 2.37 - 2.17 (m, 4H), 1.88 - 1.79 (m, 1H), 1.79 - 1.70 (m, 1H), 1.67 - 1.53 (m, 2H), 1.38 - 1.27 (m, 1H). | 407.4 |
| 38 | 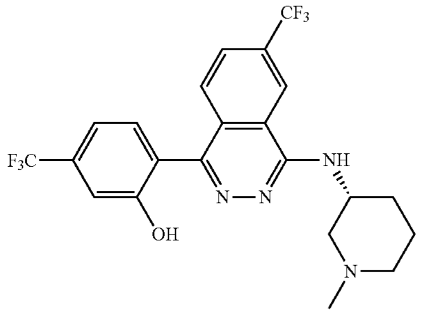 [SMILES: CN1CCC[C@@H](Nc2nnc(-c3ccc(C(F)(F)F)cc3O)c3ccc(C(F)(F)F)cc23)C1] | $^1$H NMR (400 MHz, DMSO-$d_6$) δ 10.72 (s, 1H), 9.09 (s, 1H), 8.17 (d, 1H), 7.71 (d, 2H), 7.56 (d, 1H), 7.40 (s, 1H), 7.35 (d, 1H), 4.79 - 4.65 (m, 1H), 3.84 - 3.61 (m, 1H), 3.03 - 2.89 (m, 2H), 2.88 - 2.70 (m. 4H), 2.22 - 2.06 (m, 1H), 2.07 - 1.91 (m, 2H), 1.90 - 1.74 (m, 1H). | 471.5 |
| 39 | 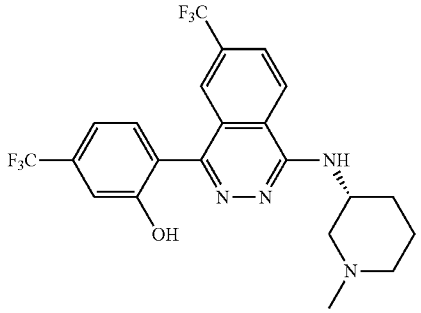 [SMILES: CN1CCC[C@@H](Nc2nnc(-c3ccc(C(F)(F)F)cc3O)c3cc(C(F)(F)F)ccc23)C1] | $^1$H NMR (400 MHz, DMSO-$d_6$) δ 10.55 (s, 1H), 9.49 (s, 1H), 8.17 (d, 1H), 7.71 (d, 2H), 7.56 (d, 1H), 7.40 (s, 1H), 7.35 (d, 1H),4.90 - 4.84 (m, 1H), 3.84 - 3.61 (m, 1H), 3.03 - 2.89 (m, 2H), 2.88 - 2.70 (m, 4H), 2.22 - 2.06 (m, 1H), 2.07 - 1.91 (m, 2H), 1.90 - 1.74 (m, 1H). | 471.5 |
| 40 | 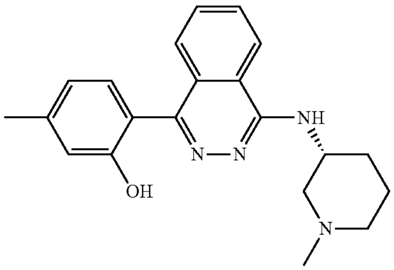 [SMILES: Cc1ccc(-c2nnc(N[C@@H]3CCCN(C)C3)c3ccccc23)c(O)c1] | $^1$H NMR(DMSO-d6) δ 9.60 (s, 1H), 8.39 (d, 1H), 7.86-7.83(m, 1H), 7.78-7.76(m, 1H), 7.52(d, 1H), 7.17-7.15(m, 2H), 6.80-6.76(m, 2H), 4.53-4.47(m, 1H), 3.26-3.24(m, 1H), 2.97-2.90(m, 1H), 2.50(s, 3H), 2.45-2.39(m, 2H), 2.33(s, 3H), 2.03-1.98(m, 1H), 1.88-1.82(m, 1H), 1.73-1.62(m, 1H), 1.59-1.52(m, 1H). | 349.2 |
| 41 | 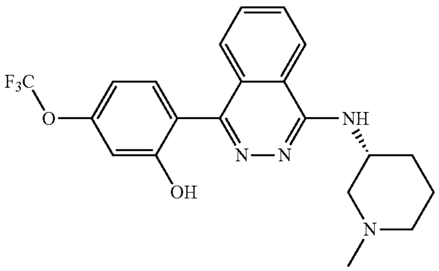 [SMILES: CN1CCC[C@@H](Nc2nnc(-c3ccc(OC(F)(F)F)cc3O)c3ccccc23)C1] | $^1$H NMR (400 MHz, DMSO) δ 10.35 (s, 1H), 8.38 (d, 1H), 7.85 (t, 1H), 7.78 (t, 1H), 7.45 (d, 1H), 7.42 - 7.37 (m, 1H), 7.09 (d, 1H), 6.94 - 6.92 (m, 2H), 4.47 - 4.35 (m, 1H), 3.12 - 3.01 (m, 1H), 2.75 - 2.64 (m, 1H), 2.21 (s, 3H), 2.02 - 1.84 (m, 3H), 1.80 - 1.69 (m, 1H), 1.67 - 1.54 (m, 1H), 1,52 - 1.38 (m, 1H). | 419.5 |

TABLE 1-continued

| Characterization of compound data in examples | | | |
|---|---|---|---|
| Number | Structural formula | Nuclear magnetic resonance | Ms + 1 |
| 43 | 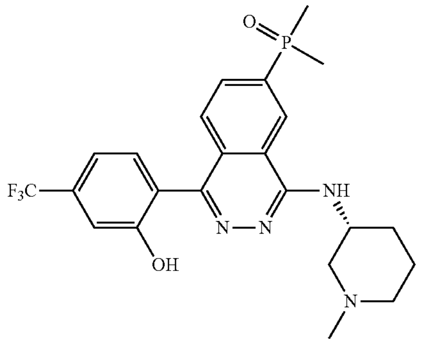 [SMILES: CN1CCC[C@@H](Nc2nnc(-c3ccc(C(F)(F)F)cc3O)c3ccc(P(C)(C)=O)cc23)C1] | $^1$H NMR(DMSO) δ 10.38(s, 1H), 8.76(d, 1H), 8.13-8.09(m, 1H), 7.91(d, 1H), 7.56-7.52(m, 2H), 7.33-7.29(m, 2H), 4.57-4.49(m, 1H), 3.28-3.19(m, 2H), 2.93-2.81(m, 1H), 2.33(s, 3H), 2.20-1.95(m, 3H), 1.85-1.75(m, 7H), 1.58-1.46(m, 1H). | 479.6 |
| 44 | 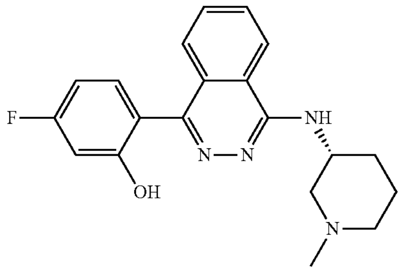 [SMILES: CN1CCC[C@@H](Nc2nnc(-c3ccc(F)cc3O)c3ccccc23)C1] | $^1$H NMR(DMSO-d6) δ 10.11(s, 1H), 8.97-8.90(m, 1H), 8.68(d, 1H), 8.16-8.12(m, 1H), 8.06-8.02(m, 1H), 7.65-7.58(m, 3H), 7.52-7.47(m, 1H), 4.48-4.27(m, 1H), 3.78-3.74(m, 1H), 3.51-3.48(m, 1H), 3.05-2.94(m, 2H), 2.88-2.86(m, 3H), 2.24-2.15(m, 1H), 2.05-2.01(m, 1H), 1.90-1.78(m, 1H), 1.72-1.63(m, 1H). | 353.2 |
| 45 | 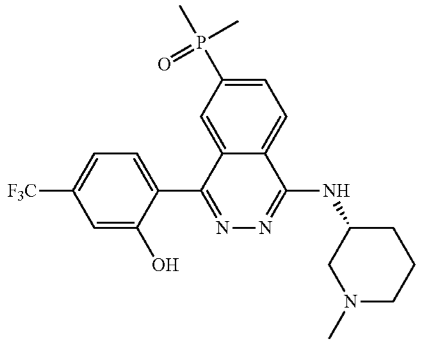 [SMILES: CN1CCC[C@@H](Nc2nnc(-c3ccc(C(F)(F)F)cc3O)c3cc(P(C)(C)=O)ccc23)C1] | $^1$H NMR(DMSO) δ 10.43(s, 1H), 8.53(d, 1H), 8.22-8.17(m, 1H), 7.60(d, 1H), 7.56-7.52(m, 2H), 7.33-7.29(m, 2H), 4.57-4.49(m, 1H), 3.28-3.19(m, 2H), 2.93-2.81(m, 1H), 2.30(s, 3H), 2.18-1.96(m, 3H), 1.85-1.82(m, 1H), 1.69(s, 3H), 1.66(s, 3H), 1.58-1.46(m, 1H). | 479.6 |
| 46 | 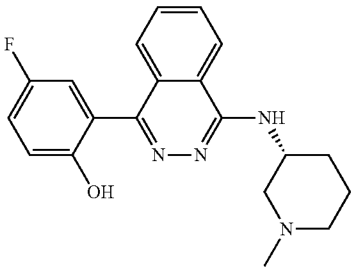 [SMILES: CN1CCC[C@@H](Nc2nnc(-c3cc(F)ccc3O)c3ccccc23)C1] | $^1$H NMR(DMSO-d6) δ 9.70(s, 1H), 8.53-8.40(m, 1H), 7.89-7.86(m, 1H), 7.83-7.80(m, 1H), 7.58-7.49(m, 2H), 7.20-7.15(m, 1H), 7.11-7.08(m. 1H), 7.02-6.99(m, 1H), 4.77-4.68(m, 1H), 3.65-3.55(m, 1H), 2.89-2.67(m, 5H), 2.08-1.94(m, 2H), 1.88-1.78(m, 2H), 1.73-1.64(m, 1H). | 353.2 |
| 47 | 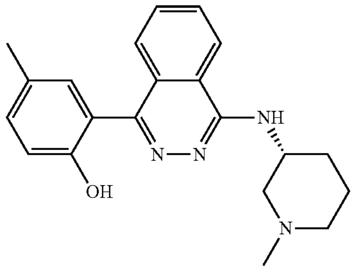 [SMILES: Cc1ccc(O)c(-c2nnc(N[C@@H]3CCCN(C)C3)c3ccccc23)c1] | $^1$H NMR(DMSO-d6) δ 9.40 (s, 1H), 8.47-8.39(m, 1H), 7.86-7.83(m, 1H), 7.80-7.76(m, 1H), 7.50(d, 1H), 7.15-7.07(m,3H), 6.89(d, 1H), 4.64-4.51(m, 1H), 3.07-2.95(m, 1H), 2.33-2.14(m, 5H), 2.02-1.98(m, 1H), 1.90(s, 3H), 1.77-1.67(m, 2H), 1.64-1.57(m, 1H), 1.52-1.43(m, 1H). | 349.2 |

TABLE 1-continued

| Characterization of compound data in examples | | | |
|---|---|---|---|
| Number | Structural formula | Nuclear magnetic resonance | Ms + 1 |
| 48 | 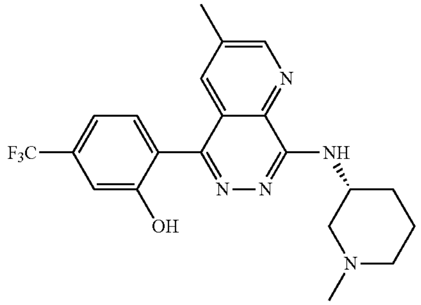 [SMILES: Cc1cnc2c(N[C@@H]3CCCN(C)C3)nnc(-c3ccc(C(F)(F)F)cc3O)c2c1] | $^1$H NMR($CDCl_3$) δ 8.91(s, 1H), 8.24(s, 1H), 7.62(d, 1H), 7.42(s, 1H), 7.32(s, 1H), 7.26-7.23(m, 1H), 4.59-4.57(m, 1H), 2.74-2.59(m, 6H), 2.36-2.28(m, 4H), 1.92-1.80(m, 3H), 1.75-1.67(m, 1H). | 418.6 |
| 49 | 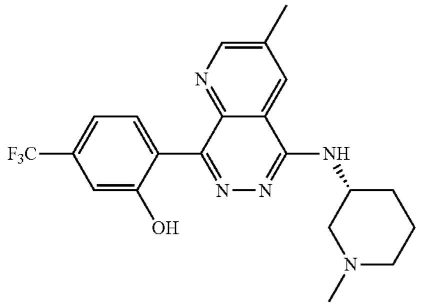 | $^1$H NMR(DMSO) δ 12.06(s, 1H), 9.01(s, 1H), 8.72(s, 1H), 8.28(d, 1H), 7.46(d, 1H), 7.25(d, 1H), 7.22(s, 1H), 4.45-4.41(m, 1H), 3.14-3.12(m. 1H), 2.79-2.76(m, 1H), 2.56(s, 3H), 2.28(s, 3H), 2.02-1.99(m, 3H), 1.81-1.78(m, 1H), 1.67-1.59(m, 1H), 1.51-1.44(m, 1H). | 418.6 |
| 50 | 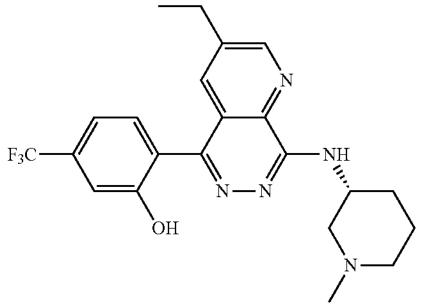 [SMILES: CCc1cnc2c(N[C@@H]3CCCN(C)C3)nnc(-c3ccc(C(F)(F)F)cc3O)c2c1] | $^1$H NMR (400 MHz, DMSO-d6) δ 9.88 (s, 1H), 9.15 (s, 1H), 8.69 (s, 1H), 7.85 (s, 1H), 7.60 (d, 1H), 7.41 - 7.32 (m, 2H), 4.65- 4.63 (m, 1H), 3.08 - 3.06 (m, 1H), 2.90- 2.84 (m, 6H), 2.54 - 2.50 (m, 1H), 2.20 - 1.93 (m, 2H), 1.92 - 1,72 (m, 2H), 1.24 - 1.20 (m, 4H). | 432.6 |
| 51 | 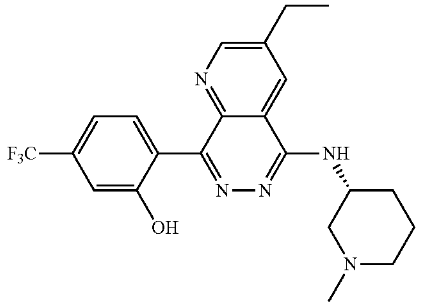 [SMILES: CCc1cnc2c(-c3ccc(C(F)(F)F)cc3O)nnc(N[C@@H]3CCCN(C)C3)c2c1] | $^1$H NMR (400 MHz, DMSO-$d_6$) δ 9.61 (s, 1H) 8.31 (d, 1H), 8.12 (d, 1H), 7.72 (d, 1H), 7.66 (dd, 1H), 7.38 (d, 1H), 6.47 (d, 1H), 4.07- 4.03 (m, 1H), 3.05 - 3.01 (m, 1H), 2.90- 2.86 (m, 2H), 2.81- 2.76 (m, 1H), 2.67 - 2.63 (m, 1H), 2.54 - 2.50 (m, 1H), 2.28 - 2.23 (m, 2H), 1.89 - 1.86 (m, 1H), 1.78 - 1.58 (m, 3H), 1.36 - 1.30 (m, 3H). | 432.6 |
| 52 | 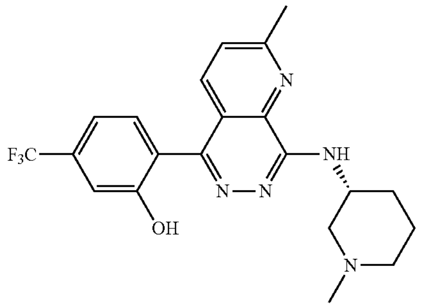 [SMILES: Cc1ccc2c(-c3ccc(C(F)(F)F)cc3O)nnc(N[C@@H]3CCCN(C)C3)c2n1] | $^1$H NMR (400 MHz, DMSO-$d_6$) δ 10.46 (d, 1H), 7.80 (d, 1H), 7.72 (d, 1H), 7.57 (d, 1H), 7.34 - 7.26 (m, 2H), 7.14 (dd, 1H), 4.46 - 4.42 (m, 1H), 2.75 - 2.53 (m, SH), 2.32 - 2.28 (m, 3H), 1.76 - 1.72 (m, 4H), 1.61 - 1.57(m, 1H), 1.36 - 1.32 (m, 1H). | 418.6 |

TABLE 1-continued

| Characterization of compound data in examples | | | |
|---|---|---|---|
| Number | Structural formula | Nuclear magnetic resonance | Ms + 1 |
| 53 | 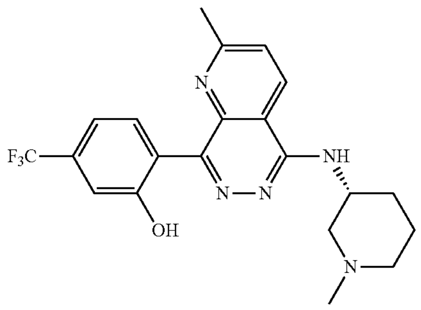 | $^1$H NMR (400 MHz, DMSO-d6) δ 12.25 (s, 1H), 8.84 (d, 1H), 8.38 (d, 1H), 7.84 (d, 1H), 7.64 (s, 1H), 7.28 – 7.20 (m, 2H), 4.46 – 4.42 (m, 1H), 2.96 – 2.93 (m, 2H), 2.68 – 2.65 (m, 3H), 2.45 – 2.42(m, 3H), 1.94 – 1.90 (m, 2H), 1.69 – 1.66 (m, 2H), 1.57 – 1.52 (m, 1H), 1.26 – 1.18 (m, 1H). | 418.6 |
| 54 | 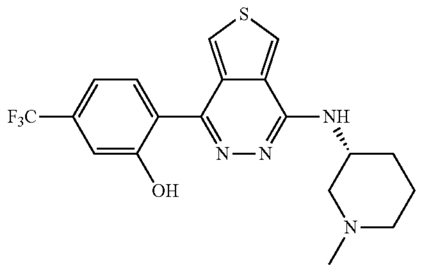 [SMILES: CN1CCC[C@@H](Nc2nnc(-c3ccc(C(F)(F)F)cc3O)c3cscc23)C1] | $^1$H NMR(DMSO-d6) δ 10,43(s, 1H), 8.82(s, 1H), 8.57(s, 1H), 8.06(d, 1H), 7.94(m, 1H), 7.32-7.28(m, 2H). 4.53-4.48(m, 1H), 3.17-3.15(m, 1H), 2.67-2.62(m, 2H), 2.06-1.91(m, 4H), 1.74-1.72(m, 1H), 1.60-1.55(m, 2H), 1.44-1.41(m, 1H). | 409.4 |
| 55 | 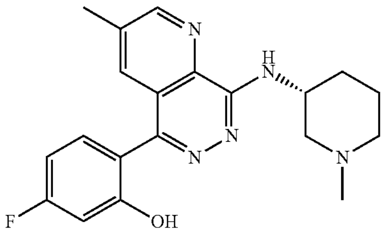 [SMILES: Cc1cnc2c(N[C@@H]3CCCN(C)C3)nnc(-c3ccc(F)cc3O)c2c1] | $^1$H NMR(DMSO) δ 9.40(s, 1H), 8.92(s, 1H), 8.65(s, 1H), 8.16-8.12(m, 1H), 8.08-8.04(m, 1H), 7.52-7.26(m, 2H), 4.50-4.48(m, 1H), 2.72-2.60(m, 6H), 2.36-2.30(m, 4H), 1.94-1.82(m, 3H). 1.76-1.60(m, 1H). | 368.6 |
| 56 | 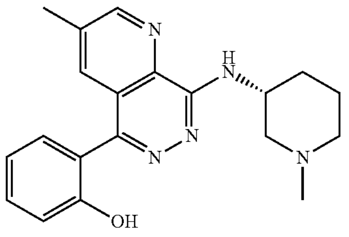 [SMILES: Cc1cnc2c(N[C@@H]3CCCN(C)C3)nnc(-c3ccccc3O)c2c1] | $^1$H NMR(DMSO) δ 9.82(s, 1H), 8.96(s, 1H), 7.70(s, 1H), 7.33-7.26(m, 2H), 7.04-6.93(m, 3H), 4.46-4.01(m, 1H), 3.51-3.43(m, 1H), 2.50(s, 3H), 2.35-2.30(m, 6H), 1.80-1.74(m, 3H), 1.62-1.54(m, 1H). | 350.6 |
| 57 | 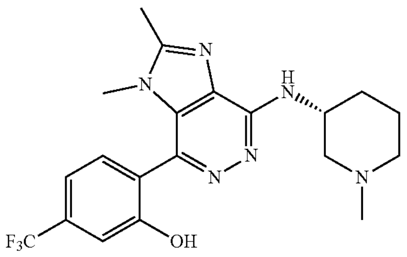 [SMILES: Cc1nc2c(N[C@@H]3CCCN(C)C3)nnc(-c3ccc(C(F)(F)F)cc3O)c2n1C] | $^1$H NMR (400 MHz, DMSO) δ 10.52 (s, 1H), 7.54 (d, 1H), 7.31 (d, 1H), 7.27 (s, 1H), 6.43 (d, 1H), 4.42 – 4.35 (m, 1H), 3.38 (s, 3H), 2.85 – 2.78 (m, 1H), 2.54 (s, 3H), 2.21 (s, 3H), 2.14 – 2.11 (m, 1H), 2.03 – 1.95 (m, 2H), 1.80 – 1.74 (m, 1H), 1.72 – 1.66 (m, 1H), 1.61 – 1.52 (m, 2H). | 421.6 |

TABLE 1-continued

| Characterization of compound data in examples | | | |
|---|---|---|---|
| Number | Structural formula | Nuclear magnetic resonance | Ms + 1 |
| 58 | 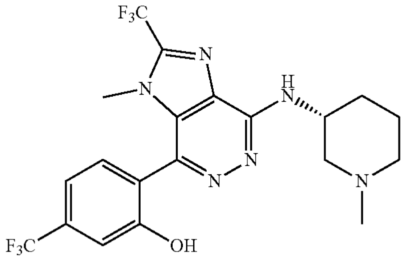 [SMILES: CN1CCC[C@@H](Nc2nnc(-c3ccc(C(F)(F)F)cc3O)c3c2nc(C(F)(F)F)n3C)C1] | $^1$H NMR (400 MHz, MeOD) δ 7.75 (d, 1H), 7.46 (d, 1H), 7.38 (s, 1H), 4.82 - 4.71 (m. 1H), 3.94 - 2.89 (m, 1H), 3.71 (s, 3H), 3.64 - 3.59 (m, 1H), 3.16 - 3.12 (m, 2H), 3.01 (s, 3H), 2.37 - 2.34 (m, 1H), 2.21 - 2.18 (m, 2H), 1.93 - 1.87 (m, 1H). | 475.4 |
| 59 | 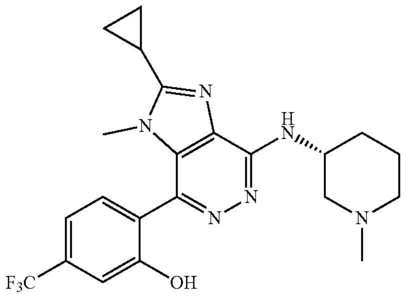 [SMILES: CN1CCC[C@@H](Nc2nnc(-c3ccc(C(F)(F)F)cc3O)c3c2nc(C2CC2)n3C)C1] | $^1$H NMR (400 MHz, MeOD) δ 7.71 (d, 1H), 7.42 (d, 1H), 7.35 (s, 1H), 4.76 - 4.71 (m, 1H), 3.86 - 2.80 (m, 1H), 3.70 (s, 3H), 3.62 - 3.57 (m, 1H), 3.11 - 3.07 (m, 2H), 2.98 (s, 3H), 2.37 - 2.34 (m, 1H), 2.15 - 2.11 (m, 3H), 1.93 - 1.87 (m, 3H), 1.32 - 1.25(m, 2H). | 447.4 |
| 60 | 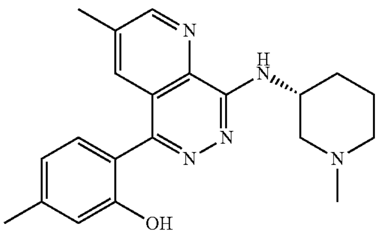 [SMILES: Cc1ccc(-c2nnc(N[C@@H]3CCCN(C)C3)c3ncc(C)cc23)c(O)c1] | $^1$H NMR(DMSO) δ 9.67(s, 1H), 8.95(s, 1H), 7.69(s, 1H), 7.25(s, 1H), 7.21 (d, 1H), 6.81(s. 1H), 6.79(d, 1H), 4.45-4.41(m, 1H), 3.41-3.33(m, 1H), 2.50(s, 3H), 2.47(s, 3H), 2.33-2.28(m. 6H), 1.78-1.71(m, 3H), 1.62-1.56(m, 1H). | 364.6 |
| 61 | 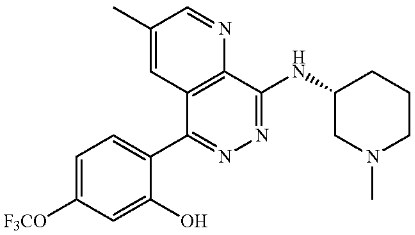 [SMILES: Cc1cnc2c(N[C@@H]3CCCN(C)C3)nnc(-c3ccc(OC(F)(F)F)cc3O)c2c1] | $^1$H NMR(DMSO) δ 9.6(s, 1H), 8.90(s, 1H), 7.64(s, 1H), 8.17-8.13(m, 1H), 8.08-8.04(m, 1H), 7.50-7.28(m, 2H), 4.55-4.48(m, 1H), 2.92-2.80(m, 6H), 2.36-2.30(m, 4H), 1.94-1.82(m, 3H), 1.72-1.62(m, 1H). | 434.6 |
| 62 | 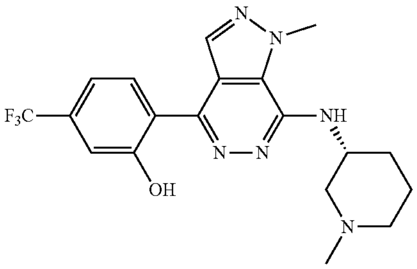 [SMILES: CN1CCC[C@@H](Nc2nnc(-c3ccc(C(F)(F)F)cc3O)c3cnn(C)c23)C1] | $^1$H NMR (400 MHz, DMSO-$d_6$) δ 10.99 (br, 1H), 8.54 (s, 1H), 7.55 (d, 1H), 7.46 (br, 1H), 7.03 (d, 1H), 6.9 (s, 1H), 4.69 - 4.51 (m, 1H), 3.94 - 3.83 (m, 4H), 3.67 - 3.55 (m, 1H), 3.24 - 3.09 (m, 2H), 3.34 (s, 3H), 2.42 - 2.34 (m, 1H), 2.26 - 2.05 (m, 2H), 1.95 - 1,91 (m, 1H). | 407.2 |

TABLE 1-continued

| Characterization of compound data in examples | | | |
|---|---|---|---|
| Number | Structural formula | Nuclear magnetic resonance | Ms + 1 |
| 63 | 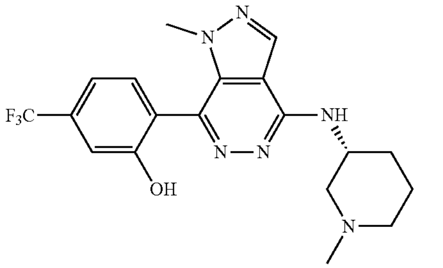 [SMILES: CN1CCC[C@@H](Nc2nnc(-c3ccc(C(F)(F)F)cc3O)c3c2cnn3C)C1] | $^1H$ NMR (400 MHz, MeOD) δ 8.76 (s, 1H) 7.71 (d, 1H), 7.43 (d, 1H), 7.34 (s, 1H), 4.69 – 4.51 (m, 1H), 3.94 – 3.83 (m, 4H), 3.67 – 3.55 (m, 1H), 3.24 – 3.09 (m, 2H), 3.34 (s. 3H), 2.42 – 2.34 (m, 1H), 2.26 – 2.05 (m, 2H), 1.93 – 1.82 (m, 1H). | 407.2 |
| 64 | 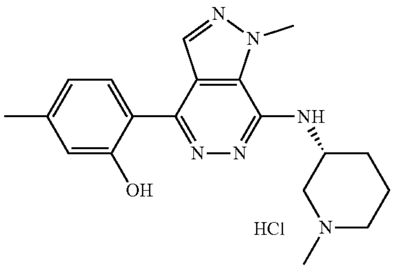 [SMILES: Cc1ccc(-c2nnc(N[C@@H]3CCCN(C)C3)c3c2cnn3C)c(O)c1 ; Cl] | $^1H$ NMR (400 MHz, DMSO-$d_6$) δ 10.99 (br, 1H), 8.54 (s, 1H), 7.55 (d, 1H), 7.46 (br, 1H),7.03 (d, 1H), 6.9 (s, 1H), 4.66 – 4.59 (m, 1H), 4.52(s, 3H), 3.58 – 3.55 (m, 1H), 3.34 – 3.22 (m, 2H), 3.04 – 2.98 (m, 1H), 2.68 – 2.61(m, 4H), 2.52(s, 3H), 2.21-2.18 (m, 1H), 2.08 – 1.79 (m, 3H). | 353.2 |
| 65 | 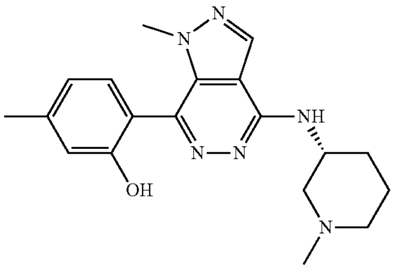 [SMILES: Cc1ccc(-c2nnc(N[C@@H]3CCCN(C)C3)c3cnn(C)c23)c(O)c1] | $^1H$ NMR (400 MHz, DMSO-$d_6$) δ 9.68 (s, 1H), 8.32 (s, 1H), 7.22 (d,1H), 7.18 (d, 1H), 6.78 (s, 1H), 6.77 (br, 1H), 4.30 – 4.20 (m, 1H),, 3.66 (s, 3H), 3.05 – 3.01 (m, 1H), 2.67 – 2.63 (m, 1H), 2.32 (s, 3H), 2.22 (s, 3H), 1.98 – 1.91 (m, 3H), 1.82 – 1.68 (m, 1H), 1.59 – 1.54 (m, 1H), 1.42 – 1.13 (m, 1H). | 353.2 |
| 66 | 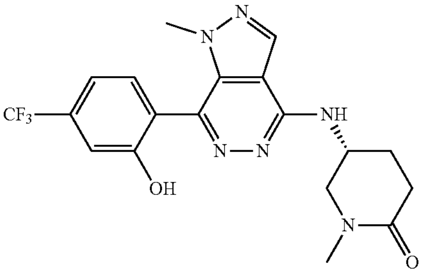 [SMILES: CN1C[C@H](Nc2nnc(-c3ccc(C(F)(F)F)cc3O)c3c2cnn3C)CCC1=O] | $^1H$ NMR (400 MHz, DMSO) δ 11.14 (s, 1H), 8.72 (s, 1H), 7.66 (d. 1H), 7.46 – 7.41 (m, 2H), 7.36 (s, 1H), 4.59 – 4.45 (m, 1H), 3.77 (s, 3H), 3.70 (dd, 2H), 2.88 (s, 3H), 2.52- 2.45 (m, 2H), 2.24 – 2.12 (m, 1H), 2.12 – 1.98 (m, 1H). | 421.2 |
| 67 | 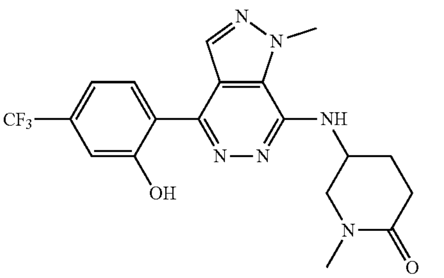 [SMILES: CN1CC(Nc2nnc(-c3ccc(C(F)(F)F)cc3O)c3cnn(C)c23)CCC1=O] | $^1H$ NMR (400 MHz, DMSO) δ 10.93 (s, 1H), 8.65 (s, 1H), 8.48 (s, 1H), 8.12 (d. 1H), 7.37 – 7.33 (m, 2H), 4.66 – 4.45 (m, 1H), 4.45 (s, 3H), 3.72- 3.68 (m, 1H), 3.54-3.49 (m, 1H), 2.88 (s,3H), 2.46- 2.43 (m, 2H), 2.19 – 2.09 (m, 2H). | 421.2 |

TABLE 1-continued

| Characterization of compound data in examples | | | |
|---|---|---|---|
| Number | Structural formula | Nuclear magnetic resonance | Ms + 1 |
| 68 | 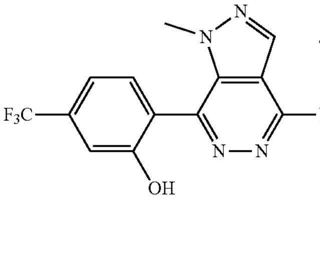 TFA | $^1$H NMR (400 MHz, DMSO) δ 10.97 (s, 1H), 9.85 (s, 1H), 8.67 (s, 1H), 7.54 - 7.38 (m, 2H), 6.95 - 6.85 (m, 2H), 4.25 - 4.13 (m, 1H), 3.78 (s, 3H), 3.61 (d, 2H), 3.15 - 3.05 (m, 2H), 2.87 (s, 3H), 2.38 - 2.25 (m, 2H), 1.98 - 1.82 (m, 2H). | 407.2 |
| 69 | 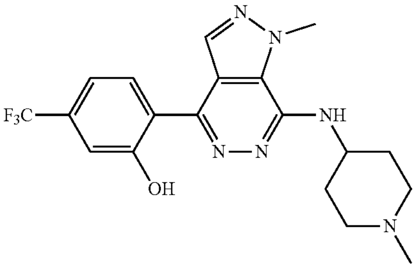 [SMILES: CN1CCC(Nc2nnc(-c3ccc(C(F)(F)F)cc3O)c3cnn(C)c23)CC1] | $^1$H NMR (400 MHz, DMSO) δ 9.78 (br, 1H), 8.64 (s, 1H), 7.97 (d, 1H), 7.15 (br, 1H), 6.90 - 6.85 (m, 2H), 4.44 (s, 3H), 4.35 - 4.23 (m, 1H), 3.58 (d, 2H), 3.15 - 3.05 (m, 2H), 2.84 (s, 3H), 2.35 - 2.25 (m, 2H), 1.98 - 1.92 (m, 2H). | 357.2 |
| 70 | 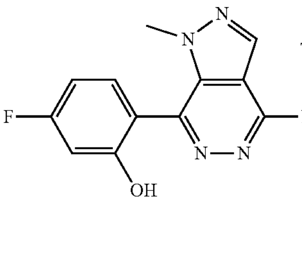 TFA | $^1$H NMR (400 MHz, DMSO) δ 10.97 (s, 1H), 9.85 (s, 1H), 8.67 (s, 1H), 7.54 - 7.38 (m, 2H), 6.95 - 6.85 (m, 2H), 4.25 - 4.13 (m, 1H), 3.78 (s, 3H), 3.61 (d, 2H), 3.15 - 3.05 (m, 2H), 2.87 (s, 3H), 2.38 - 2.25 (m, 2H), 1.98 - 1.82 (m, 2H). | 357.2 |
| 71 | 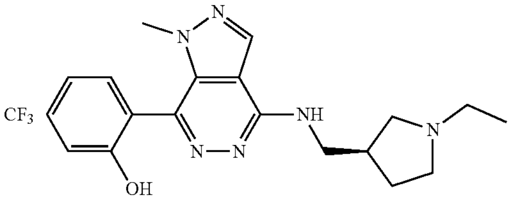 [SMILES: "CF3" ; CCN1CC[C@@H](CNc2nnc(-c3ccccc3O)c3c2cnn3C)C1] | $^1$H NMR (400 MHz, DMSO) δ 9.70 (br, 1H), 8.67 (s, 1H), 8.23 (d, 1H), 7.52 (br, 1H), 7.32 (d, 2H), 4.45 (s, 3H), 4.03 - 3.86 (m, 2H), 3.23 - 3.14 (m, 2H), 2.32 - 2.22 (m, 1H), 2.08 - 1.92 (m, 4H), 1.31 - 1.26 (m, 5H). | 421.2 |
| 72 | 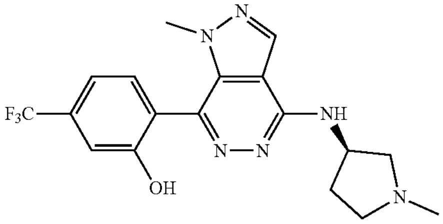 [SMILES: CN1CC[C@@H](Nc2nnc(-c3ccc(C(F)(F)F)cc3O)c3c2cnn3C)C1] | $^1$H NMR (400 MHz, DMSO) δ 11.05 (br, 1H), 8.55 (s, 1H), 7.63 (d, 1H), 7.42 - 7.32 (m, 3H), 4.89 - 4.79 (m, 1H), 3.87 - 3.80 (m, 2H), 3.76 (s, 3H), 3.01 - 2.89 (m, 5H), 2.73 - 2.63 (m, 1H), 2.38 - 2.30 (m, 1H). | 393.2 |
| 73 | 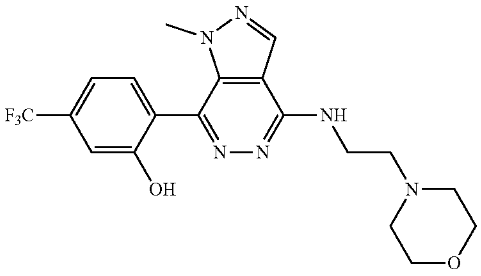 [SMILES: Cn1ncc2c(NCCN3CCOCC3)nnc(-c3ccc(C(F)(F)F)cc3O)c21] | $^1$H NMR (400 MHz, DMSO) δ9.50(s, 1H), 8.68(s, 1H), 8.18-8.16(m, 1H), 7.59(s, 1H), 7.35-7.33(2H), 4.45(s, 3H), 4.03-4.01(m, 2H), 3.89-3.87(m, 4H), 3.57-3.55(m, 2H), 3.47-3.33(m, 4H). | 423.2 |

TABLE 1-continued

| Characterization of compound data in examples | | | |
|---|---|---|---|
| Number | Structural formula | Nuclear magnetic resonance | Ms + 1 |
| 74 | 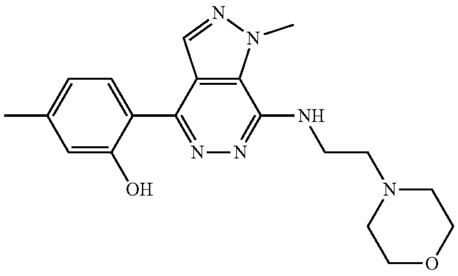 [SMILES: Cc1ccc(-c2nnc(NCCN3CCOCC3)c3c2cnn3C)c(O)c1] | $^1$H NMR (400 MHz, DMSO) δ10.37(s, 1H), 9.93(s, 1H), 8.65(s, 1H), 7.30-7.28(m, 1H), 6.90-6.88(m, 2H), 4.02-4.00(m, 2H), 3.93-3.83(m, 4H), 3.79(s, 3H), 3.49-3.47(m, 2H), 3.35-3.33(m, 4H), 2.37(s, 3H). | 369.2 |
| 75 | 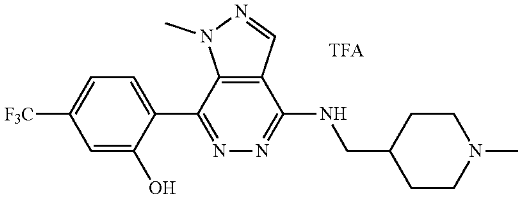 [SMILES: CN1CCC(CNc2nnc(-c3ccc(C(F)(F)F)cc3O)c3c2cnn3C)CC1] TFA | $^1$H NMR (400 MHz, DMSO) δ11.35(s, 1H), 10.01(br, 1H), 9.58(s, 1H), 8.70(s, 1H), 7.67-7.65(m, 1H), 7.43-7.41(m, 1H), 7.38(s, 1H), 3.77(s, 3H), 3.54-3.40(m, 5H), 2.99-2.91(m, 2H), 2.79(s, 3H), 2.05-2.02(m, 2H), 1.52-1.43(m, 2H). | 421.2 |
| 76 | 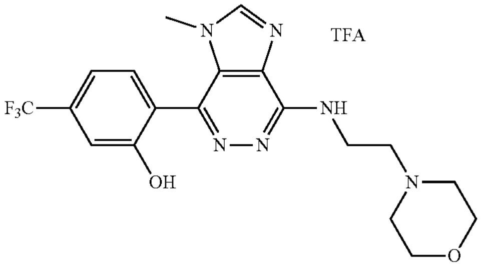 [SMILES: Cn1cnc2c(NCCN3CCOCC3)nnc(-c3ccc(C(F)(F)F)cc3O)c21] TFA | $^1$H NMR (400 MHz, DMSO) δ 11.54 (br, 1H), 9.22 (s, 1H), 8.71 (s, 1H), 7.65 (d. 1H), 7.41 (d, 2H), 4.12 – 4.06 m, 3H), 3.94 – 3.79 (m, 6H), 3.62 (s, 3H), 3.56 – 3.51 (m, 3H). | 423.2 |
| 77 | 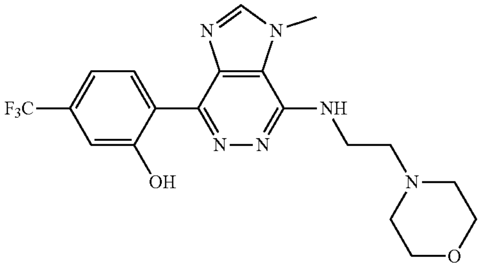 [SMILES: Cn1cnc2c(-c3ccc(C(F)(F)F)cc3O)nnc(NCCN3CCOCC3)c21] | $^1$H NMR (400 MHz, DMSO) δ 10.19 (s, 1H), 9.41 (d, 1H), 8.65 (s, 1H), 7.40 – 7.30 (m, 1H), 7.30 – 7.19 (m, 2H), 4.22 (s, 3H), 4.05 – 3.97 (m, 3H), 3.88 (br, 3H), 3.57 – 3.54 (m, 3H), 3.45 (br, 3H). | 423.2 |
| 78 | 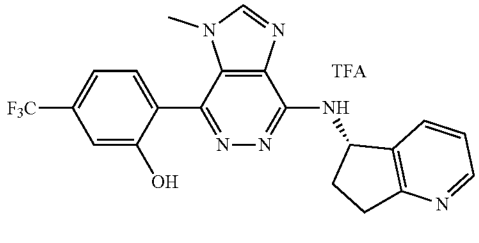 [SMILES: Cn1cnc2c(N[C@H]3CCc4ncccc43)nnc(-c3ccc(C(F)(F)F)cc3O)c21] TFA | $^1$H NMR (400 MHz, DMSO) δ 11.30 (br, 1H), 10.17 (s, 1H), 8.70 (s, 1H), 8.57 (d, 1H), 7.95 (d, 1H), 7.71 (d, 1H), 7.44 (d, 1H), 7.39 – 7.36 (m, 2H), 5.83 – 5.75 (m, 1H), 3.79 (s, 3H), 3.24 – 3.16 (m, 1H), 3.12 – 3.02 (m, 1H), 2.85 – 2.75 (m, 1H), 2.25 – 2.13 (m, 1H). | 427.2 |
| 79 | 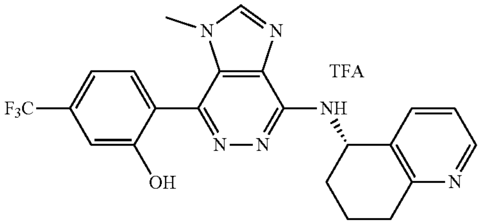 [SMILES: Cn1cnc2c(N[C@H]3CCCc4ncccc43)nnc(-c3ccc(C(F)(F)F)cc3O)c21] TFA | H NMR (400 MHz, DMSO) δ 11.29 (br, 1H), 10.11 (s, 1H), 8.69 (s, 1H), 8.61 (d, 1H), 8.07 (d, 1H), 7.69 (d, 1H), 7.51 – 7.42 (m, 2H), 7.38 (s, 1H), 5.51 – 5.45 (m, 1H), 3.79 (s, 3H), 3.08 – 2.99 (m, 2H), 2.25 – 2.16 (m, 1H), 2.12 – 1.91 (m, 3H). | 441.2 |

TABLE 1-continued
| Characterization of compound data in examples | | | |
|---|---|---|---|
| Number | Structural formula | Nuclear magnetic resonance | Ms + 1 |
| 80 | 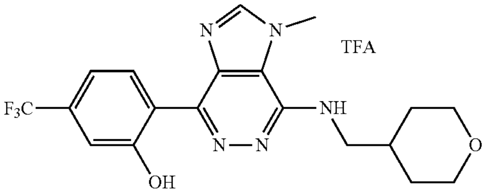 [SMILES: Cn1cnc2c(-c3ccc(C(F)(F)F)cc3O)nnc(NCC3CCOCC3)c21] | $^1$H NMR (400 MHz, DMSO) δ 11.30 (br, 1H), 9.46 (br, 1H), 8.68 (s, 1H), 7.64 (d, 1H), 7.40 (d. 1H), 7.37 (s, 1H), 3.60 (s, 3H), 2,99 - 2.85 (m, 2H), 2.85 - 2.73 (m, 4H), 2.08 - 1.95 (m, 3H), 1.49 - 1.40 (m, 2H). | 408.2 |
| 81 | 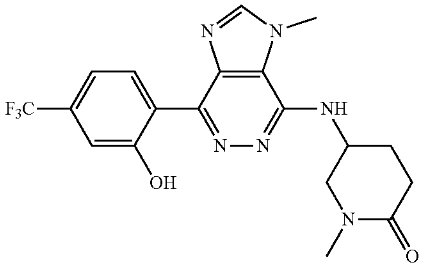 [SMILES: CN1CC(Nc2nnc(-c3ccc(C(F)(F)F)cc3O)c3ncn(C)c23)CCC1=O] | $^1$H NMR (400 MHz, DMSO) δ 9.60 (br, 1H), 8.73 (s, 1H), 7.67 (d, 1H), 7.42 (d, 1H), 7.37 (s, 1H), 3.74 - 3.59 (m, 6H), 2.86 (s, 3H), 2.44 - 2.40 (m, 2H), 2.16 - 2.07 (m, 2H). | 421.2 |
| 82 | 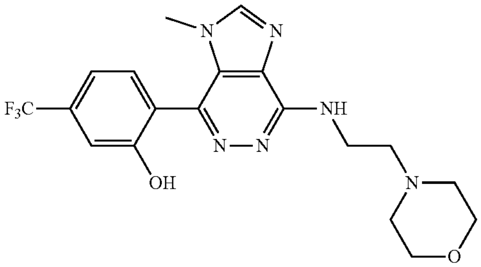 [SMILES: Cn1cnc2c(NCCN3CCOCC3)nnc(-c3ccc(C(F)(F)F)cc3O)c21] | $^1$H NMR (400 MHz, DMSO) δ 9.12 (br, 1H), 8.72 (s, 1H), 7.47 (dd, 1H), 6.92 (dd, 2H), 4.03 (br, 2H), 3.87 (br, 5H), 3.63 (s, 2H), 3.50 (br, 2H), 3.36 (br, 4H). | 373.2 |
| 83 | 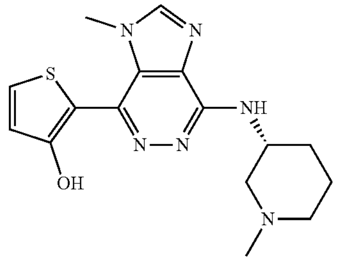 [SMILES: CN1CCC[C@@H](Nc2nnc(-c3sccc3O)c3c2ncn3C)C1] | $^1$H NMR (400 MHz, DMSO) δ 11.56(br, 1H), 8.29 (s, 1H), 7.50 (d, 1H), 6.78 (d, 1H), 6.51 (d, 1H), 4.45 - 4.33 (m, 1H), 3.72 (s, 3H), 3.58 -3.55 (m, 1H), 2.84 - 2.81 (m, 1H), 2.21 (s, 3H), 2.16 - 2.03 (m, 2H), 1.85 - 1.65 (m, 2H), 1.62 - 1.50 (m, 2H). | 345.2 |
| 84 | 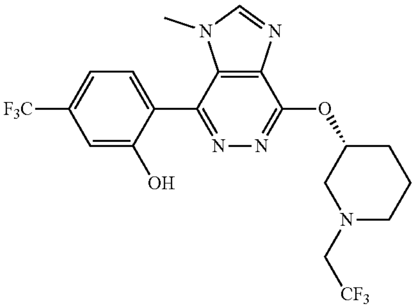 [SMILES: Cn1cnc2c(O[C@@H]3CCCN(CC(F)(F)F)C3)nnc(-c3ccc(C(F)(F)F)cc3O)c21] | $^1$H NMR (400 MHz, DMSO) δ 9.47 (br, 2H), 8.73 (s, 1H), 7.38(d, 1H), 7.34 - 7.27(m, 1H), 5.50 (br, 1H), 4.14 (s, 3H), 3.34 - 3.26 (m. 2H), 3.16 (dd, 1H), 2.95 (dd, 1H), 2.79 - 2.68 (m, 2H), 2.08 - 1.98 (m, 1H), 1.93 - 1.81 (m, 2H), 1.69 - 1.58 (m, 1H). | 476.2 |

TABLE 1-continued

Characterization of compound data in examples

| Number | Structural formula | Nuclear magnetic resonance | Ms + 1 |
|---|---|---|---|
| 85 | 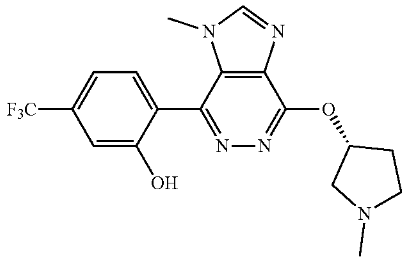 [SMILES: CN1CC[C@@H](Oc2nnc(-c3ccc(C(F)(F)F)cc3O)c3c2ncn3C)C1] | $^{1}$H NMR (400 MHz, DMSO) § 10.80 (br, 1H), 9.47 (d, 1H), 8.72 (s, 1H), 7.36 (d, 1H), 7.30 (s, 1H), 4.15 - 4.00 (m, 4H), 3.91 - 3.79 (m, 1H), 3.67 - 3.57 (m, 2H), 3.17 - 3.07 (m, 1H), 2.94 (s, 3H), 2.83 - 2.73 (m, 1H), 2.43 - 2.34 (m, 1H). | 394.2 |
| 86 | 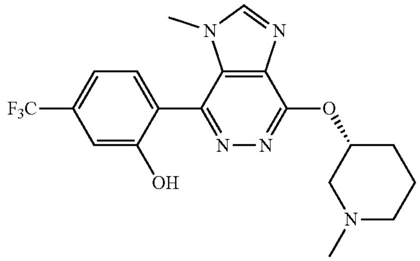 [SMILES: CN1CCC[C@@H](Oc2nnc(-c3ccc(C(F)(F)F)cc3O)c3c2ncn3C)C1] | $^{1}$H NMR (400 MHz, DMSO) δ 9.53 (d, 1H), 9.38 (br, 1H), 8.76 (s, 1H), 7.39 (d, 1H), 7.31 (s, 1H), 4.20 (s, 3H), 4.14 - 3.98 (m, 2H), 3.54 - 3.45 (m, 2H), 3.10 - 3.07 (m, 1H), 2.79 (s, 3H), 2.19 - 2.06(m, 2H), 2.00 - 1.86 (m, 2H). | 408.2 |
| 87 | 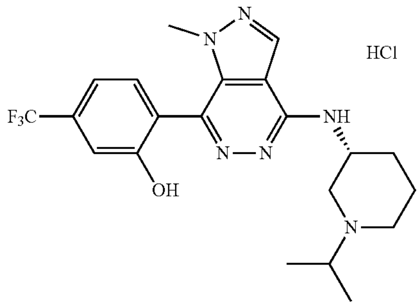 [SMILES: CC(C)N1CCC[C@@H](Nc2nnc(-c3ccc(C(F)(F)F)cc3O)c3c2cnn3C)C1 ; Cl] | $^{1}$H NMR (400 MHz, DMSO) δ 11.45 (s, 1H), 10.52 (br, 1H), 9.16 (br, 1H), 8.77 (s, 1H), 7.67 (d, 1H), 7.50 (d, 1H), 7.40 (d, 1H), 4.83 - 4.66 (m, 1H), 3.60 (s, 3H), 3.56 - 3.48 (m, 3H), 3.08 - 2.85 (m, 2H), 2.22 - 2.16 (m, 1H), 2.08 - 1.95 (m, 2H), 1.73 - 1.66 (m, 1H), 1.31 (1, 6H). | 435.2 |
| 88 | 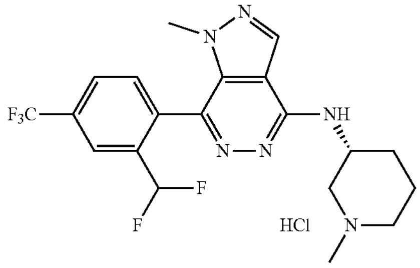 [SMILES: CN1CCC[C@@H](Nc2nnc(-c3ccc(C(F)(F)F)cc3C(F)F)c3c2cnn3C)C1 ; Cl] | $^{1}$H NMR (400 MHz, DMSO) δ 10.90 (br, 1H), 9.71 (br, 1H), 8.77 (s, 2H), 8.21 (d, 2H), 8.03 (d, 1H), 7.09 (t, 1H), 4.81 - 4.59 (m, 1H), 3.67 - 3.64 (m, 1H), 3.38 (s, 3H), 3.15 - 3.08 (m, 1H), 2.98 - 2.92 (m, 1H), 2.91 - 2.85 (m, 1H), 2.81 (s, 3H), 2.1 - 2.16 (d, 1H), 2.01 - 1.90 (m, 2H), 1.70 - 1.59 (m, 1H). | 441.2 |

Example 89: Cell Pyroptosis Test

In Vitro Activities of the Above Compounds were Demonstrated in the Following Assay:

In vitro activity screening was performed on small molecule compounds targeting inhibition on NLRP3 inflammasomes using THP-1 human monocytic cells (THP-1). THP-1 can be induced to differentiate into macrophages by phorbol ester (PMA), and the macrophages M1 can be induced to polarize by lipopolysaccharide (LPS) to release cytokines such as TNF-α, and IL-6, so as to establish a typical inflammatory model.

1. Experimental Materials:

RPMI Medium 1640 was purchased from Gibco company; penicillin and streptomycin were purchased from Hyclone company; lipopolysaccharide (LPS), phorbol ester (PMA), and nigericin were purchased from MedChemExpress (MCE) company; thiazolyl blue (MTT) was purchased from Beijing Solarbio Technology Co., Ltd.; sodium dodecyl sulfate (SDS) was purchased from Biofroxx company.

2. THP-1 Cell Culture:

THP-1 cells were cultured in 1640 medium+10% FBS+1% penicillin/streptomycin medium in a 37 °C, 5% $CO_2$ incubator.

3. THP-1 Pyroptosis Test:

THP-1 cells in a logarithmic growth phase were collected to prepare a $1\times10^6$ cells/mL cell suspension, PMA was added to achieve a final concentration of 300 ng/mL in the cell suspension, then $1\times10^5$ cells were inoculated to each well of a 96-well plate, and the cells were cultured in a 37 °C, 5% $CO_2$ cell incubator for 24 hours and induced to differentiate into macrophages.

The next day, LPS was added to stimulate and induce the cells to produce an inflammatory model. Specific operations were as follows, the original medium was removed from the well plate, 100 μL of 1640 medium containing 2 μg/mL LPS was added to each well, and then the 96-well plate was placed in the 37 °C, 5% $CO_2$ cell incubator to culture the cells for 3-4 hours, so as to establish the inflammatory model. A drug treatment group, an inflammatory model group, a normal cell group (including only cells and 1640 medium), and a blank control group (excluding cells but including only medium) were cultured in each 96-well plate. After LPS stimulation, each compound to be tested was diluted with the 1640 medium to a corresponding concentration (0.004-40 μM) and added to corresponding wells of the 96-well plate, with 50 μL per well and 3 repeated wells per sample concentration, 50 μL of 1640 medium was added in the inflammatory model group and the normal cell group, and then the 96-well plate was placed in the 37 °C, 5% $CO_2$ cell incubator to culture the cells for 30 min. After culture, 50 μL of 1640 medium containing 40 μM nigericin was added in the drug treatment group and the inflammatory model group respectively, where the nigericin can activate NLRP3 inflammasomes in cells and induce pyroptosis, 50 μL of 1640 medium was added in the normal cell group. In the 200 μL system of the 96-well plate, the final concentration of each drug was 0.001-10 μM, and the final concentration of the nigericin was 10 μM. After the nigericin was added, the 96-well plate was placed in the 37° (C, 5% (202 cell incubator to culture the cells for 3-4 hours. After culture, 20 μL of MTT solution (5 mg/mL) was added to each well, the cells were incubated in the 37 °C, 5% $CO_2$ cell incubator for 1.5 hours, then 50 μL of 20% SDS solution (containing 0.1% hydrochloric acid) was added to each well, the 96-well plate was placed in the 37 °C, 5% $CO_2$ cell incubator for overnight incubation, and absorbance was tested with a microplate reader at a wavelength of 562 nm on the third day. A cell apoptosis protection rate of the drug was calculated according to the following formula:

$$\text{Cell apoptosis protection rate}=[(X-C_0)/(C-C_0)]\times 100\%$$

wherein, C, $C_0$ and X represent average absorbance values of the normal cell group, the blank control group, and the drug treatment group, respectively. Finally, cell survival curves were fitted by Graphpad Prism 5.0 software and $EC_{50}$ values of the compounds to be tested in inhibiting pyroptosis caused by NLRP3 inflammasomes were calculated.

TABLE 2

$EC_{50}$ values of compounds in the examples in vitro assay 1

| Number of compound | $EC_{50}$ value of pyroptosis |
|---|---|
| 1 | +++++ |
| 2 | +++++ |
| 3 | +++++ |
| 4 | +++++ |
| 5 | +++++ |
| 6 | +++++ |
| 7 | + |
| 8 | + |
| 9 | + |
| 10 | + |
| 11 | + |
| 12 | + |
| 13 | + |
| 14 | +++++ |
| 15 | +++++ |
| 16 | +++++ |
| 17 | +++++ |
| 18 | ++ |
| 19 | ++ |
| 20 | + |
| 21 | + |
| 22 | +++++ |
| 23 | +++++ |
| 24 | +++++ |
| 25 | +++++ |
| 26 | ++ |
| 27 | ++ |
| 28 | +++ |
| 29 | ++++ |
| 30 | ++++ |
| 31 | ++ |
| 32 | ++++ |
| 33 | ++++ |
| 34 | +++++ |
| 35 | ++ |
| 36 | ++ |
| 37 | +++++ |
| 38 | +++++ |
| 39 | +++++ |
| 40 | +++++ |
| 41 | +++++ |
| 43 | ++ |
| 44 | ++++ |
| 45 | ++ |
| 46 | ++++ |
| 47 | + |
| 48 | +++++ |
| 49 | +++++ |
| 50 | +++++ |
| 51 | ++++ |
| 52 | +++++ |
| 53 | +++ |
| 54 | +++++ |
| 55 | +++++ |
| 56 | +++++ |
| 57 | +++++ |
| 58 | +++++ |
| 59 | +++++ |
| 60 | +++++ |
| 61 | +++++ |
| 62 | +++++ |
| 63 | +++++ |
| 64 | +++++ |
| 65 | +++++ |
| 66 | +++ |
| 67 | +++ |
| 68 | ++ |
| 69 | + |
| 70 | + |
| 71 | + |
| 72 | ++++ |
| 73 | ++ |
| 74 | + |
| 75 | +++ |
| 76 | + |
| 77 | + |
| 78 | + |
| 79 | + |
| 80 | + |
| 81 | + |
| 82 | + |
| 83 | + |
| 84 | + |
| 85 | + |
| 86 | + |
| 87 | +++++ |
| 88 | ++++ |

For the $EC_{50}$ values, "+" indicates that the $EC_{50}$ value is greater than 1 μM; "++" indicates that the $EC_{50}$ value is greater than 500 nM and less than or equal to 1 μM; "+++"

indicates that the $EC_{50}$ value is greater than 100 nM and less than or equal to 500 nM; "++++" indicates that the $EC_{50}$ value is greater than 20 nM and less than or equal to 100 nM; and "+++++" indicates that the $EC_{50}$ value is less than 20 nM.

The invention claimed is:

1. A compound or a pharmaceutically acceptable salt thereof, wherein the compound having a structure shown in formula (I):

(I)

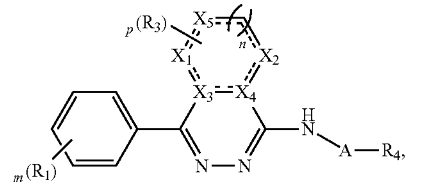

wherein:

n is 0;

m is an integer selected from 1 to 2;

p is an integer selected from 1 or 2;

$X_1$ and $X_2$ are independently selected from NH or N;

$X_5$ is CH:

$X_3$ and $X_4$ are independently selected from CH;

$R_1$ is selected from hydrogen, $C_{1-6}$ alkyl, $C_{1-6}$ alkoxy, halogen, or hydroxyl, and the $C_{1-6}$ alkyl, or $C_{1-6}$ alkoxy is optionally substituted by one or more halogens, wherein m $R_1$ is the same or different from each other;

$R_3$ is selected from hydrogen, $C_{1-6}$ alkyl, $C_{1-6}$ alkoxy, $C_{3-6}$ cycloalkyl, or halogen, and the $C_{1-6}$ alkyl, $C_{1-6}$ alkoxy, or $C_{3-6}$ cycloalkyl is optionally substituted by one or more halogens or $C_{1-3}$ alkyls, wherein p $R_3$ is the same or different from each other;

A is a single bond or $C_{1-3}$ alkylene chain;

$R_4$ is selected from piperidyl, morpholinyl, tetrahydropyranyl, or

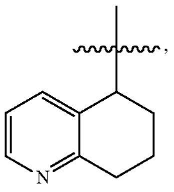 [SMILES: *C1CCCc2ncccc21]

and the piperidyl, morpholinyl, tetrahydropyranyl or

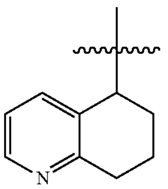 [SMILES: *C1CCCc2ncccc21]

is optionally substituted by one or more $C_{1-3}$ alkyls, or =O.

2. The compound of claim 1 or a pharmaceutically acceptable salt thereof, wherein $R_1$ is selected from $C_{1-3}$ alkyl, $C_{1-3}$ alkoxy, hydroxyl, or halogen, and the $C_{1-3}$ or $C_{1-3}$ alkoxy.

3. The compound of claim 1 or a pharmaceutically acceptable salt thereof, wherein the compound having a structure shown in formula (II):

(II)

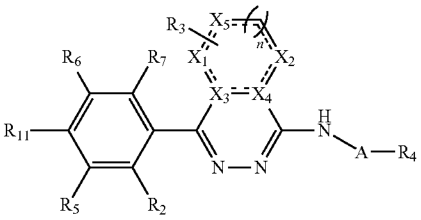

wherein:

n, $X_1$, $X_2$, $X_3$, $X_4$, $X_5$, $R_3$, $R_4$, and A are as defined according to claim 2;

$R_{11}$ is selected from trifluoromethyl, methyl, fluorine;

$R_2$ is selected from hydroxyl;

$R_5$, $R_6$, and $R_7$ are hydrogen.

4. The compound of claim 1 or a pharmaceutically acceptable salt thereof wherein the compound is selected from the following group,

36

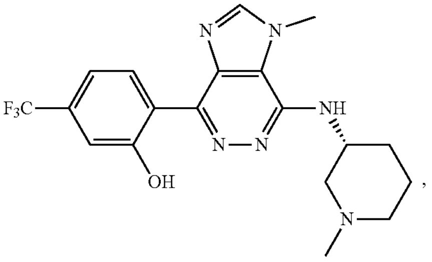

37

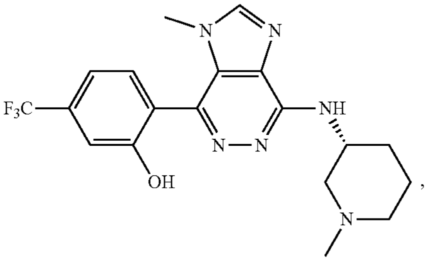

57

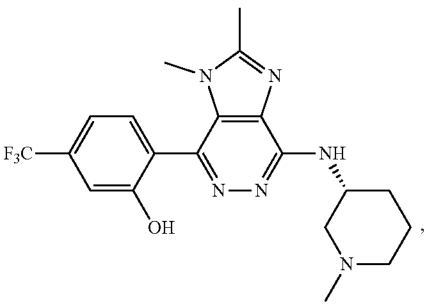

-continued
58
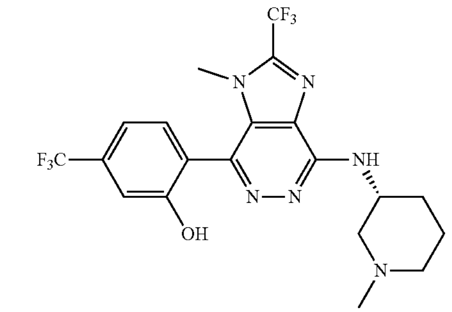
,
59
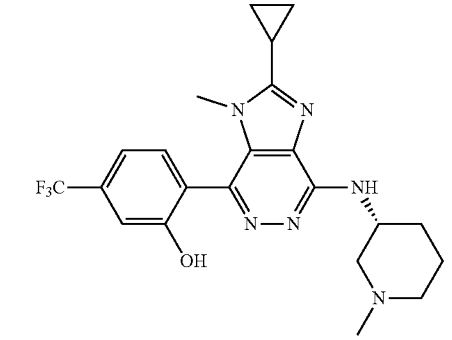
,
76
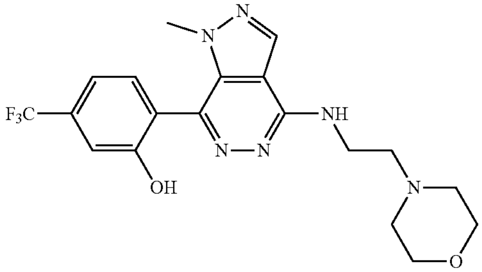
,
77
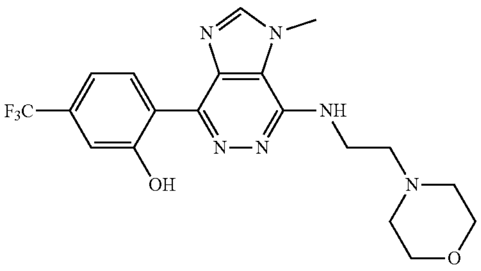
,
79
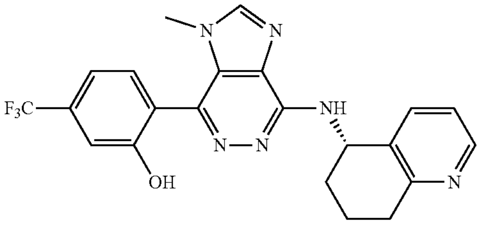
,
-continued
80
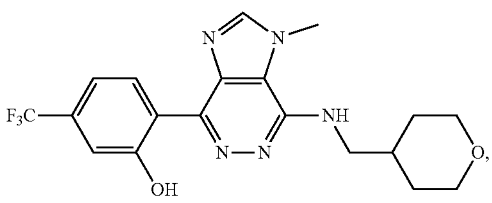
,
81
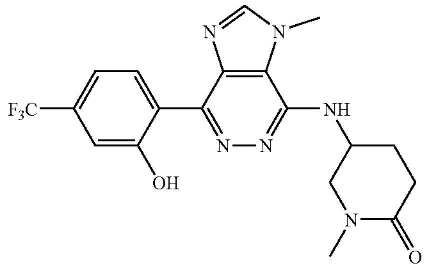
, and
82
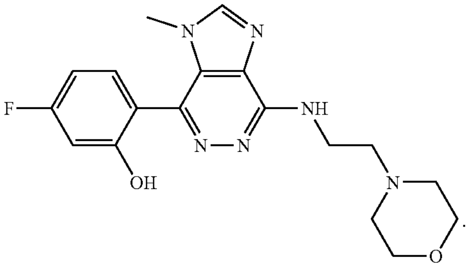
.
5. A preparation method for the compound of claim 3 or a pharmaceutically acceptable salt thereof, the method comprising the following steps:
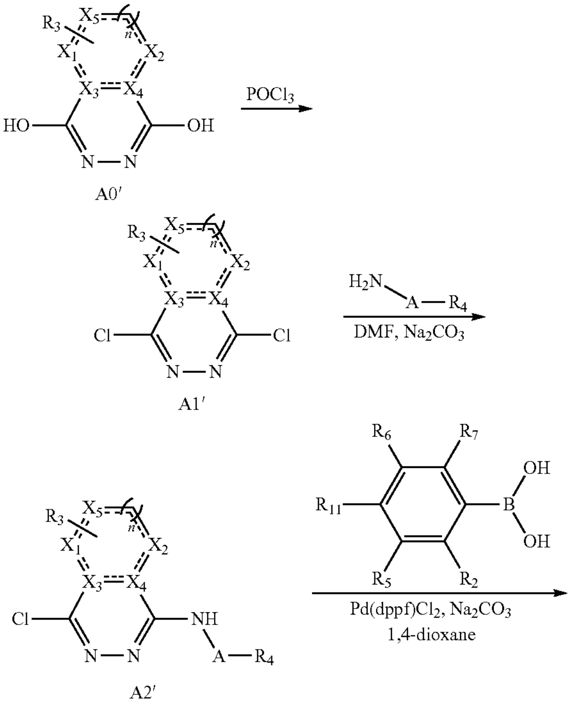

-continued

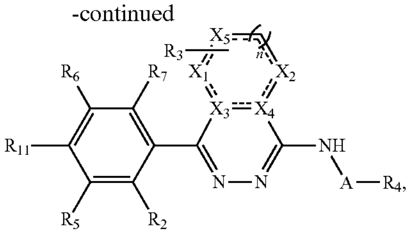

II step 1: dissolving a compound A0' in $POCl_3$, heating, reacting overnight, concentrating the reaction solution directly after complete reaction to remove the $POCl_3$, then slowly adding the oily crude product dropwise to ice water, extracting with ethyl acetate, and separating by column chromatography to obtain a target compound A1';

step 2: dissolving the compound A1', a corresponding amine, and $Na_2CO_3$ in dry DMF, heating the mixed system in a sealed tube, reacting overnight, adding the reaction solution to water after complete conversion of the raw materials, extracting with ethyl acetate, and separating by column chromatography to obtain a target compound A2';

step 3: adding the compound A2', boric acid, sodium carbonate, and $Pd(dppf)Cl_2$ to a mixed solvent of dioxane and water, displacing with nitrogen 3 times, heating, reacting for 3 hours, adding the reaction solution to water, extracting with ethyl acetate, and separating by column chromatography to obtain a target compound II.

6. A pharmaceutical composition, wherein the composition comprises the compound of claim 1 or a pharmaceutically acceptable salt thereof and pharmaceutically acceptable excipients.

7. A method of treating a disease mediated by NLRP3, comprising administering to a subject in need thereof a therapeutically effective amount of the compound of claim 1 or a pharmaceutically acceptable salt thereof or a pharmaceutical composition, wherein the pharmaceutical composition comprising a therapeutically effective amount of the compound of claim 2: the NLRP3 mediated disease is selected from rheumatoid arthritis, gouty arthritis, atherosclerosis, myocardial infarction, Parkinson's syndrome, Alzheimer's disease, infectious lung injury, pulmonary fibrosis, sepsis, ulcerative colitis, type II diabetes, sepsis, bacterial inflammation, familial Mediterranean fever, nephrotic syndrome, and myocarditis.

8. The compound of claim 1 or a pharmaceutically acceptable salt thereof, wherein $R_3$ is selected from hydrogen, $C_{1-3}$ alkyl, $C_{3-6}$ cycloalkyl, $C_{1-3}$ alkoxy, or halogen, and the $C_{1-3}$ alkyl, $C_{1-3}$ alkoxy, or $C_{3-6}$ cycloalkyl is optionally substituted by one to three halogens or $C_{1-3}$ alkyls.

9. The compound of claim 1 or a pharmaceutically acceptable salt thereof, wherein A is a single bond, $—CH_2—$, $—(CH_3)CH—$, or $—CH_2CH_2—$.

10. The compound of claim 1 or a pharmaceutically acceptable salt thereof, wherein $R_4$ is selected from

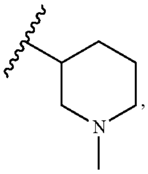,

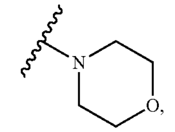,

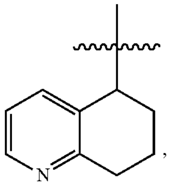,

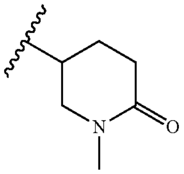

or

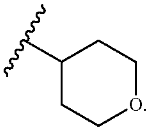.

11. The compound of claim 3 or a pharmaceutically acceptable salt thereof, wherein the compound having a structure shown in formula (Ivd):

(IVd)

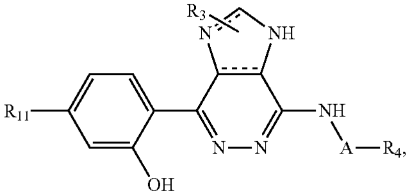

wherein:

$R_{11}$, $R_3$, $R_4$, and A are as defined according to claim 3.

12. The compound of claim 1 or a pharmaceutically acceptable salt thereof, wherein $R_1$ is selected from $C_{1-3}$ alkyl, $C_{1-3}$ alkoxy, hydroxyl or halogen, and the $C_{1-3}$ alkyl or $C_{1-3}$ alkoxy is optionally substituted by one to three fluorines.

13. The compound of claim 1 or a pharmaceutically acceptable salt thereof, wherein $R_1$ is selected from trifluoromethyl, difluoromethyl, methyl, fluorine, hydroxyl, or trifluoromethoxy.

14. The compound of claim 1 or a pharmaceutically acceptable salt thereof, wherein $R_1$ is selected from trifluoromethyl, methyl, fluorine, hydroxyl or trifluoromethoxy.

15. The compound of claim 1 or a pharmaceutically acceptable salt thereof, wherein $R_1$ is selected from trifluoromethyl, methyl or hydroxyl.

16. The compound of claim 1 or a pharmaceutically acceptable salt thereof, wherein $R_3$ is selected from $C_{1-3}$ alkyl, $C_{1-3}$ alkoxy or $C_{3-6}$ cycloalkyl, and the $C_{1-3}$ alkyl, $C_{1-3}$ alkoxy or $C_{3-6}$ cycloalkyl is optionally substituted by one to three fluorines or methyls.

17. The compound of claim 1 or a pharmaceutically acceptable salt thereof, wherein $R_3$ is selected from hydrogen, methyl, methoxy, cyclopropyl, ethyl, fluorine or trifluoromethyl.

18. The compound of claim 1 or a pharmaceutically acceptable salt thereof, wherein $R_3$ is selected from hydrogen, methyl.

19. The compound of claim 1 or a pharmaceutically acceptable salt thereof, wherein A is a single bond.
20. The compound of claim 1 or a pharmaceutically acceptable salt thereof, wherein $R_4$ is selected from
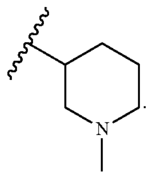 [SMILES: *C1CCCN(C)C1]
* * * * *